(12) United States Patent
Karuppasamy

(10) Patent No.: US 11,534,203 B2
(45) Date of Patent: Dec. 27, 2022

(54) METHODS AND APPARATUSES FOR ACCESSING A TARGET PATIENT TISSUE SITE

(71) Applicant: THE CLEVELAND CLINIC FOUNDATION, Cleveland, OH (US)

(72) Inventor: Karunakaravel Karuppasamy, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 264 days.

(21) Appl. No.: 16/650,938

(22) PCT Filed: Sep. 26, 2018

(86) PCT No.: PCT/US2018/052822
§ 371 (c)(1),
(2) Date: Mar. 26, 2020

(87) PCT Pub. No.: WO2019/067520
PCT Pub. Date: Apr. 4, 2019

(65) Prior Publication Data
US 2020/0367927 A1  Nov. 26, 2020

Related U.S. Application Data

(60) Provisional application No. 62/563,710, filed on Sep. 27, 2017.

(51) Int. Cl.
*A61B 17/34* (2006.01)
*A61M 25/00* (2006.01)
(Continued)

(52) U.S. Cl.
CPC ..... *A61B 17/3423* (2013.01); *A61M 25/0026* (2013.01); *A61M 25/09* (2013.01);
(Continued)

(58) Field of Classification Search
CPC ........ A61B 17/3423; A61B 2017/3445; A61B 17/3421; A61M 25/0026; A61M 25/09; A61M 29/00; A61M 25/0662
See application file for complete search history.

(56) References Cited

U.S. PATENT DOCUMENTS 4,257,422 A * 3/1981 Duncan ................. A61M 27/00
138/119
4,846,791 A   7/1989 Hattler et al.
(Continued)

FOREIGN PATENT DOCUMENTS

EP   2191793 A2    6/2010
WO   2002/13899 A1  2/2002

OTHER PUBLICATIONS

PCT International Search Report and Written Opinion for corresponding PCT Application Serial No. PCT/US2018/052822, dated Nov. 29, 2018, pp. 1-13.

*Primary Examiner* — Richard G Louis
(74) *Attorney, Agent, or Firm* — Tarolli, Sundheim, Covell & Tummino LLP

(57) ABSTRACT

An introducer sheath is provided for inserting at least one medical instrument directly toward a target patient tissue site. A plurality of lumens extend longitudinally between sheath proximal and distal ends of the introducer sheath. A septum extends between the sheath proximal and distal ends and selectively laterally separates each of the sheath lumens from one another. The septum is at least partially formed from a deformable and elastomeric material. The septum has a biased condition in which the plurality of sheath lumens are at least partially isolated from one another. The septum is selectively deflectable from the biased condition to at least partially place at least one of the plurality of sheath lumens in fluid communication with at least one other of the plurality of sheath lumens.

20 Claims, 114 Drawing Sheets

(51) Int. Cl.
  *A61M 25/09*   (2006.01)
  *A61M 29/00*   (2006.01)
  *A61M 25/06*   (2006.01)

(52) U.S. Cl.
  CPC ..... *A61M 29/00* (2013.01); *A61B 2017/3445* (2013.01); *A61M 25/0662* (2013.01)

(56) References Cited

U.S. PATENT DOCUMENTS

| | | |
|---|---|---|
| 6,544,270 B1 | 4/2003 | Zhang |
| 2006/0235458 A1* | 10/2006 | Belson ............... A61B 1/00135 606/191 |
| 2013/0211324 A1 | 8/2013 | Voss et al. |
| 2014/0039586 A1 | 2/2014 | Barker et al. |
| 2015/0360000 A1 | 12/2015 | Sansoucy |

* cited by examiner

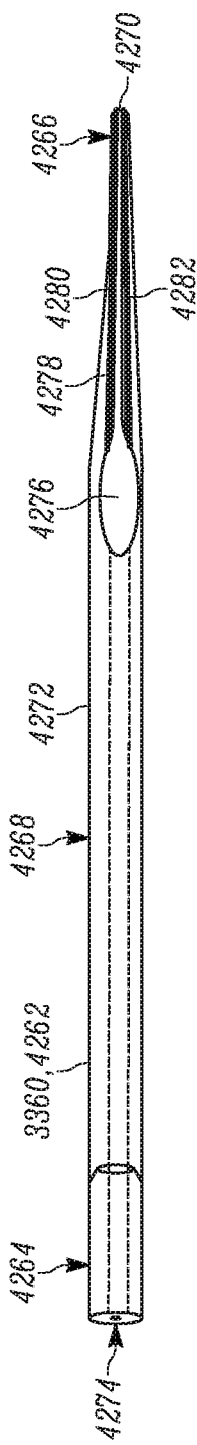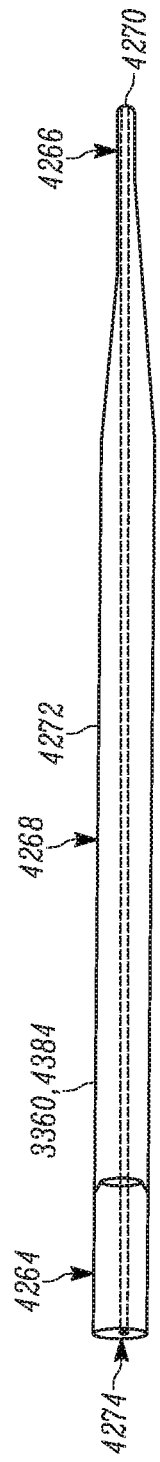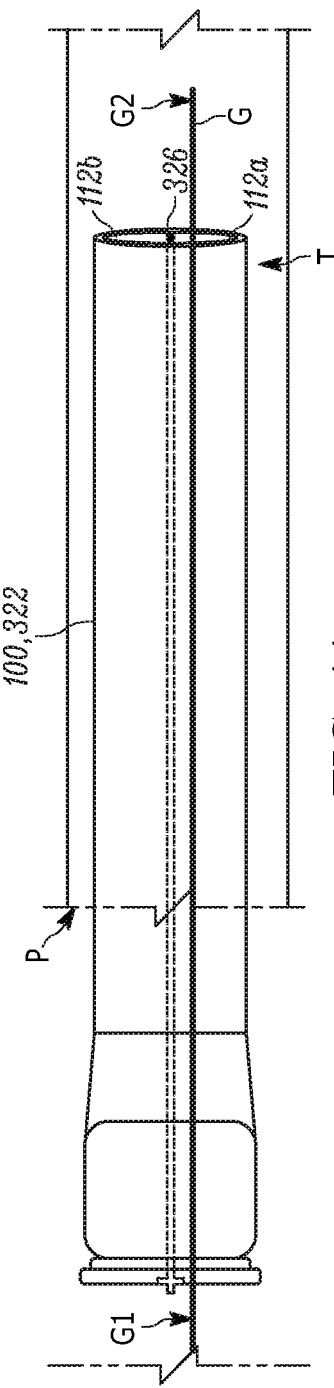

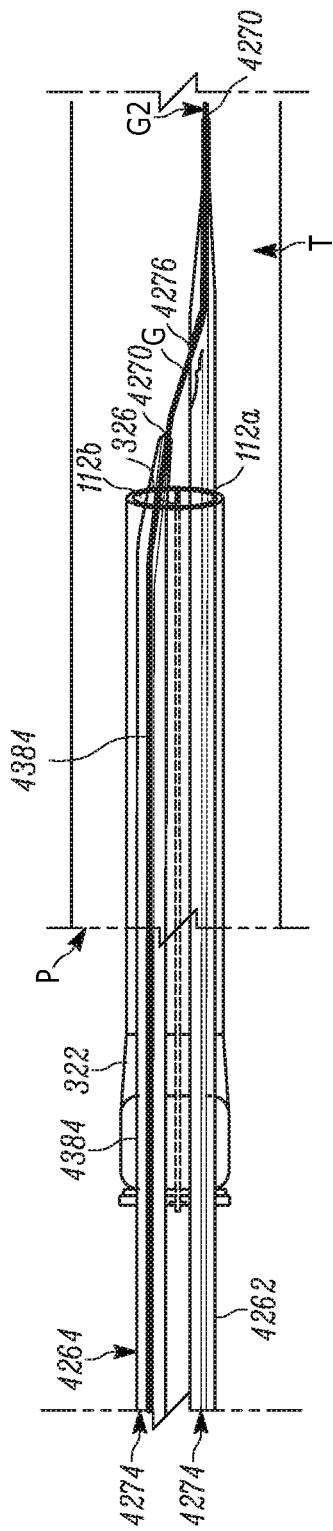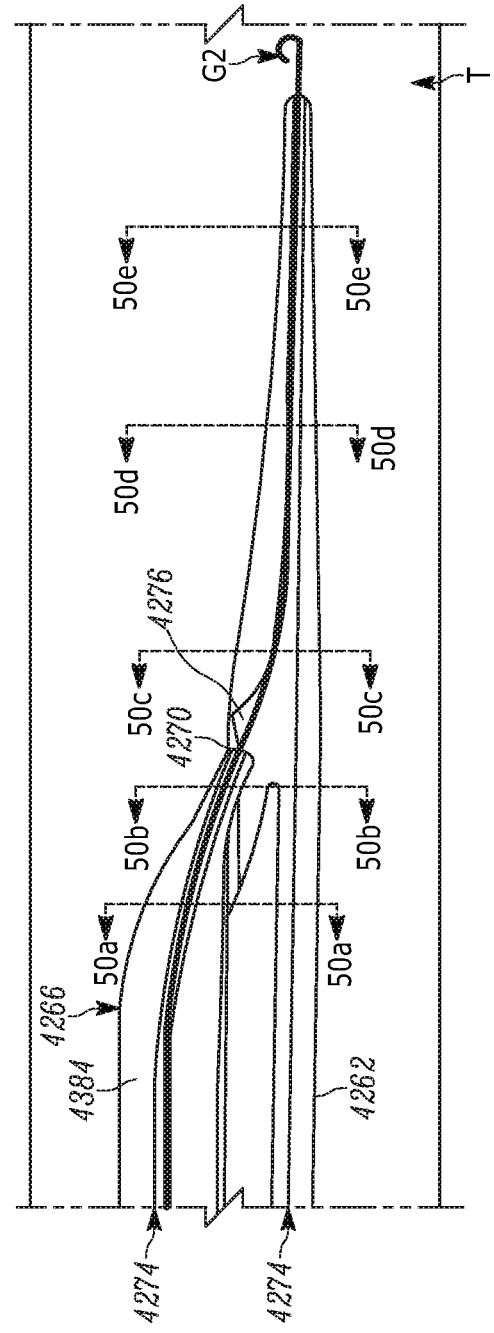
FIG. 49
FIG. 50

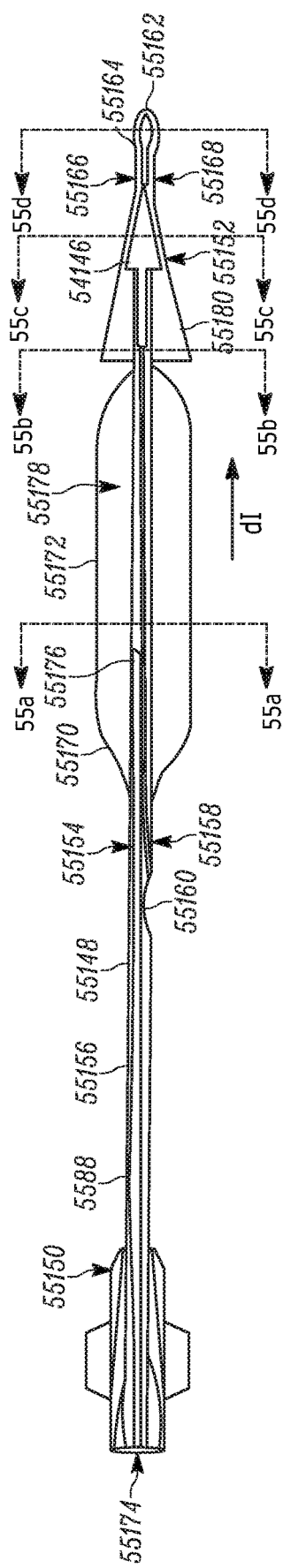
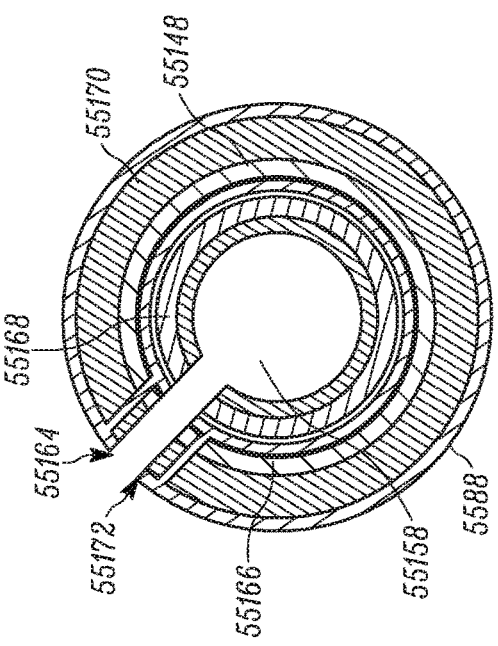
FIG. 55
FIG. 55a

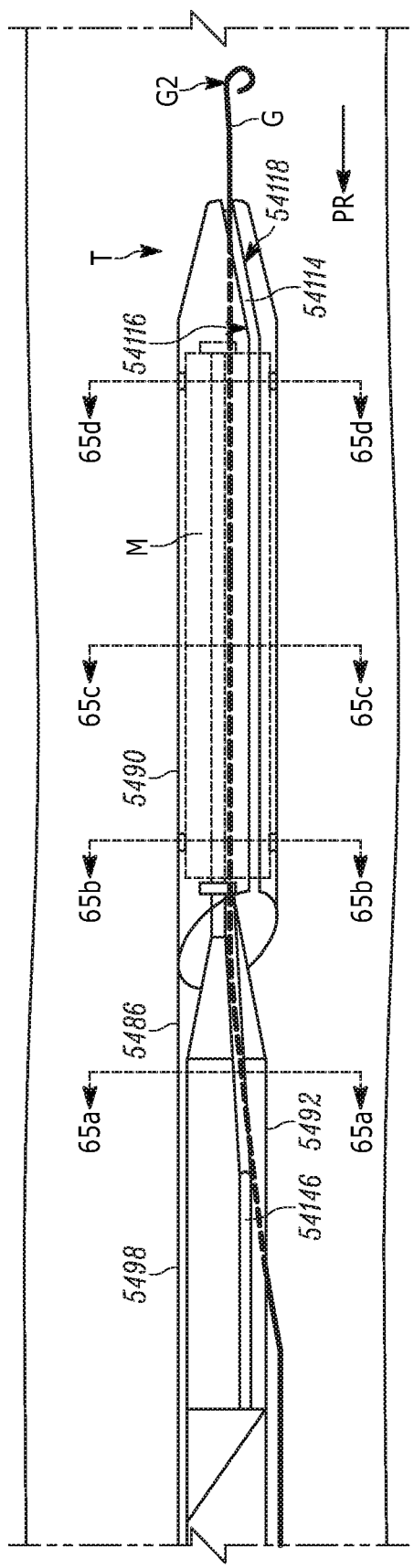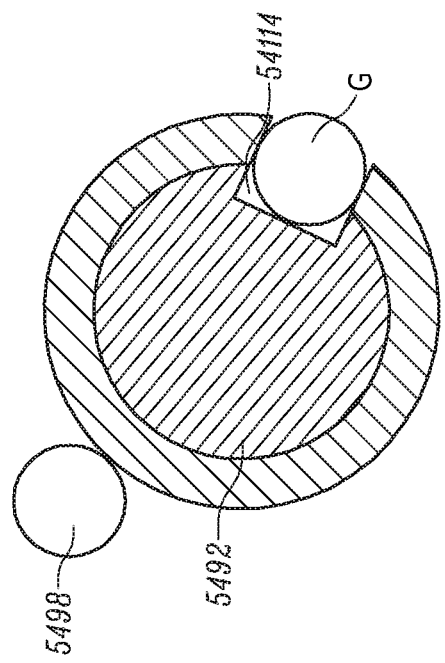
FIG. 65
FIG. 65a

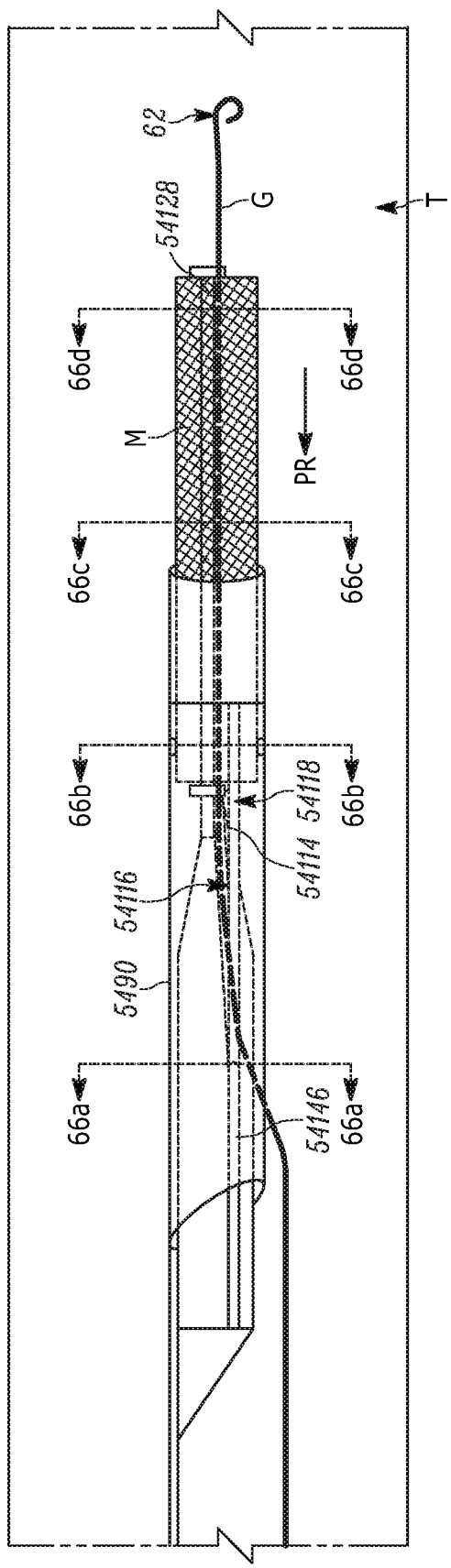
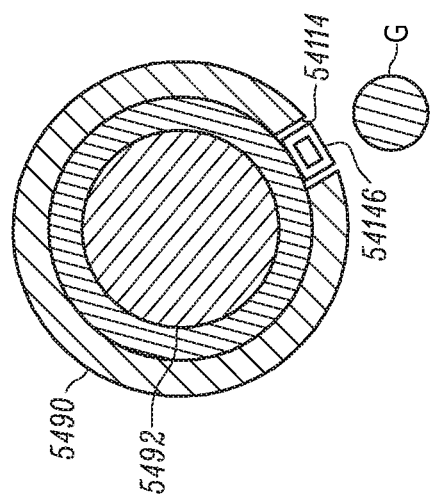
FIG. 66
FIG. 66a

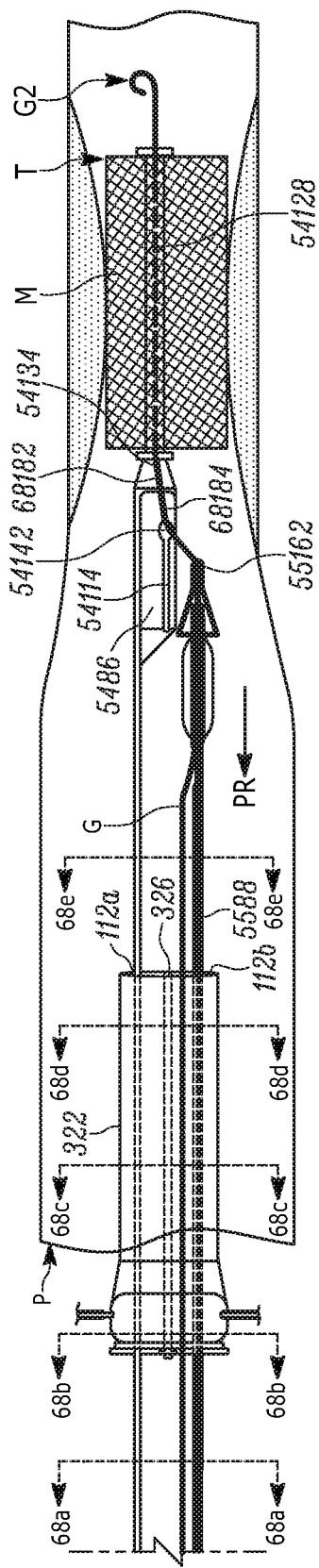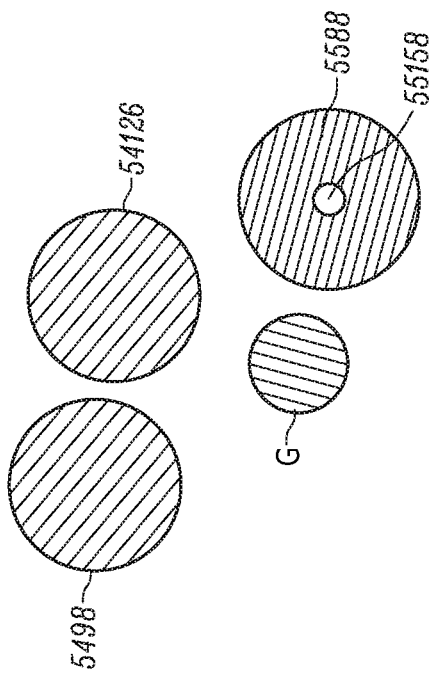
FIG. 68
FIG. 68a

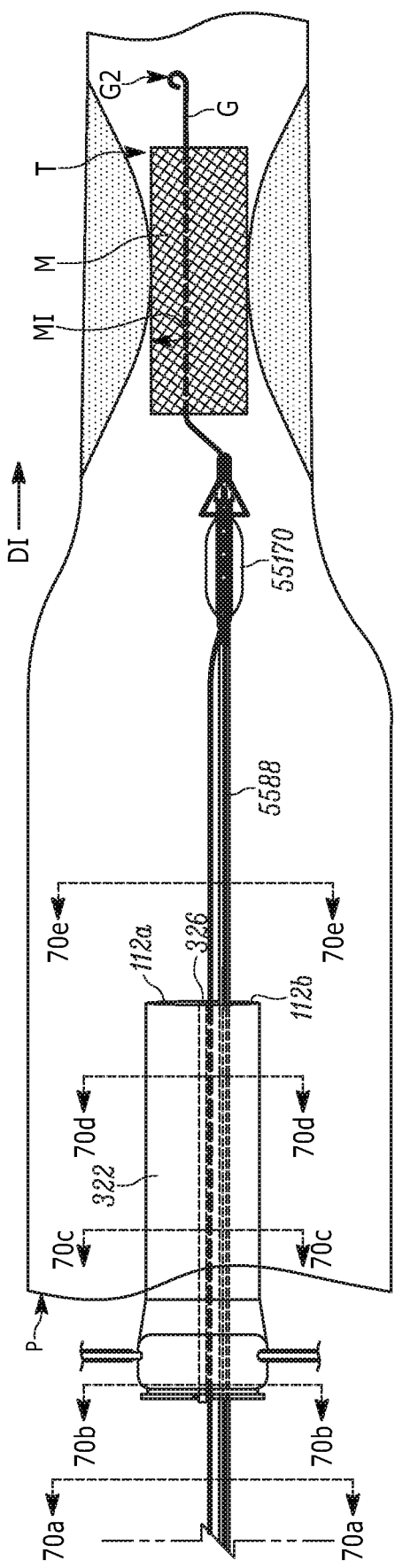
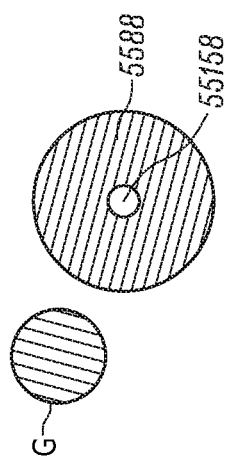
FIG. 70
FIG. 70a

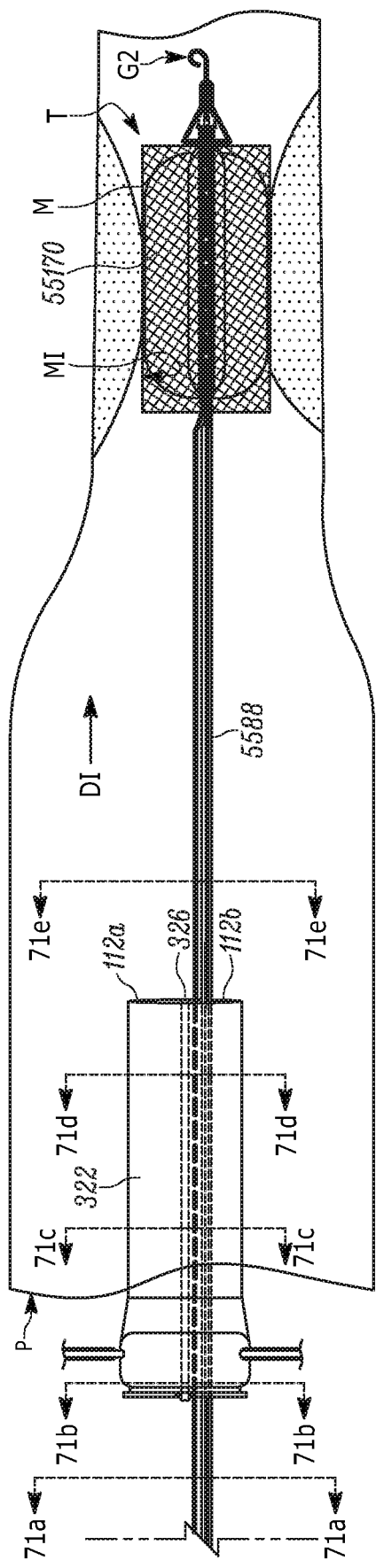
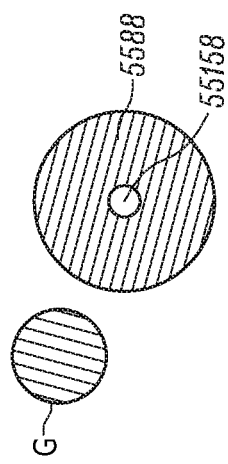
FIG. 71
FIG. 71a

METHODS AND APPARATUSES FOR ACCESSING A TARGET PATIENT TISSUE SITE

RELATED APPLICATION

This application claims priority from U.S. Provisional Application No. 62/563,710, filed 27 Sep. 2017, the subject matter of which is incorporated herein by reference in its entirety.

TECHNICAL FIELD

This disclosure relates to apparatuses and methods for use of an introducer sheath and, more particularly, to a method and device for inserting at least one medical instrument directly toward a target patient tissue site, a method and device for inserting an introducer sheath through a patient tissue access point, and a method and device for transitioning a guidewire between a plurality of lumens within a patient.

BACKGROUND

Certain medical procedures include inserting multiple medical instruments into patient tissue, either sequentially (one after another) or simultaneously. An example procedure for a sequential usage of medical instruments may include, but is not limited to, dilating a diseased patient lumen using a balloon dilation device followed by a stent deployed in the same lumen. A few examples of procedures for the simultaneous usage of multiple medical instruments in different sites include, but are not limited to, a procedure requiring delivering therapy to two or more patient sites simultaneously, such as thrombolysis infusion catheters to break down clots in two or more sites, or embolization catheters to block flow in two or more sites. A few examples of procedures for the simultaneous usage of multiple medical instruments at or near one disease site may include, but are not limited to, using a diagnostic instrument such as an intravascular ultrasound catheter, and using an interventional instrument such as implant delivery catheter. Procedures that involve simultaneous usage of multiple medical instruments may include creating multiple puncture points for inserting the medical instruments. Multiple puncture points may lead to an increase in patient discomfort, complications, cost, radiation exposure, and/or procedure time. Procedures that may include the sequential operation of multiple medical instruments through a single puncture point may require the complete removal of one instrument from the patient before another instrument can be advanced. This may lead to prolonged patient discomfort, increased radiation exposure, and/or increased procedure time.

SUMMARY

In an aspect, an introducer sheath is provided. A plurality of lumens extend longitudinally between sheath proximal and distal ends of the introducer sheath. A septum extends between the sheath proximal and distal ends and selectively laterally separates each of the sheath lumens from one another. The septum is at least partially formed from a deformable and elastomeric material. The septum has a biased condition in which the plurality of sheath lumens are at least partially isolated from one another. The septum is selectively deflectable from the biased condition to at least partially place at least one of the plurality of sheath lumens in fluid communication with at least one other of the plurality of sheath lumens.

In an aspect, a method for inserting at least one medical instrument directly toward a target patient tissue site is provided. An introducer sheath has a plurality of sheath lumens extending between sheath proximal and distal ends of the introducer sheath is provided. A guidewire distal end is inserted into a target patient tissue site. The guidewire proximal end is directed through a first sheath lumen of the plurality of sheath lumens. The introducer sheath is directed toward the target patient tissue site along the guidewire. The guidewire proximal end is directed at least partially through a first medical instrument. The first medical instrument is directed to the target patient tissue site along the guidewire and at least partially through a second sheath lumen of the plurality of sheath lumens. The first medical instrument urges the guidewire from the first sheath lumen to the second sheath lumen as the first medical instrument moves at least partially through the second sheath lumen, while the guidewire is maintained at the target patient tissue site.

In an aspect, for inserting an introducer sheath through a patient tissue access point is provided. The introducer sheath has a plurality of sheath lumens extending between sheath proximal and distal ends of the introducer sheath is provided. A guidewire distal end is inserted through the patient tissue access point. A guidewire proximal end is directed through a first sheath lumen of the plurality of sheath lumens. The guidewire proximal end is directed at least partially through a first medical instrument. The first medical instrument is directed over the guidewire and at least partially through the first sheath lumen. The guidewire proximal end is directed at least partially through a second medical instrument. The second medical instrument is directed over the guidewire and at least partially through a second sheath lumen of the plurality of sheath lumens. The second medical instrument urges the guidewire from the first sheath lumen to the second sheath lumen as the second medical instrument moves at least partially through the second sheath lumen, while the guidewire is maintained through the patient tissue access point. The first and second medical instruments are aligned with the introducer sheath so that at least a portion of both of the first and second medical instruments extend out from the introducer sheath and form a smooth outer contour with the sheath distal end. With the first and second medical instruments aligned with the introducer sheath, the introducer sheath, the first medical instrument, and the second medical instrument are collectively directed through the patient tissue access point along the guidewire.

In an aspect, for transitioning a guidewire between a plurality of lumens within a patient is provided. An introducer sheath is provided. A plurality of sheath lumens extend between sheath proximal and distal ends of the introducer sheath. A selectively removable septum extends between the sheath proximal and distal ends and selectively separates each of the plurality of sheath lumens from one another to at least partially isolate each of plurality of sheath lumens from one another when the removable septum is inserted into the introducer sheath. At least one of the plurality of sheath lumens is in fluid communication with at least one other of the plurality of sheath lumens when the removable septum is removed from the introducer sheath. A guidewire distal end is inserted into a target patient tissue site. A guidewire proximal end is directed through a first sheath lumen of the plurality of sheath lumens. The introducer sheath is directed toward the target patient tissue site along the guidewire. The removable septum is removed from the introducer sheath. With the removable septum removed from the introducer sheath, the guidewire proximal end is urged from the first sheath lumen to a second sheath lumen of the plurality of sheath lumens. With the guidewire proximal end in the second sheath lumen, the removable septum is inserted into the introducer sheath. The removable septum urges the guidewire from the first sheath lumen to the second sheath lumen as the removable septum is inserted into the introducer sheath, while the guidewire is maintained at the target patient tissue site.

BRIEF DESCRIPTION OF THE DRAWINGS

For a better understanding, reference may be made to the accompanying drawings, in which:

FIGS. 42-53 illustrate an example sequence of operation of a portion of the aspect of FIG. 3, including cross-sectional views.

DESCRIPTION OF ASPECTS OF THE DISCLOSURE

Figure 1:
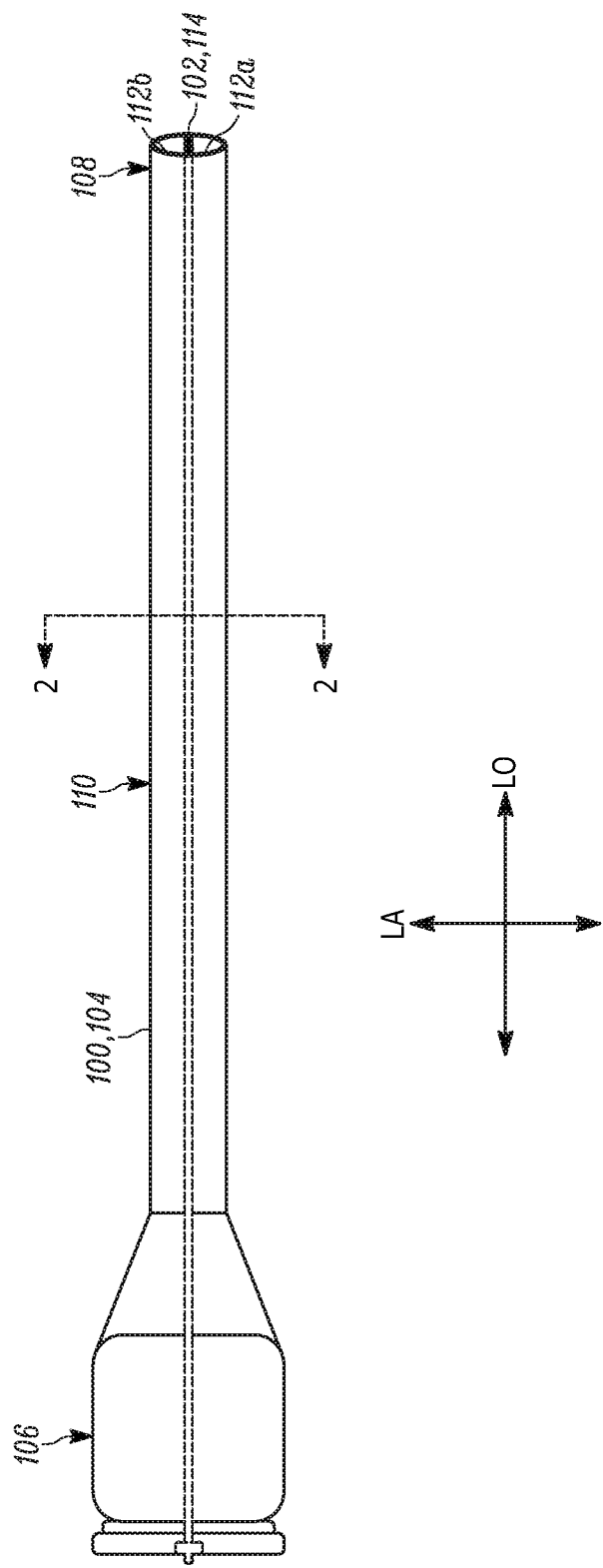
FIG. 1 is a top view of an introducer sheath according to one aspect of the present invention.

Unless defined otherwise, all technical and scientific terms used herein have the same meaning as is commonly understood by one of skill in the art to which the present disclosure pertains.

As used herein, the term "patient" may refer to any warm-blooded organism including, but not limited to, human beings, pigs, rats, mice, dogs, goats, sheep, horses, monkeys, apes, rabbits, cattle, farm animals, livestock, etc.

As used herein, the term "user" can be used interchangeably to refer to an individual who prepares for, assists with, and/or performs a procedure.

As used herein, the singular forms "a," "an" and "the" may include the plural forms as well, unless the context clearly indicates otherwise. It will be further understood that the terms "comprises" and/or "comprising," as used herein, may specify the presence of stated features, steps, operations, elements, and/or components, but do not preclude the presence or addition of one or more other features, steps, operations, elements, components, and/or groups thereof.

As used herein, the term "and/or" may include any and all combinations of one or more of the associated listed items.

As used herein, phrases such as "between X and Y" may be interpreted to include X and Y.

As used herein, the phrase "at least one of X and Y" can be interpreted to include X, Y, or a combination of X and Y. For example, if an element is described as having at least one of X and Y, the element may, at a particular time, include X, Y, or a combination of X and Y, the selection of which could vary from time to time. In contrast, the phrase "at least one of X" can be interpreted to include one or more Xs.

It will be understood that when an element is referred to as being "on," "attached" to, "contacting," etc., another element, it can be directly on, attached to or contacting the other element or intervening elements may also be present. In contrast, when an element is referred to as being, for example, "directly on," "directly attached" to or "directly contacting" another element, there are no intervening elements present. It will also be appreciated by those of skill in the art that references to a structure or feature that is disposed "adjacent" another feature may not have portions that overlap or underlie the adjacent feature.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or Figures unless specifically indicated otherwise.

The invention comprises, consists of, or consists essentially of the following features, in any combination.

An introducer sheath 100 having a septum 102 is provided. The introducer sheath 100 may be a sheath, a catheter, or any other appropriate elongated device that is substantially hollow. The introducer sheath 100 and the septum 102 may have alternate configurations, some of which will be discussed below. FIGS. 1-31 depict example alternate configurations of the introducer sheath 100 and the septum 102. Although FIGS. 1-31 depict example alternate configurations of the introducer sheath 100 and the septum 102, any of these configurations may, or may not, include features (and accordingly the function of those features) of any other of the configurations whether or not expressly stated and/or shown. Further, similar elements shared between the alternate configurations of the introducer sheath 100 and the septum 102 include common reference characters.

Figure 2A:
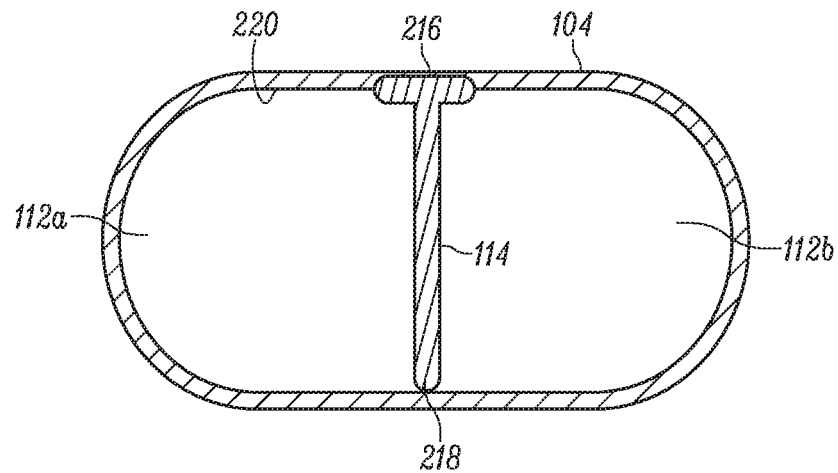
FIGS. 2a-2b depict cross-sectional views of the aspect of FIG. 1, in example use configurations.
Figure 2B:
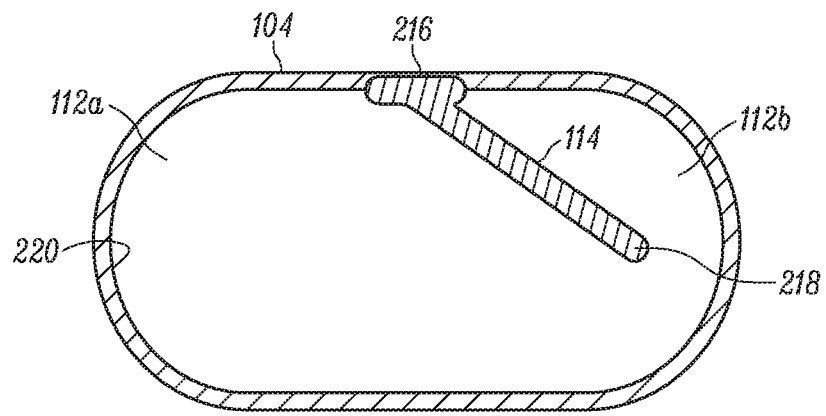

FIGS. 1-2b depict an example alternate configuration for the introducer sheath 100, referred to as introducer sheath A 104. The introducer sheath A 104 has a sheath proximal end 106 and a sheath distal end 108. The sheath proximal end 106 and the sheath distal end 108 are longitudinally spaced apart by an elongate sheath body 110. The term "longitudinal" is used herein to indicate a substantially horizontal direction, in the orientation of FIG. 1, and is shown at LO in FIG. 1. The introducer sheath A 104 has a plurality of sheath lumens (shown here as the sheath lumens 112a and 112b) extending longitudinally between the sheath proximal and distal ends 106, 108 of the introducer sheath A 104.

The introducer sheath A 104 includes an example configuration of the septum 102, referred to as septum A 114. The septum A 114 longitudinally extends between the sheath proximal and distal ends 106, 108 and selectively laterally separates each of the sheath lumens 112a, 112b from one another. The term "lateral" is used herein to indicate a direction substantially perpendicular to the "longitudinal" direction, is shown as the vertical direction in the orientation of FIG. 1, and is shown at LA in FIG. 1. As shown in FIGS. 2a-b, the septum A 114 has a septum first end 216 and a laterally spaced septum second end 218. The septum first end 216 is attached to a portion of an interior wall 220 of the introducer sheath A 114.

The septum A 114 may be at least partially formed from a deformable and elastomeric material. The deformable and elastomeric material forming the septum A 114 may be the same material that at least partially forms the introducer sheath A 104 or a material that is at least slightly more deformable than the material used to at least partially form the introducer sheath A 104. As shown in FIG. 2a, the septum A 114 has a biased condition in which the plurality of sheath lumens 112a, 112b are at least partially isolated from one another. In other words, in the biased condition, there is substantially no fluid communication between each of the sheath lumens 112a, 112b of the plurality of sheath lumens 112a, 112b. Thus, in the biased condition, at least a portion of the septum A 114 and at least a portion of the interior wall 220 of the introducer sheath A 104 collectively define each of the sheath lumens 112a, 112b.

The septum second end 218 abuts a portion of the interior wall 220 opposite from the septum first end 216 when the septum A 114 is in the biased condition to at least partially isolate each of plurality of sheath lumens 112a, 112b from one another. The term "abut" is defined herein as to directly contact and/or be adjacent to. As shown in FIG. 2b, the septum A 114 may be selectively deflectable from the biased condition to an opened condition to at least partially place at least one of the plurality of sheath lumens 112a, 112b in fluid communication with at least one other of the plurality of sheath lumens 112a, 112b. The deflection from the biased condition occurs responsive to at least one of an applied force and an elastic deformation of the septum A 114. A user may directly and/or indirectly apply a force to the septum A 114 to deflect the septum A 114 from the biased condition. Upon removal of the applied force, the septum A 114 automatically moves or "springs" back to the biased condition from being deflected, due to the inherent properties of the elastomeric material. When the septum A 114 is selectively deflected from the biased condition to the opened condition, at least a portion of the septum second end 218 is spaced apart from the portion of the interior wall 220 opposite from the septum first end 216 to at least partially place at least one of the plurality of sheath lumens 112a, 112b in fluid communication with at least one other of the plurality of sheath lumens 112a, 112b.

Figure 3:
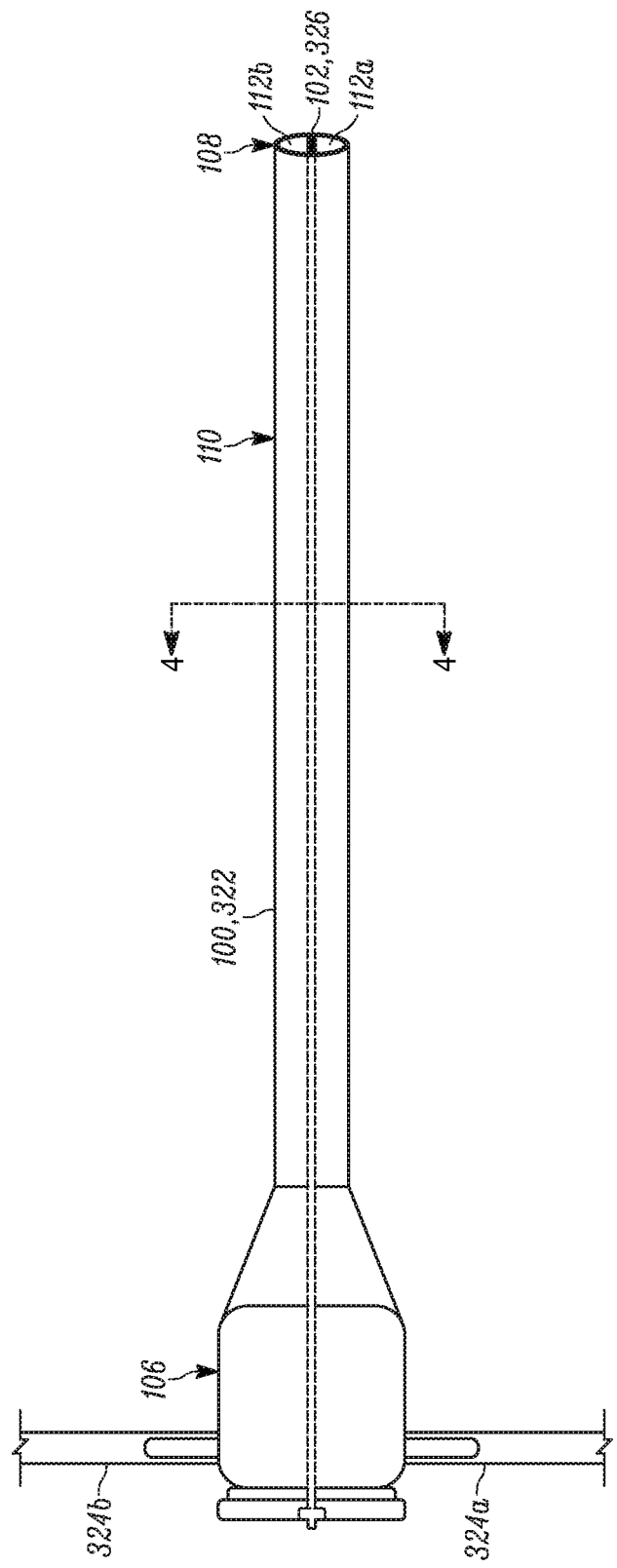
FIG. 3 is a top view of an element of the aspect of FIG. 1, in an alternate configuration.
Figure 4A:
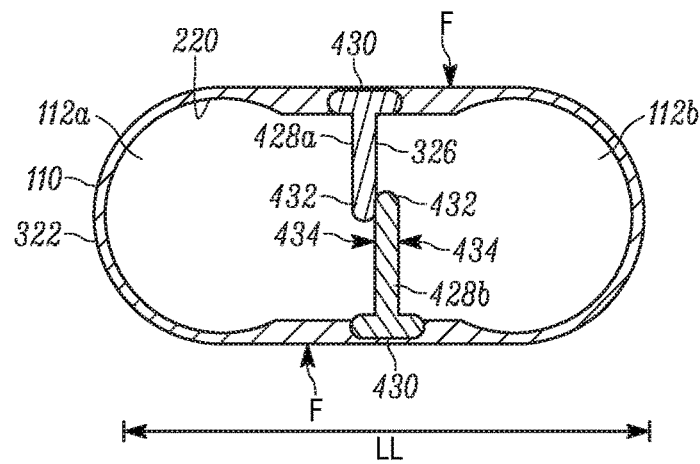
FIGS. 4a-4b depict cross-sectional views of the aspect of FIG. 3, in example use configurations.
Figure 4B:
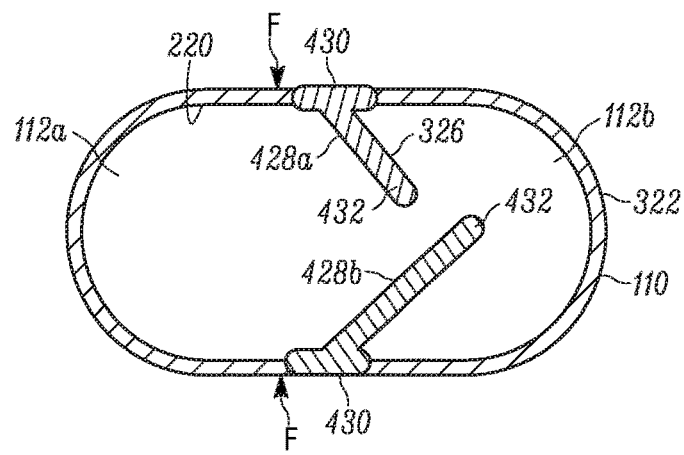

FIGS. 3-4b depict an example alternate configuration for the introducer sheath 100, referred to as an introducer sheath B 322. The sheath proximal end 106 of the introducer sheath B 322 may include a plurality of side ports 324 (shown here as the side ports 324a and 324b). Each of the side ports 324a, 324b is selectively in fluid communication with at least one of the plurality of sheath lumens 112a, 112b so that fluid may flow into, or out of, at least one of the plurality of sheath lumens 112a, 112b through a corresponding side port 324a, 324b.

The introducer sheath B 322 includes an example configuration of the septum 102, referred to as a septum B 326. The septum B 326 longitudinally extends between the sheath proximal and distal ends 106, 108 and selectively laterally separates each of the sheath lumens 112a, 112b from one another. As shown in FIGS. 4a-b, the septum B 326 comprises a plurality of segments 428 (shown here as the segments 428a and 428b). Each of the segments 428a, 428b has a segment first end 430 and a laterally spaced segment second end 432. Each of the segment first ends 430 is attached to a portion of the interior wall 220 of the introducer sheath B 322 and spaced apart from other segment first ends 430.

The septum B 326 may be at least partially formed from a deformable and elastomeric material. As shown in FIG. 4a, the septum B 326 has a biased condition in which the plurality of sheath lumens 112a, 112b are at least partially isolated from one another. Thus, in the biased condition, at least a portion of the septum B 326 and at least a portion of the interior wall 220 of the introducer sheath B 322 collectively define each of the sheath lumens 112a, 112b. Each of the segment second ends 432 abut a portion of another of the segment second ends 432 when the septum B 326 is in the biased condition to at least partially isolate each of plurality of sheath lumens 112a, 112b from one another.

As shown in FIG. 4b, the septum B 326 may be selectively deflectable from the biased condition to the opened condition to at least partially place at least one of the plurality of sheath lumens 112a, 112b in fluid communication with at least one other of the plurality of sheath lumens 112a, 112b. The deflection from the biased condition occurs responsive to at least one of an applied force and an elastic deformation of the septum B 326. A user may directly and/or indirectly apply a force to the septum B 326 to deflect the septum B 326 from the biased condition. Upon removal of the applied force, the septum B 326 automatically moves or "springs" back to the biased condition from being deflected, due to the inherent properties of the elastomeric material. When the septum B 326 is selectively deflected from the biased condition to the opened condition, at least a portion of the segment second end 432 of at least one of the segments 428a, 428b is spaced apart from the segment second end 432 of at least one other of the segments 428a, 428b to at least partially place at least one of the plurality of sheath lumens 112a, 112b in fluid communication with at least one other of the plurality of sheath lumens 112a, 112b.

FIGS. 4a-14 depict alternate configurations of certain portions of the introducer sheath B 322. In FIGS. 4a-4b, the sheath body 110 is stadium-shaped in cross-section, with two substantially flat opposing sides (shown at F in FIGS.

4a-4b). The term "stadium" is defined herein as a geometric shape constructed of a rectangle with semicircles at a pair of opposite sides. As shown in FIG. 4a, an inward surface 434 of each of the sheath lumens 112a, 112b is substantially defined by the segments 428a, 428b of the septum B 326 when the septum B 326 is in the biased condition.

Figure 5:
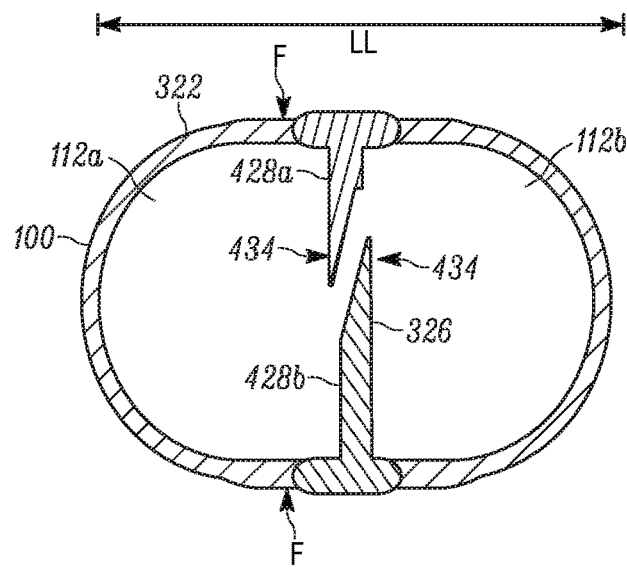
FIGS. 5-9 depict cross-sectional views of an element of the aspect of FIG. 3, in alternate configurations.

In FIG. 5, the sheath body 110 is stadium-shaped in cross-section, with two substantially flat opposing sides F. The sheath body 110 of FIG. 5 has rotational symmetry of the order 2. The elliptical sheath body 110 of FIG. 5 differs from the elliptical sheath body 110 of FIGS. 4a-b in that a lateral length LL of the sheath body 110 in FIG. 5 is smaller than the lateral length LL of the sheath body 110 in FIG. 4a. As shown in FIG. 5, the inward surface 434 of each of the sheath lumens 112a, 112b is substantially defined by the segments 428a, 428b of the septum B 326 when the septum B 326 is in the biased condition and each of the plurality of sheath lumens 112a, 112b is matched in cross-sectional area with each other of the plurality of sheath lumens 112a, 112b.

Figure 6:
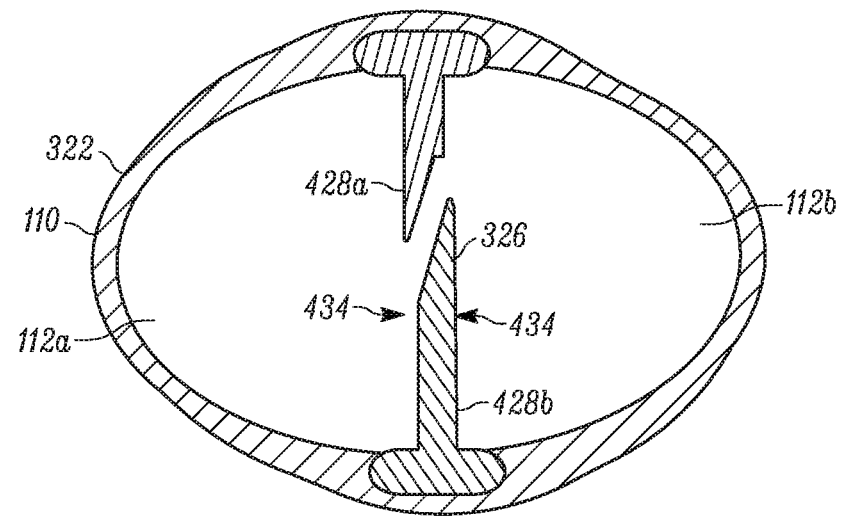

In FIG. 6, the sheath body 110 has the shape of an ellipse in cross-section. The sheath body 110 of FIG. 6 has rotational symmetry of the order 2. The inward surface 434 of each of the sheath lumens 112a, 112b of the sheath body 110 of FIG. 6 is substantially defined by the segments 428a, 428b of the septum B 326 when the septum B 326 is in the biased condition and each of the plurality of sheath lumens 112a, 112b is matched in cross-sectional area with each other of the plurality of sheath lumens 112a, 112b.

Figure 7:
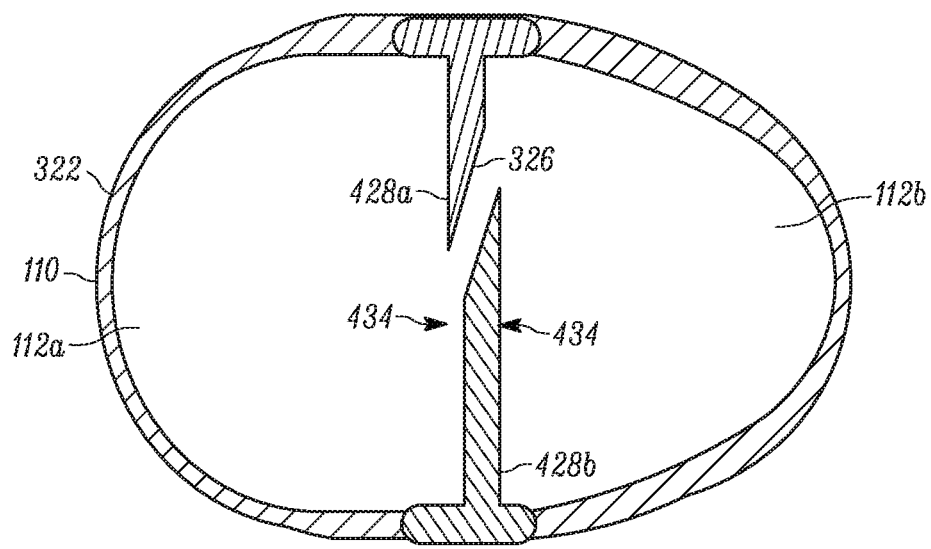

In FIG. 7, the sheath body 110 is asymmetrically ovate, or, in other words, egg-shaped, in cross-section. The sheath body 110 of FIG. 7 has rotational symmetry of the order 1. At least one of the sheath lumens 112a, 112b shown in FIG. 7 is larger than the other of the sheath lumens 112a, 112b. Thus, each of the plurality of sheath lumens 112a, 112b is not matched in cross-sectional area with each other of the plurality of sheath lumens 112a, 112b. The inward surface 434 of each of the sheath lumens 112a, 112b of FIG. 7 is substantially defined by the segments 428a, 428b of the septum B 326 when the septum B 326 is in the biased condition.

Figure 8:
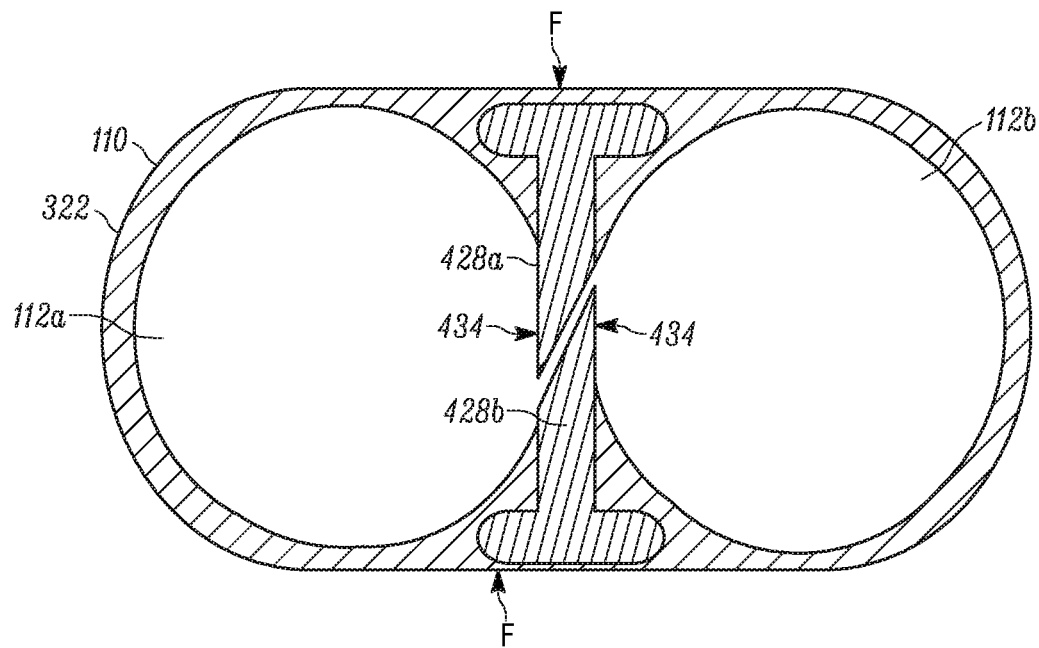

In FIG. 8, the sheath body 110 is stadium-shaped in cross-section, with two substantially flat opposing sides F. The sheath body 110 of FIG. 8 has rotational symmetry of the order 2. The inward surface 434 of each of the sheath lumens 112a, 112b of FIG. 8 is only partially defined by the segments 428a, 428b of the septum B 326 when the septum B 326 is in the biased condition. In other words, the segments 428a, 428b of the septum B 326 of the sheath body 110 of FIG. 8 make up a smaller portion of the inward surface 434 of each of the sheath lumens 112a, 112b than do the segments 428a, 428b of the septum B 326 of the sheath body 110 of FIGS. 4a-4b. Each of the plurality of sheath lumens 112a, 112b of FIG. 8 is substantially circular-shaped in cross-section and is matched in cross-sectional area with each other of the plurality of sheath lumens 112a, 112b.

Figure 9:
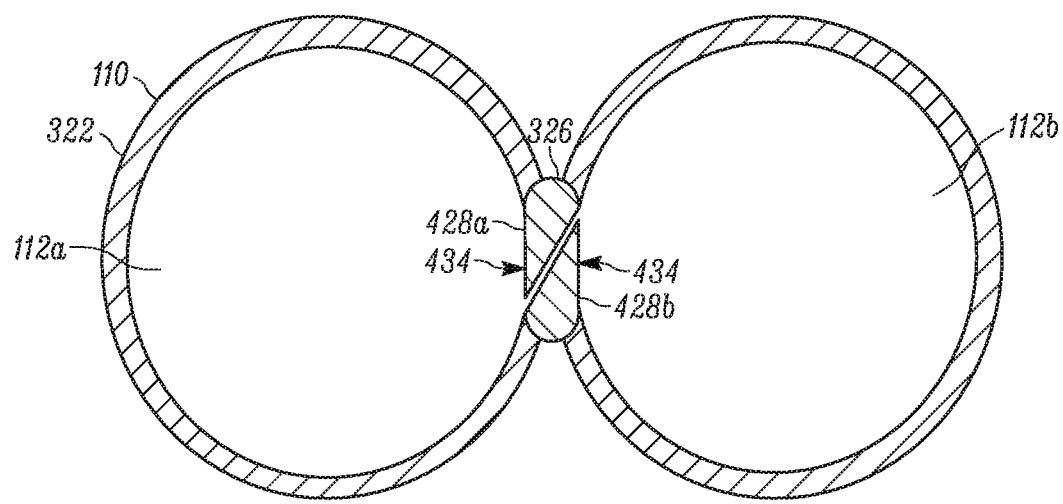

In FIG. 9, the sheath body 110 is in the shape of a lemniscate in cross-section. The term "lemniscate" is defined herein as a plane curve with a characteristic shape, which is similar to that of the numeral 8, consisting of two loops that meet at a central point. The sheath body 110 of FIG. 9 has rotational symmetry of the order 2. Each of the plurality of sheath lumens 112a, 112b of FIG. 9 is substantially circular-shaped in cross-section and is matched in cross-sectional area with each other of the plurality of sheath lumens 112a, 112b. The inward surface 434 of each of the sheath lumens 112a, 112b of the sheath body 110 of FIG. 9 is only partially defined by the segments 428a, 428b of the septum B 326 when the septum B 326 is in the biased condition.

Figure 10:
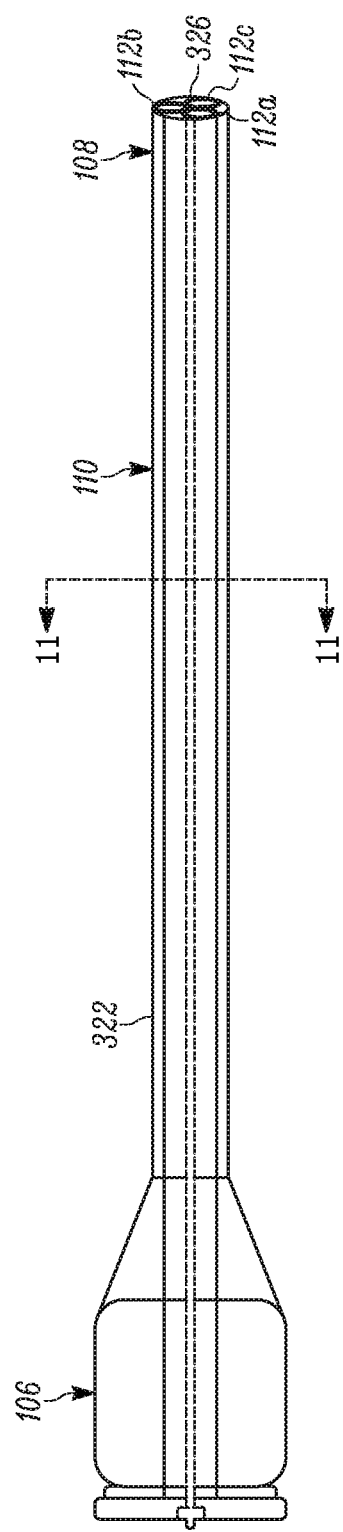
FIG. 10 depicts an element of the aspect of FIG. 3, in an alternate configuration.
Figure 11:
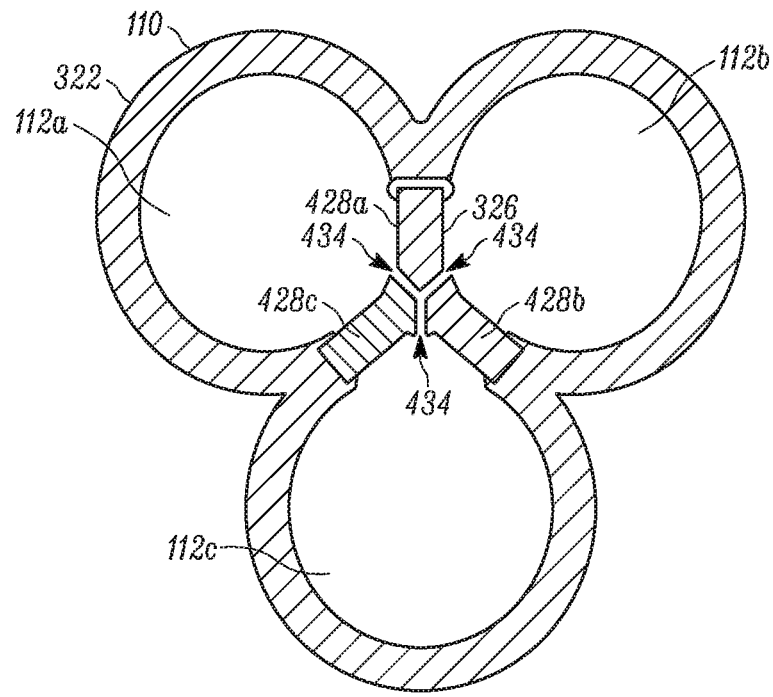
FIG. 11 depicts a cross-sectional view of the aspect of FIG. 10.

In FIGS. 10-11, the sheath body 110 has a symmetrical tri-lobe shape in cross-section to accommodate first, second, and third sheath lumens 112 (shown here as the first, the second, and the third sheath lumens 112a, 112b, 112c). The sheath body 110 of FIGS. 10-11 has rotational symmetry of the order 3. Each of the first, second, and third sheath lumens 112a, 112b, 112c is substantially circular-shaped in cross-section and is matched in cross-sectional area with each other of the first, the second, and the third sheath lumens 112a, 112b, 112c. The inward surface 434 of each of the first, the second, and the third sheath lumens 112a, 112b, 112c of the sheath body 110 of FIGS. 10-11 is only partially defined by at least two of first, second, and third segments 428 (shown here as the first, the second, and the third segments 428a, 428b, 428c) of the septum B 326 when the septum B 326 is in the biased condition.

Figure 12:
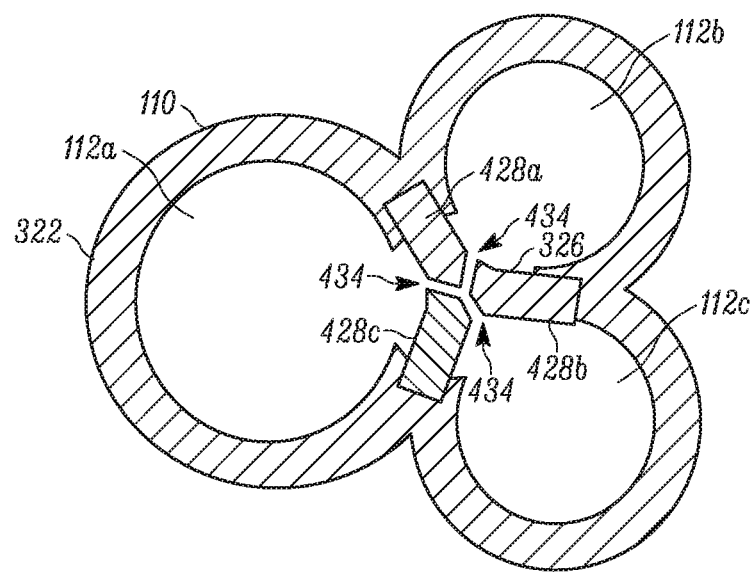
FIGS. 12-14 depict cross-sectional views of an element of the aspect of FIG. 10, in alternate configurations.

In FIG. 12, the sheath body 110 has an asymmetrical tri-lobe shape in cross-section to accommodate the first, the second, and the third sheath lumens 112a, 112b, 112c. The sheath body 110 of FIG. 12 has rotational symmetry of the order 1. Each of the first, the second, and the third sheath lumens 112a, 112b, 112c is substantially circular-shaped in cross-section. At least one of the first, the second, and the third sheath lumens 112a, 112b, 112c is not matched in cross-sectional area with at least one other of the first, the second, and the third sheath lumens 112a, 112b, 112c. The inward surface 434 of each of the first, the second, and the third sheath lumens 112a, 112b, 112c of the sheath body 110 of FIG. 12 is only partially defined by at least two of the first, the second, and the third segments 428a, 428b, 428c of the septum B 326 when the septum B 326 is in the biased condition.

Figure 13:
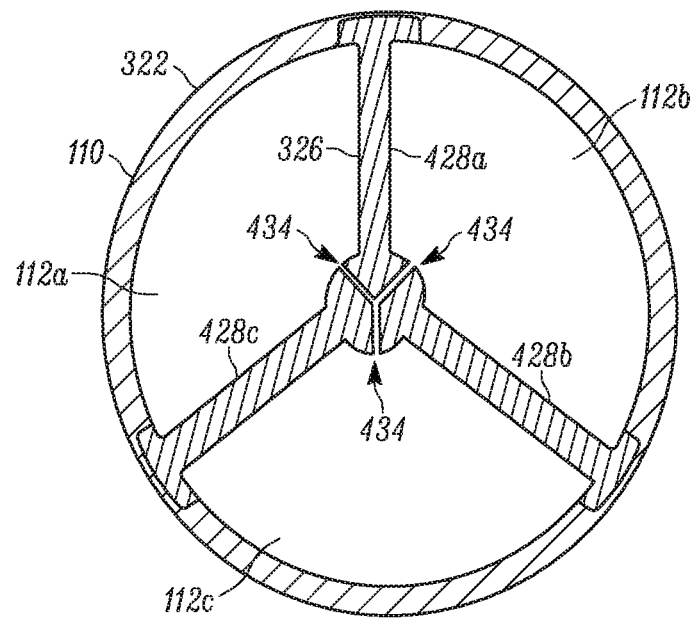

In FIG. 13, the sheath body 110 has a circular shape in cross-section. The sheath body 110 of FIG. 13 has rotational symmetry of the order 3. The introducer sheath B 322 of FIG. 13 has the first, the second, and the third sheath lumens 112a, 112b, 112c that are matched in cross-sectional area with one another. The inward surface 434 of each of the first, the second, and the third sheath lumens 112a, 112b, 112c of FIG. 13 is substantially defined by at least two of the first, the second, and the third segments 428a, 428b, 428c of the septum B 326 when the septum B 326 is in the biased condition.

Figure 14:
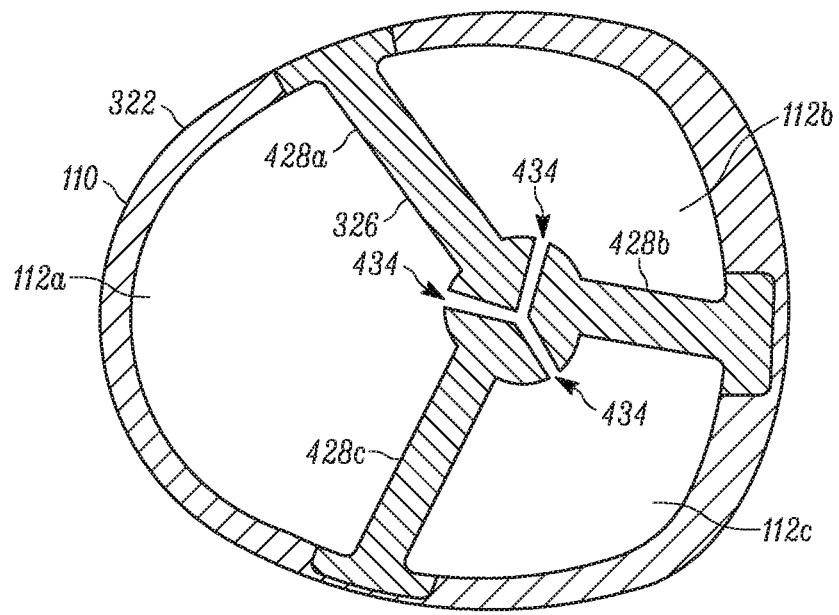
Figure 15:
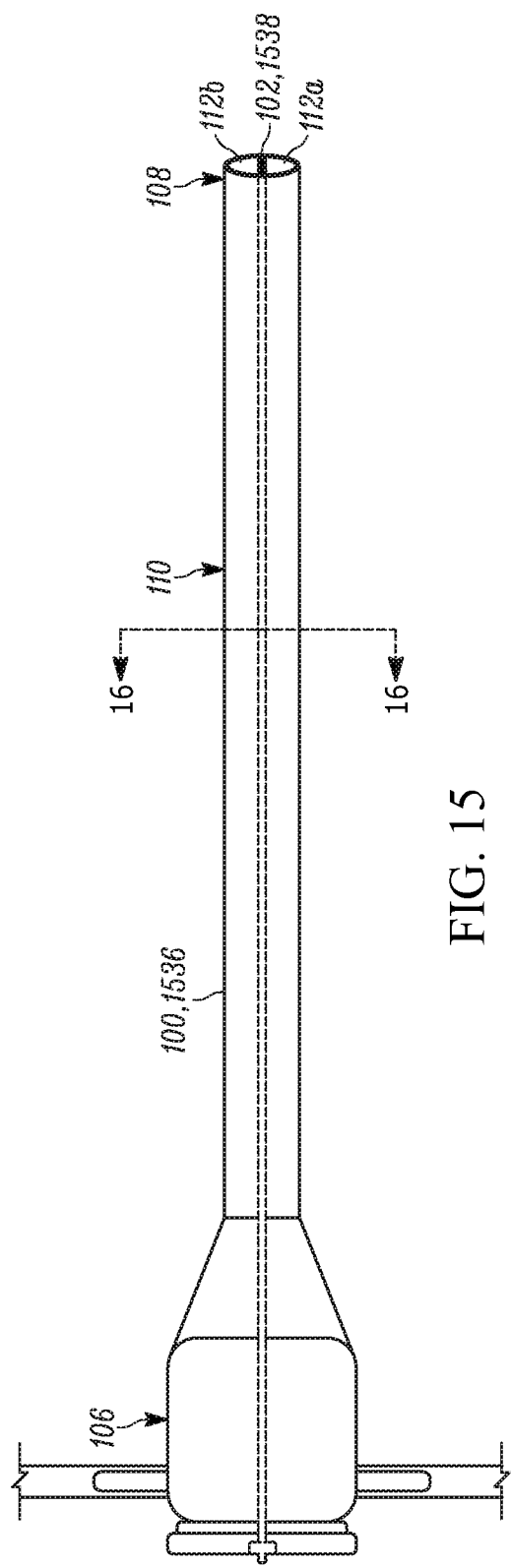
FIG. 15 is a top view of an element of the aspect of FIG. 1, in an alternate configuration.

In FIG. 14, the sheath body 110 is asymmetrically ovate, or, in other words, egg-shaped, in cross-section. The sheath body 110 of FIG. 14 has rotational symmetry of the order 1. The introducer sheath B 322 of FIG. 14 has the first, the second, and the third sheath lumens 112a, 112b, 112c. At least one of the first, the second, and the third sheath lumens 112a, 112b, 112c shown in FIG. 14 is larger than the other of the first, the second, and the third sheath lumens 112a, 112b, 112c. Thus, at least one of the first, the second, and the third sheath lumens 112a, 112b, 112c is not matched in cross-sectional area with each other of the first, the second, and the third sheath lumens 112a, 112b, 112c. The inward surface 434 of each of the sheath lumens 112a, 112b, 112c of FIG. 14 is substantially defined by the first, the second, and the third segments 428a, 428b, 428c of the septum B 326 when the septum B 326 is in the biased condition.

Although only the introducer sheath B 322 has been shown as having the various configurations discussed above, any of alternate configurations of the introducer sheath 100 may have any of the various configurations discussed above.

Figure 16:
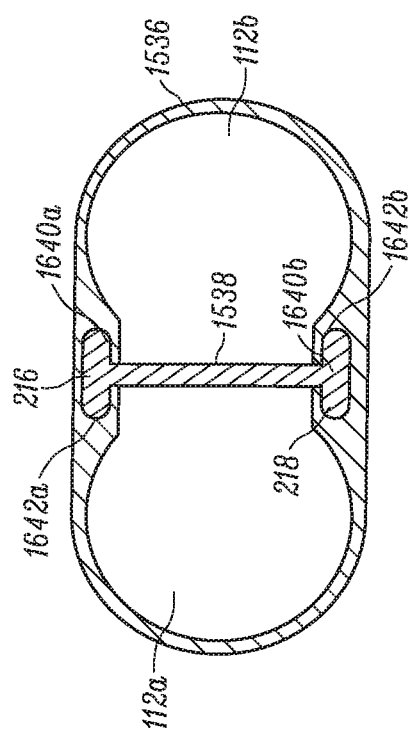
FIG. 16 depicts a cross-sectional view of the aspect of FIG. 15.
Figure 17:
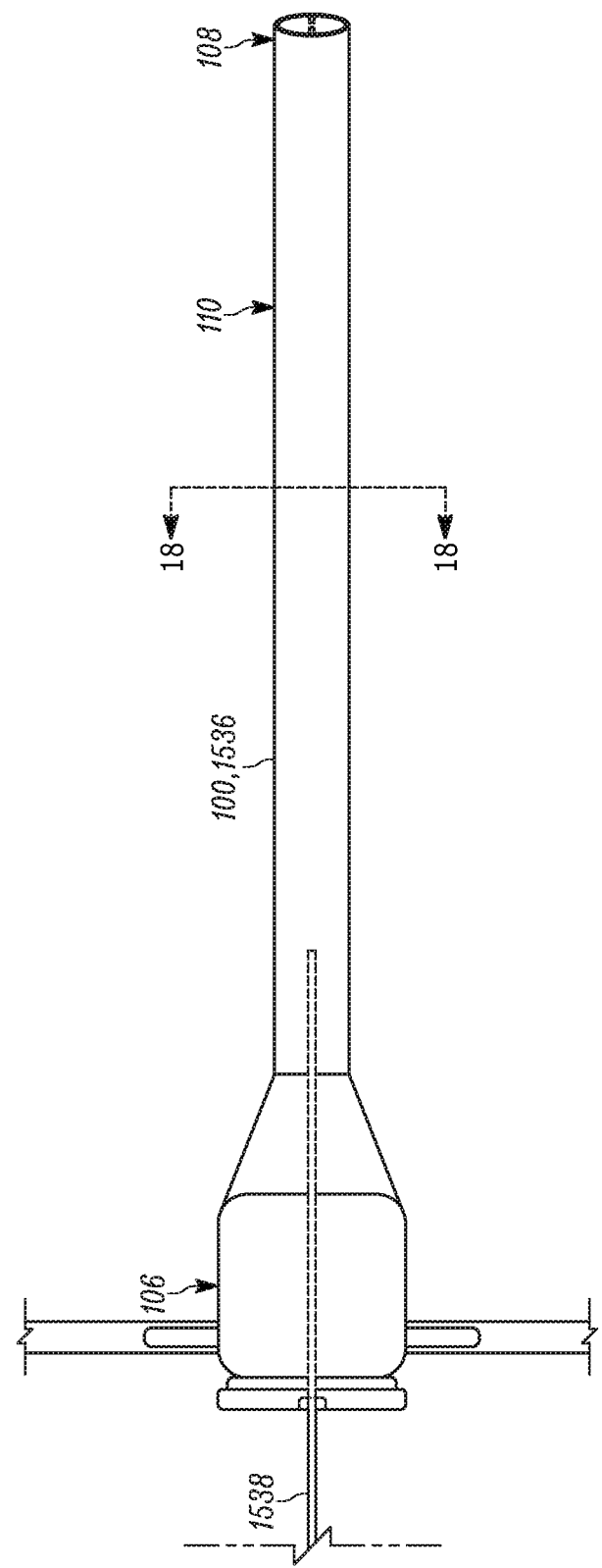
FIG. 17 is a top view of the aspect of FIG. 15, in an example use configuration.
Figure 18:
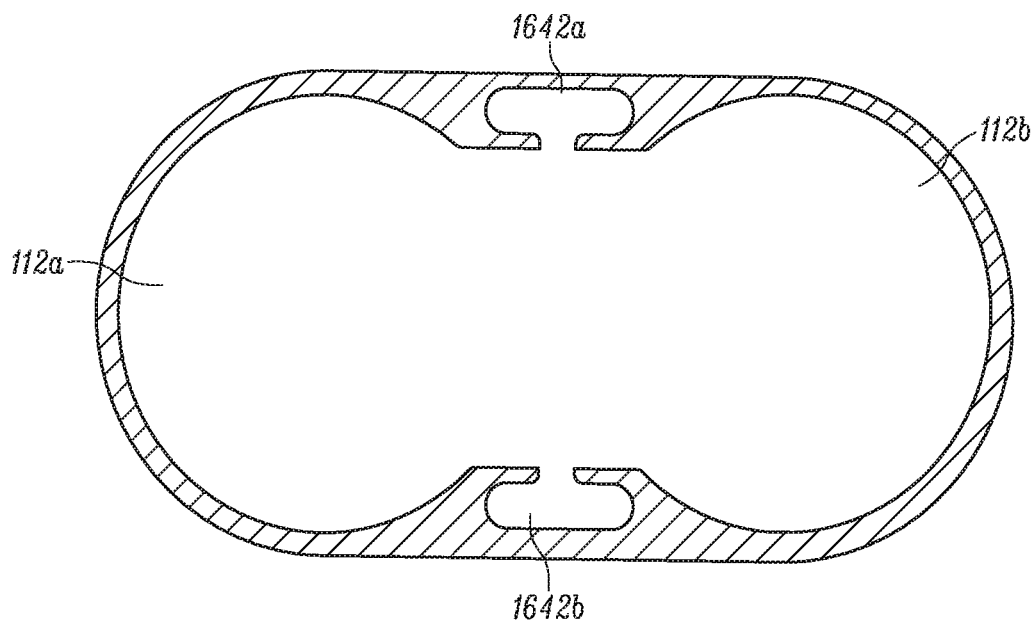
FIG. 18 depicts a cross-sectional view of the aspect of FIG. 17.

FIGS. 15-18 depict an example alternate configuration for the introducer sheath 100, referred to as an introducer sheath C 1536. The introducer sheath C 1536 includes an example configuration of the septum 102, referred to as a septum C 1538. The septum C 1538 is selectively removable from the introducer sheath C 1536, and thus the septum C 1538 may be alternatively referred to herein as the removable septum C 1538 and/or the removable septum 1538. In particular, as shown in FIG. 16, the septum C 1538 includes lands 1640 (shown here as the lands 1640*a* and 1640*b*) at each of the first and second ends 216, 218 of the septum C 1538. Each of the lands 1640*a*, 1640*b* corresponds to a track 1642 (shown here as the tracks 1642*a* and 1642*b*) in the introducer sheath C 1536 so that the septum C 1538 may be inserted and removed from the introducer sheath C 1536 along the tracks 1642*a*, 1642*b*. When the removable septum C 1538 is inserted into the introducer sheath C 1536, the removable septum C 1538 extends between the sheath proximal and distal ends 106, 108 and selectively separates each of the plurality of sheath lumens 112*a*, 112*b* from one another to at least partially isolate each of plurality of sheath lumens 112*a*, 112*b* from one another. As shown in FIGS. 17-18, when the removable septum C 1538 is at least partially selectively removed from the introducer sheath C 1536, at least one of the plurality of sheath lumens 112*a*, 112*b* is in fluid communication with at least one other of the plurality of sheath lumens 112*a*, 112*b*.

Figure 19:
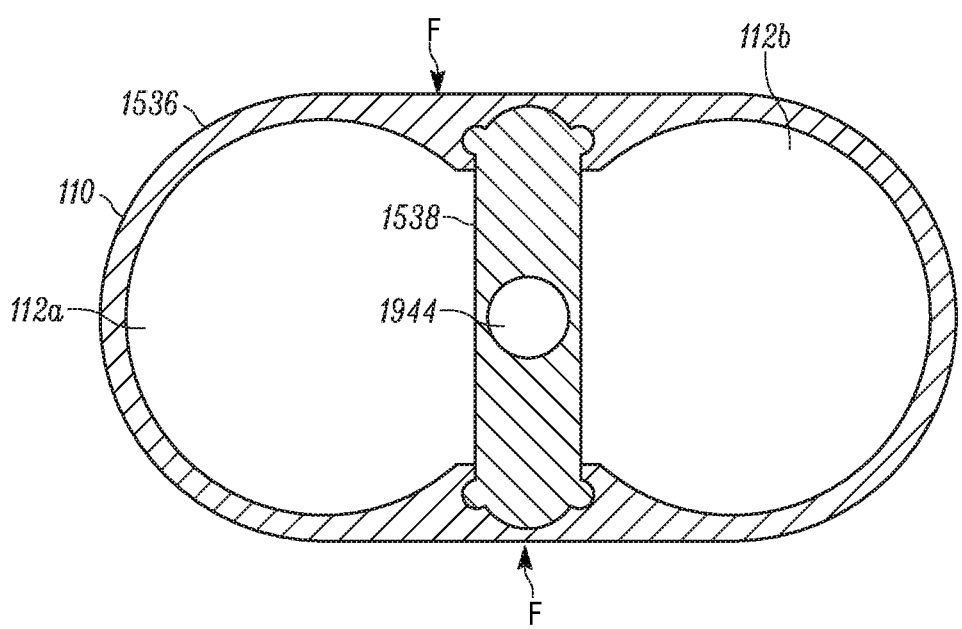
FIGS. 19-20 depict cross-sectional views of an element of the aspect of FIG. 15, in alternate configurations.
Figure 20:
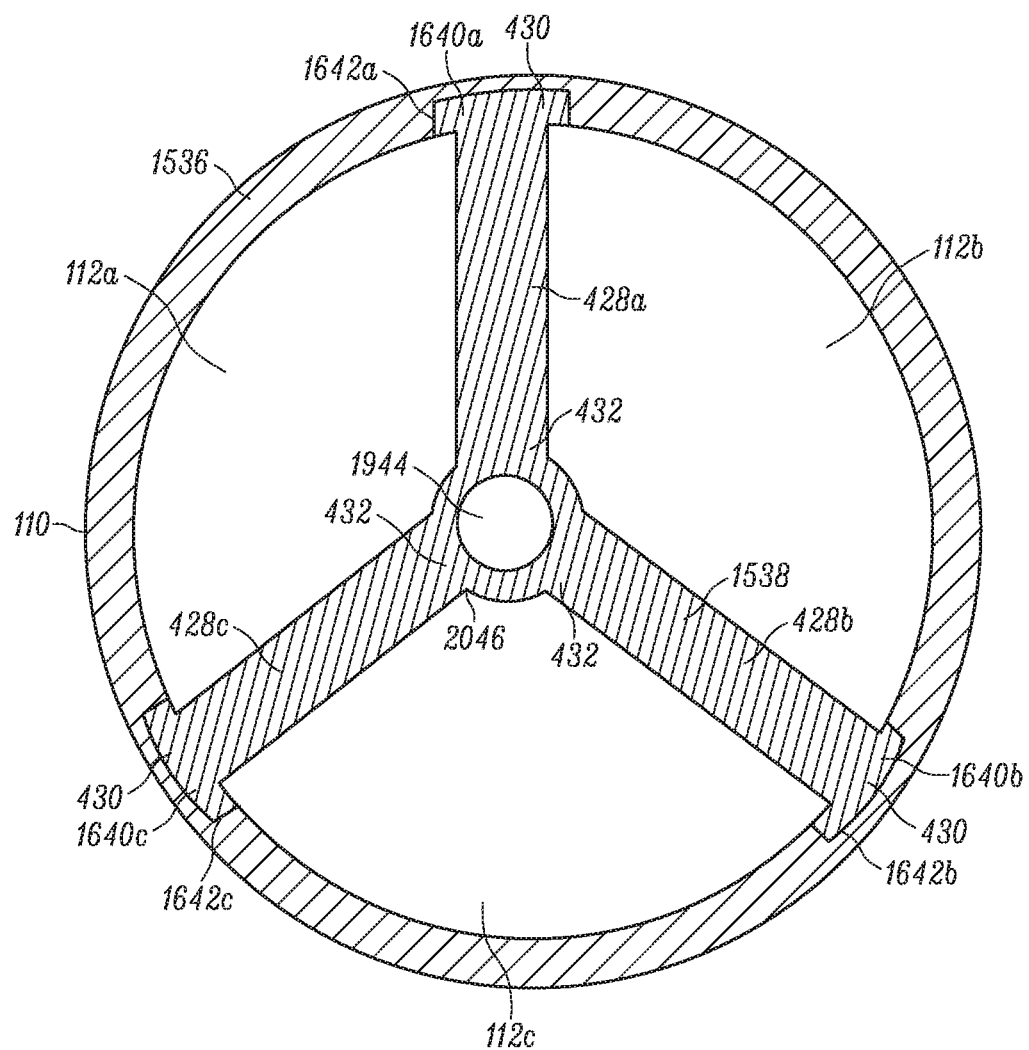

FIGS. 19-20 depict alternate configurations of certain portions of the introducer sheath C 1536. In FIG. 19, the sheath body 110 is stadium-shaped in cross-section, with two substantially flat opposing sides F. The sheath body 110 of FIG. 19 has rotational symmetry of the order 2. The septum C 1538 of the introducer sheath C 1536 of FIG. 19 includes a guidewire passage 1944 longitudinally extending therethrough so that the introducer sheath C 1536 may be inserted along a guidewire G through the guidewire passage 1944 in the septum C 1538.

In FIG. 20, the sheath body 110 may be circular-shaped in cross-section and the septum C 1538 may have first, second, and third segments 428 (shown here as the first, the second, and the third segments 428*a*, 428*b*, 428*c*). The sheath body 110 of FIG. 20 has rotational symmetry of the order 3. Each of the first, the second, and the third segments 428*a*, 428*b*, 428*c* has a segment first end 430 and a segment second end 432. Each of the first segment ends 430 has a land 1640 (shown here as the lands 1640*a*, 1640*b*, and 1640*c*) that corresponds to a track 1642 (shown here as the tracks 1642*a*, 1642*b*, and 1642*c*) in the introducer sheath C 1536 of FIG. 20. Each of the second segments ends 432 are attached to each other at a central portion 2046 of the septum C 1538. The central portion 2046 of the septum C 1538 of FIG. 20 may have a guidewire passage 1944. Although only the introducer sheath C 1536 has been shown as having the various configurations discussed above, any of alternate configurations of the introducer sheath 100 may have any of the various configurations discussed above.

Figure 21:
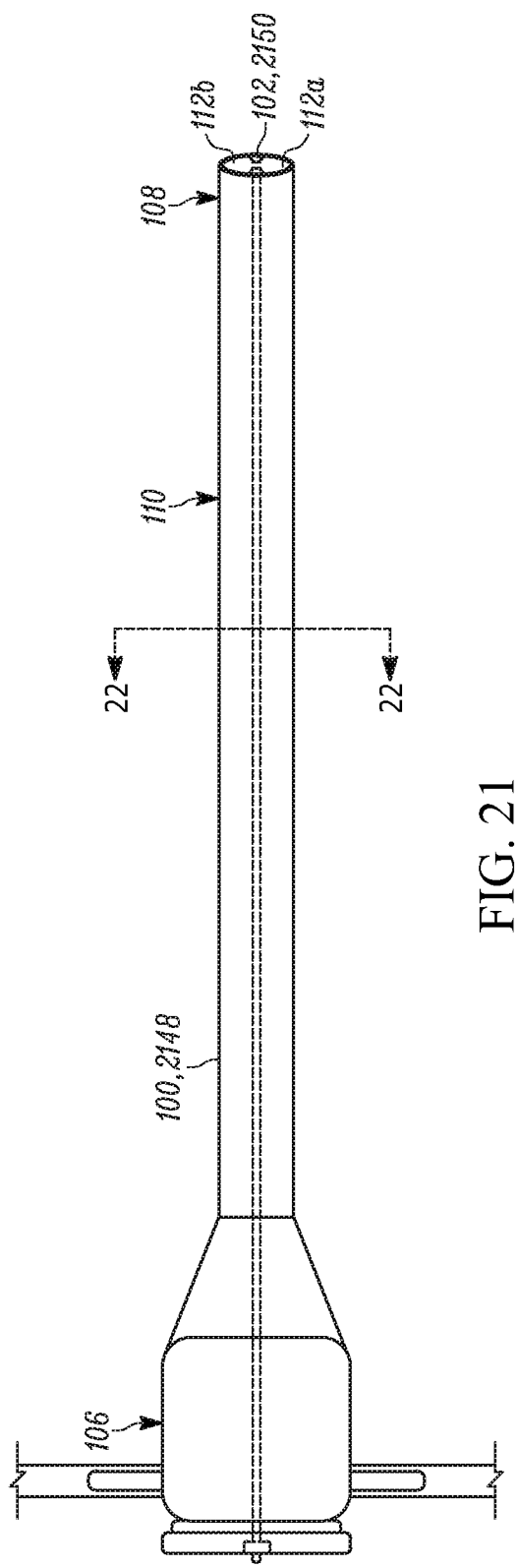
FIG. 21 is a top view of an element of the aspect of FIG. 1, in an alternate configuration.
Figure 22:
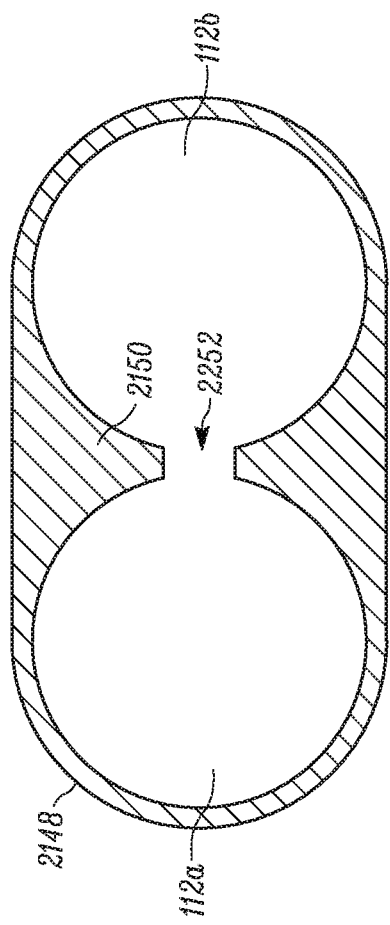
FIG. 22 depicts a cross-sectional view of the aspect of FIG. 21.

FIGS. 21-22 depict an example alternate configuration for the introducer sheath 100, referred to as an introducer sheath D 2148. The introducer sheath D 2148 includes an example configuration of the septum 104, referred to as a septum D 2150. As shown in FIG. 22, the septum D 2150 has an opening 2252 extending between each of the plurality of sheath lumens 112 (shown here as the sheath lumens 112*a* and 112*b*) so that each of the plurality of sheath lumens 112*a*, 122*b* is in constant fluid communication with each other of the plurality of sheath lumens 112*a*, 112*b*.

Figure 23:
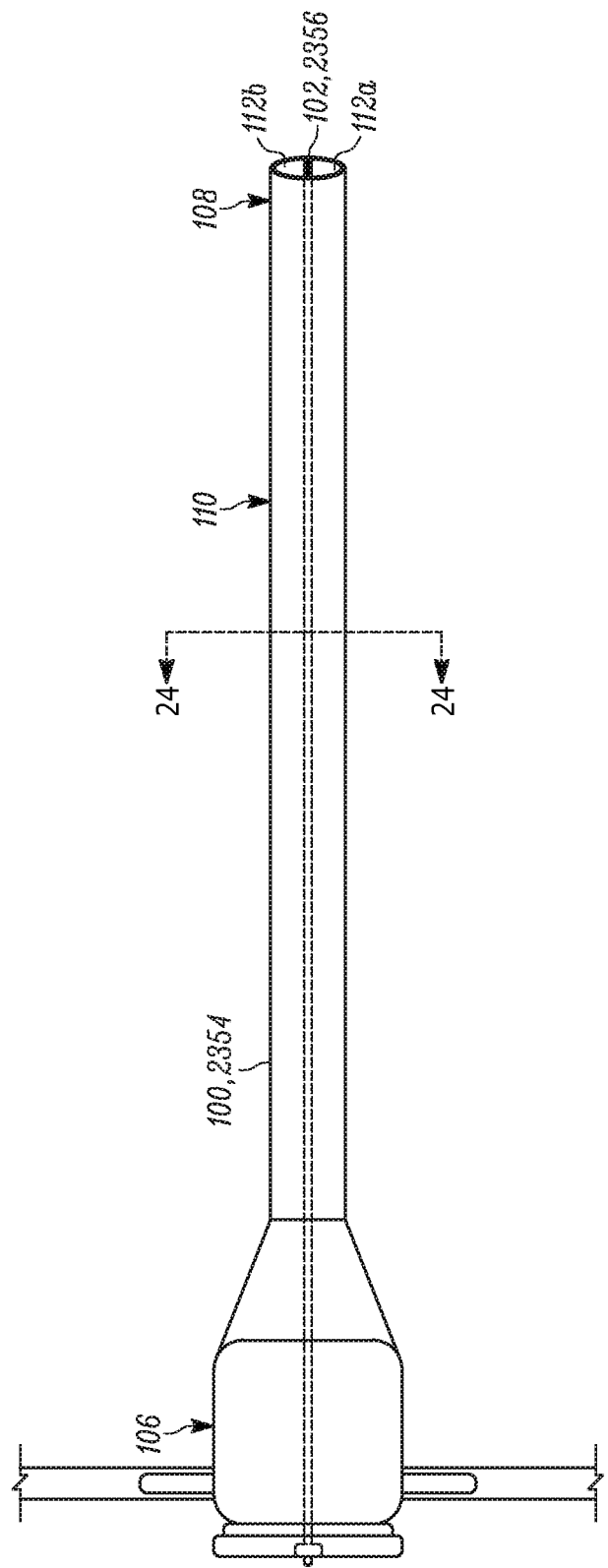
FIG. 23 is a top view of an element of the aspect of FIG. 1, in an alternate configuration.
Figure 24:
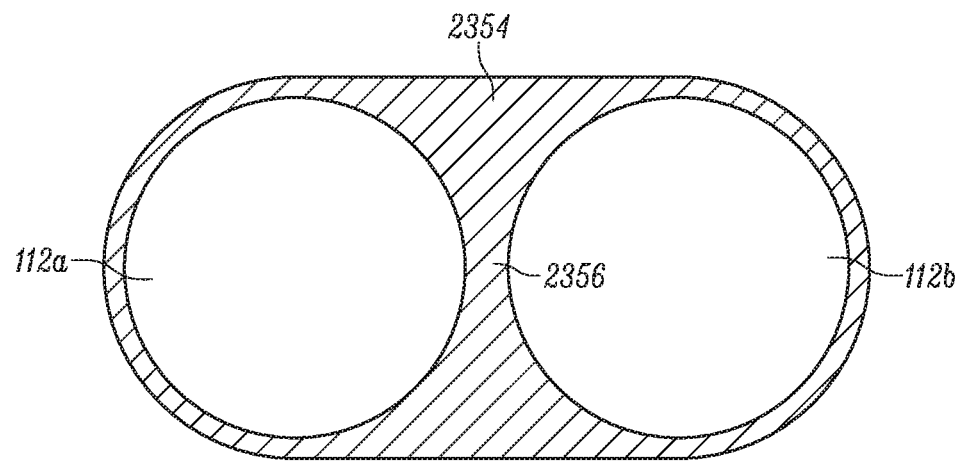
FIG. 24 depicts a cross-sectional view of the aspect of FIG. 23.

FIGS. 23-24 depict an example alternate configuration for the introducer sheath 100, referred to as an introducer sheath E 2354. The introducer sheath E includes an example configuration of the septum 104, referred to as a septum E 2356. As shown in FIG. 24, the septum E 2356 does not permit fluid communication between each of the plurality of sheath lumens 112 (shown here as the sheath lumens 112*a* and 112*b*) so that each of the plurality of sheath lumens 112*a*, 112*b* are isolated from one another.

Figure 25:
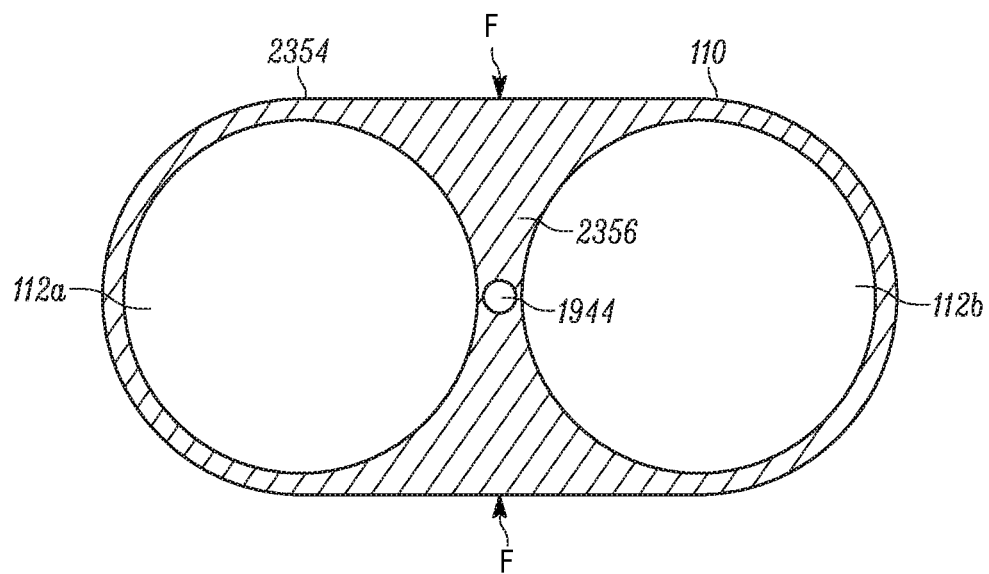
FIGS. 25-29 depict cross-sectional views of an element of the aspect of FIG. 23, in alternate configurations.
Figure 26:
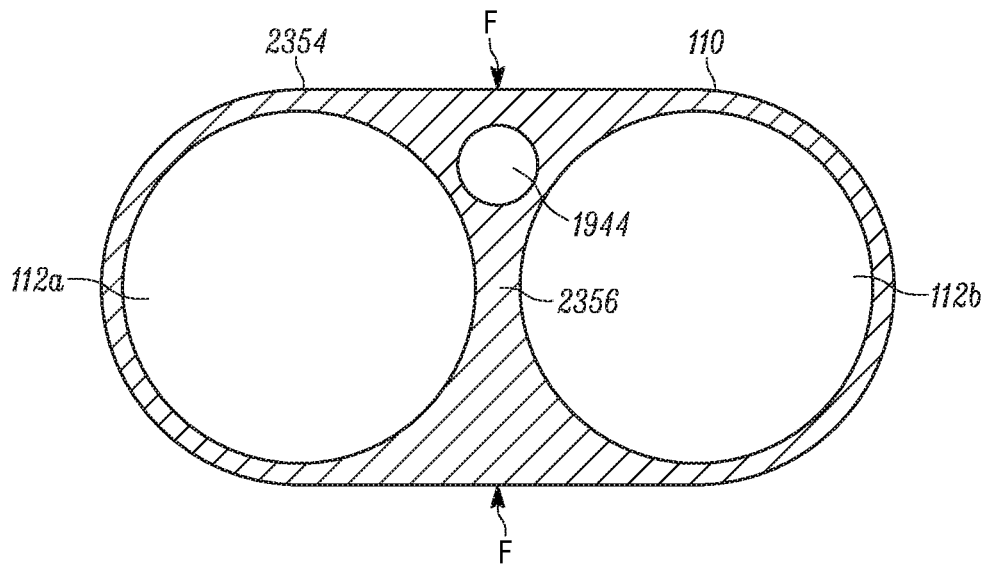

FIGS. 25-31 depict alternate configurations of certain portions of the introducer sheath E 2354. In FIG. 25, the sheath body 110 is stadium-shaped in cross-section, with two substantially flat opposing sides F. The sheath body 110 of FIG. 25 has rotational symmetry of the order 2. The septum E 2356 of the introducer sheath E 2354 of FIG. 25 has a guidewire passage 1944 longitudinally extending therethrough. The guidewire passage 1944 of the septum E 2356 of FIG. 25 is centrally located in the septum E 2356. In FIG. 26, the septum E 2356 has the guidewire passage 1944 located near one lateral end of the septum E 2356 instead of being centrally located.

Figure 27:
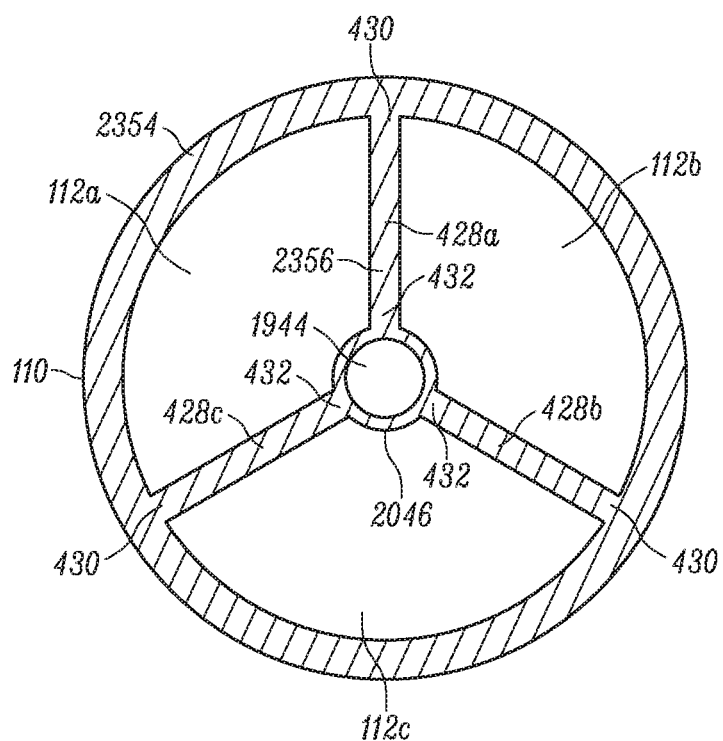

In FIG. 27, the sheath body 110 may be circular shaped in cross-section and the septum E 2356 may have first, second, and third segments 428 (shown here as the first, the second, and the third segments 428*a*, 428*b*, 428*c*). The sheath body 110 of FIG. 27 has rotational symmetry of the order 3. Each of the first, the second, and the third segments 428*a*, 428*b*, 428*c* has a first segment end 430 and a second segment end 432. Each of the first segment ends 430 is attached to the interior wall 220 of the introducer sheath E 2354. Each of the second segments ends 432 are attached to each other at a central portion 2046 of the septum E 2354. The central portion 2046 of the septum E 2354 of FIG. 27 may have the guidewire passage 1944.

Figure 28:
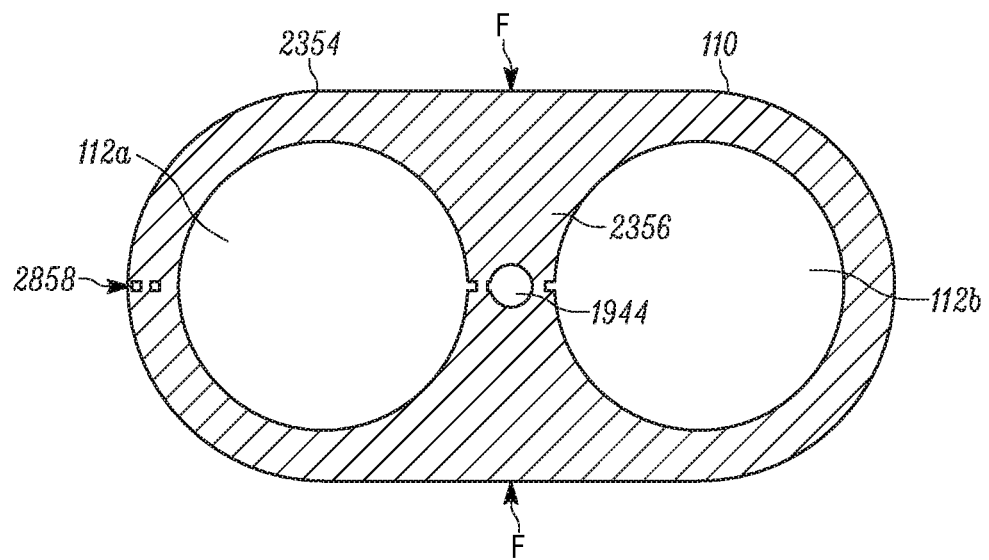
Figure 29:
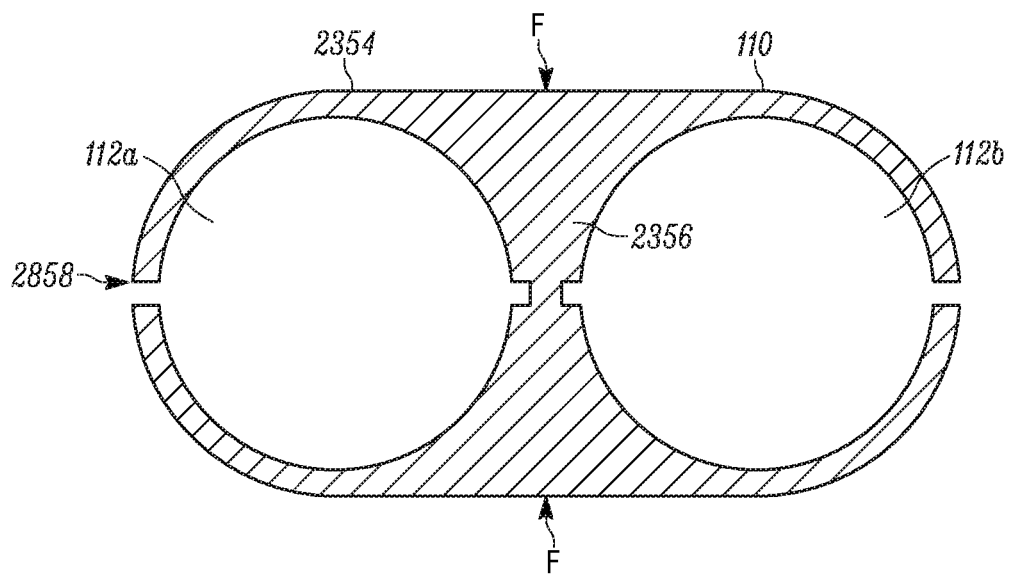

In FIG. 28, the sheath body 110 is stadium-shaped in cross-section, with two substantially flat opposing sides F. The sheath body 110 of FIG. 28 has rotational symmetry of the order 2. The septum E 2356 of the introducer sheath E 2354 of FIG. 28 has the guidewire passage 1944 longitudinally extending therethrough. The introducer sheath E 2354 of FIG. 28 is configured so that at least a portion of the introducer sheath E 2354 may be at least partially frangibly separated from another portion of the introducer sheath E 2354. In particular, the introducer sheath E 2354 of FIG. 28 may have perforations 2858 that at least partially laterally extend through the introducer sheath E 2354. A user may apply pressure to at least partially separate at least a portion of the introducer sheath E 2354 from another portion of the introducer sheath E 2354 along the perforations 2858, and thus at least partially tear-open the introducer sheath E 2354 of FIG. 28 at the perforations 2858. This allows a user to insert at least one medical instrument 3360 through at least one of the plurality of sheath lumens 112 (shown here as the sheath lumens 112*a* and 112*b*) and then remove the introducer sheath E 2354 of FIG. 28 from around the at least one medical instrument by tearing open the introducer sheath E 2354 to leave the medical instrument 3360 in place. The introducer sheath E 2354 of FIG. 29 is substantially similar to the introducer sheath E 2354 of FIG. 28 except that the introducer sheath E 2354 of FIG. 29 does not include the guidewire passage 1944.

Figure 30:
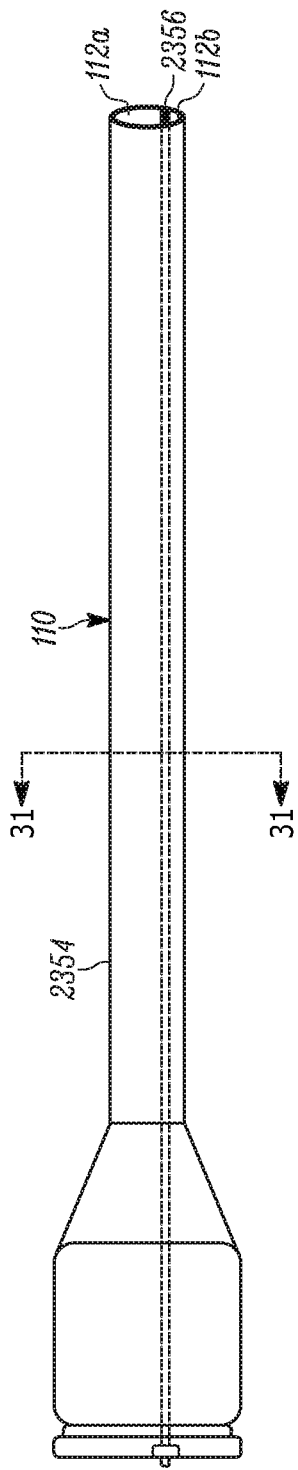
FIG. 30 depicts a top view of an element of the aspect of FIG. 23, in an alternate configuration.
Figure 31:
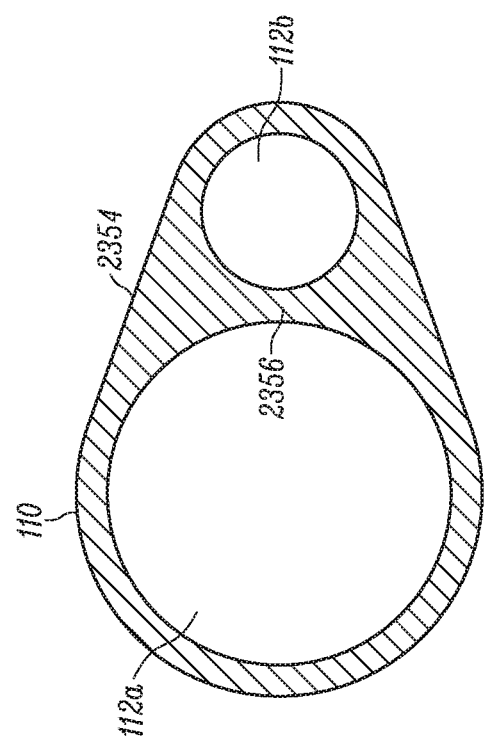
FIG. 31 depicts a cross-sectional view of the aspect of FIG. 30.

In FIGS. 30-31, the sheath body 110 is asymmetrically ovate, or, in other words egg-shaped, in cross-section. The sheath body 110 of FIGS. 30-31 has rotational symmetry of the order 1. At least one of the plurality of sheath lumens 112 (shown here as the sheath lumens 112*a* and 112*b*) shown in FIG. 30 is larger than the other of the plurality of sheath lumens 112a, 112b. Thus, at least one of the plurality of sheath lumens 112a, 112b is not matched in cross-sectional area with each other of the plurality of sheath lumens 112a, 112b. Although only the introducer sheath E 2354 has been shown as having the various configurations discussed above, any of alternate configurations of the introducer sheath 100 may have any of the various configurations discussed above.

Certain example configurations of the introducer sheath 100 permit the transition of a guidewire G between at least one of the plurality of sheath lumens 112 and another one of the plurality of sheath lumens 112. For the sake of brevity, not every introducer sheath configuration is discussed and/or depicted in the following description. However, it is to be understood that the following descriptions may be applicable to certain alternate configurations of the introducer sheath 100, as described above.

Figure 32:
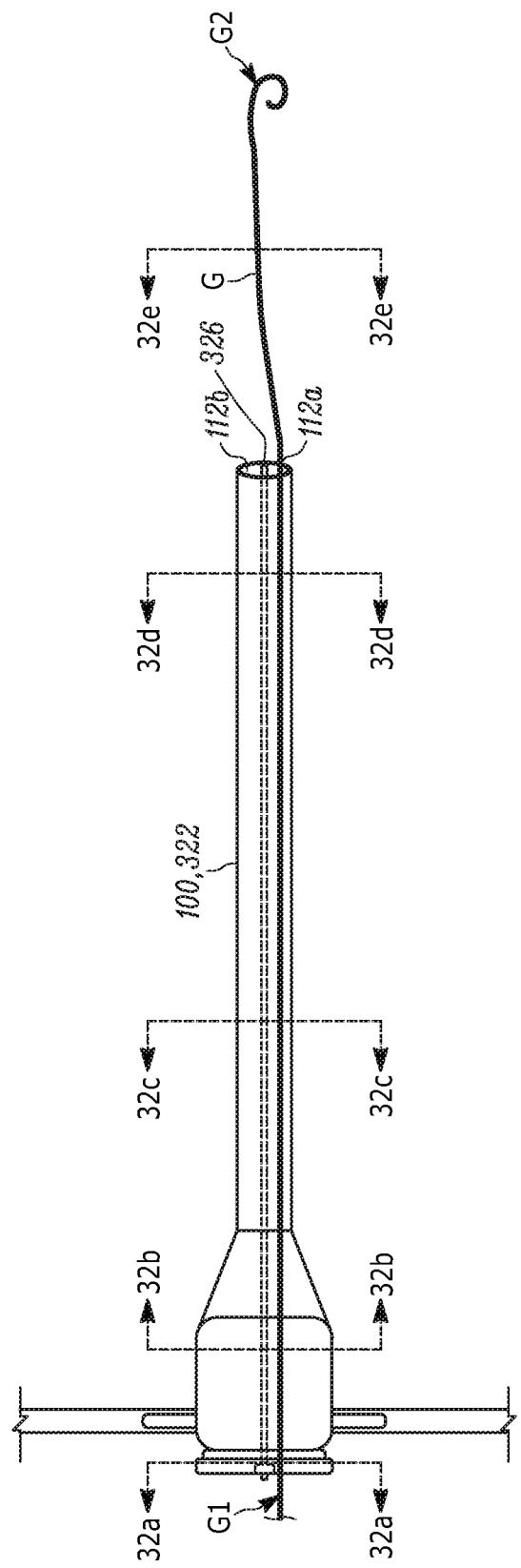
FIGS. 32-35e illustrate an example sequence of operation of a portion of the aspect of FIG. 3, including cross-sectional views.
Figure 32A:
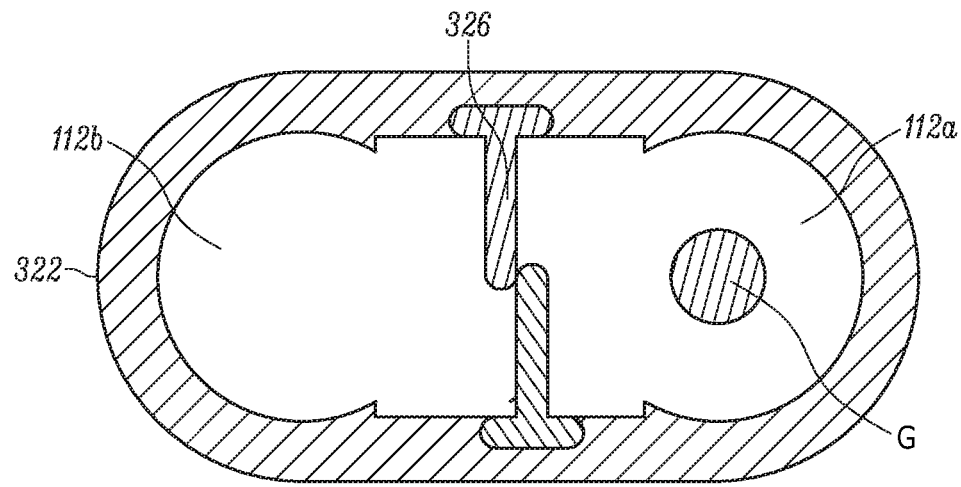
Figure 32B:
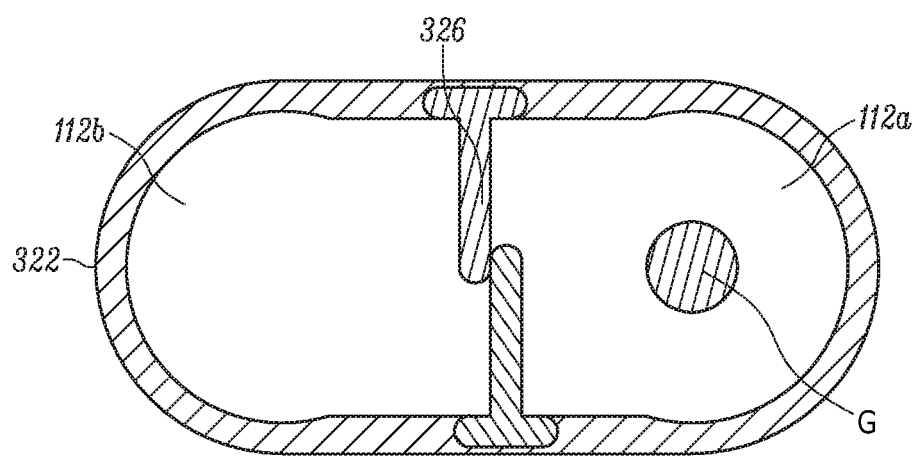
Figure 32C:
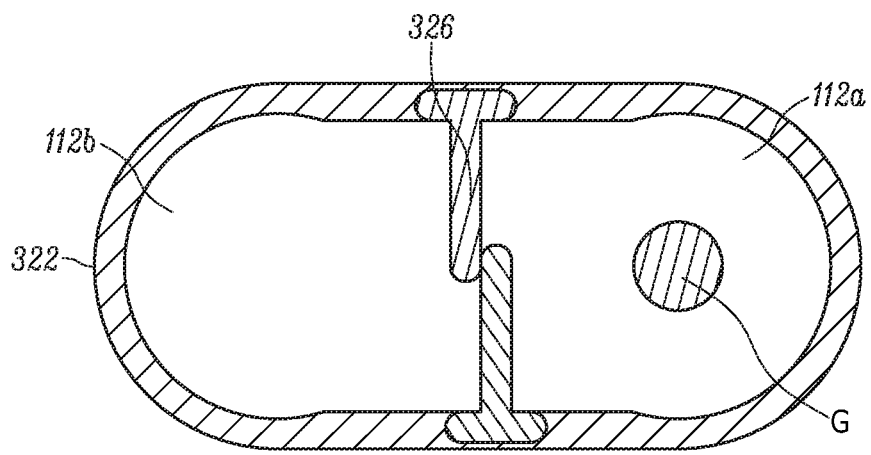
Figure 32D:
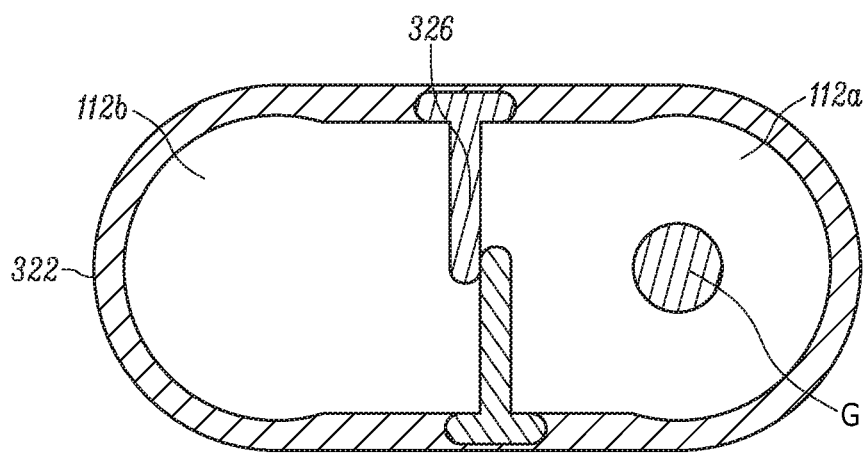
Figure 32E:
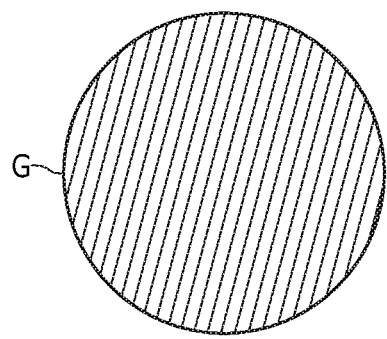
Figure 33:
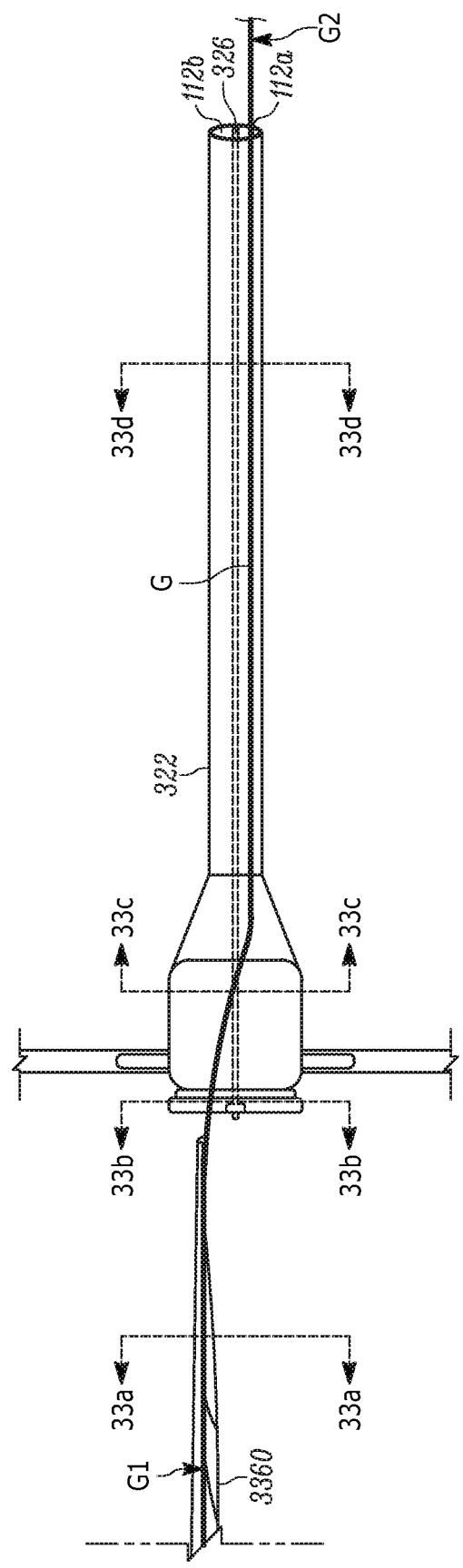
Figure 33A:
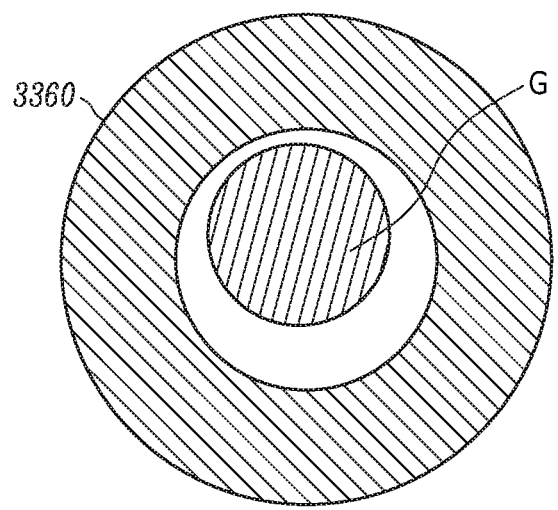
Figure 33B:
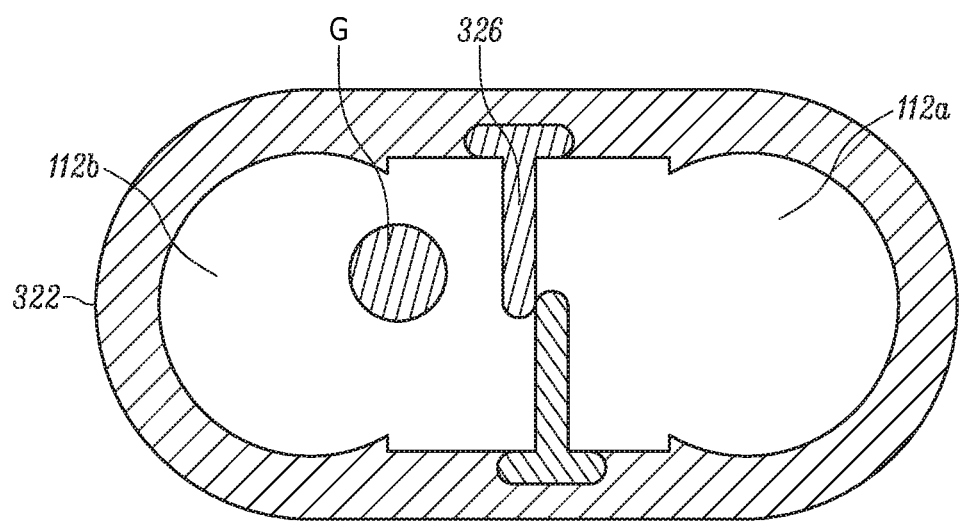
Figure 33C:
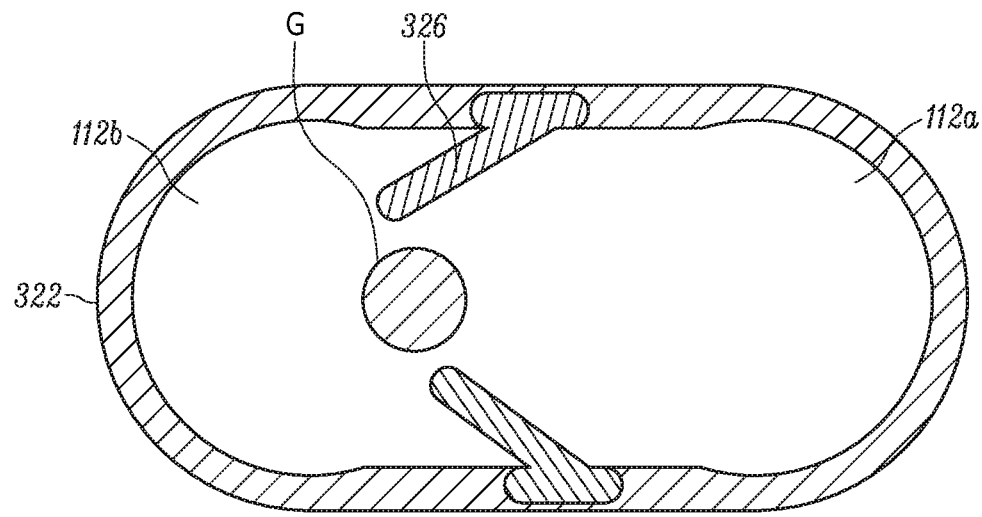
Figure 33D:
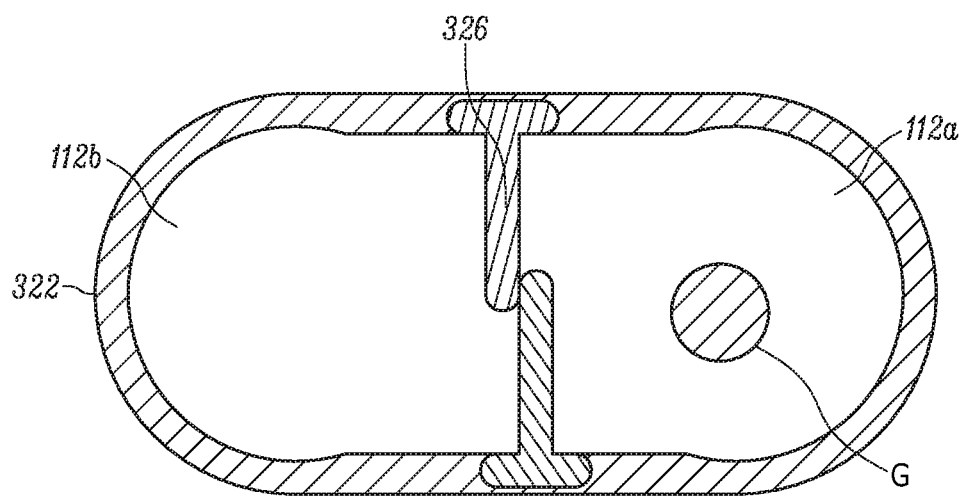

FIGS. 32-35e depict an example transition sequence of a guidewire G from at least one of the plurality of sheath lumens 112 (shown here as the sheath lumens 112a and 112b) to at least one other of the plurality of sheath lumens 112a, 112b in the introducer sheath B 322. As shown in FIG. 32, a guidewire proximal end G1 is directed through a first sheath lumen 112 (shown here as the first sheath lumen 112a) of the plurality of sheath lumens 112a, 112b. FIGS. 32a-e depict cross-sectional views of various points along the introducer sheath B 322, to show the arrangement of the introducer sheath B 322, the septum B 326, and the guidewire G in FIG. 32. As shown in FIG. 33, the guidewire proximal end G1 is directed at least partially through a medical instrument 3360. FIGS. 33a-d depict cross-sectional views of various points along the introducer sheath B 322 and the medical instrument 3360, to show the arrangement of the introducer sheath B 322, the septum B 326, the guidewire G, and the medical instrument 3360 in FIG. 33.

Figure 34:
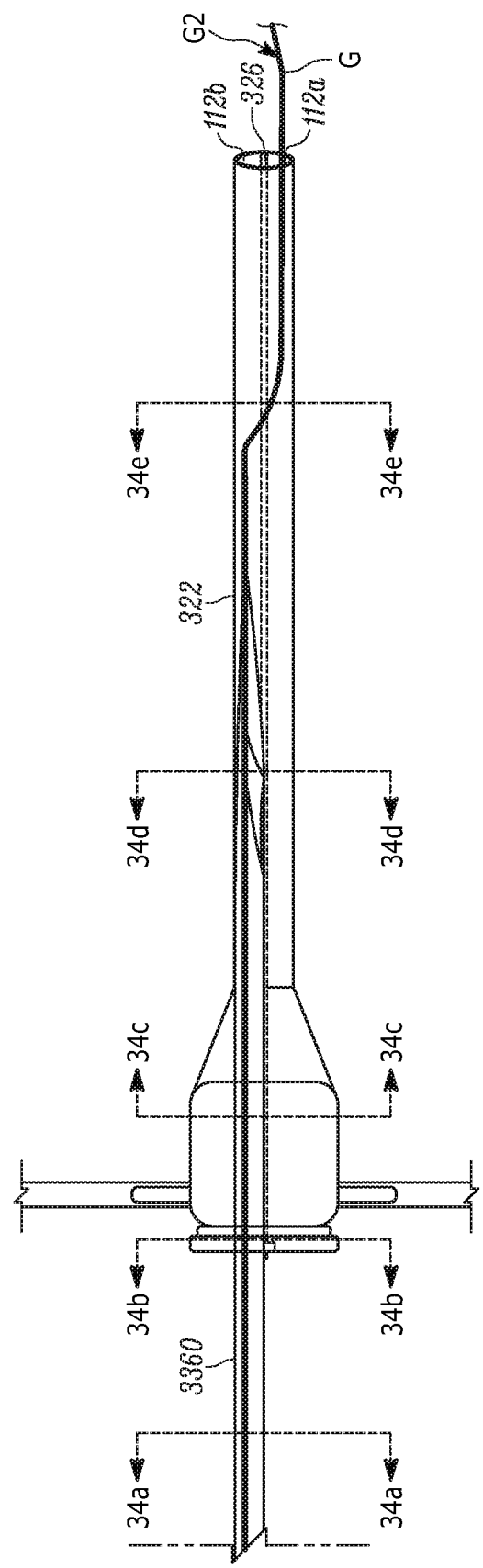
Figure 34A:
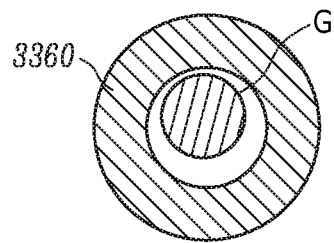
Figure 34B:
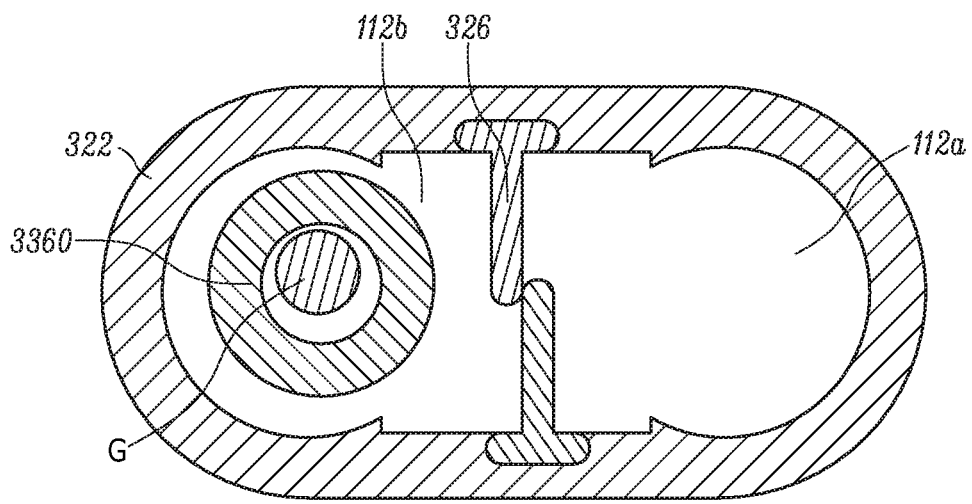
Figure 34C:
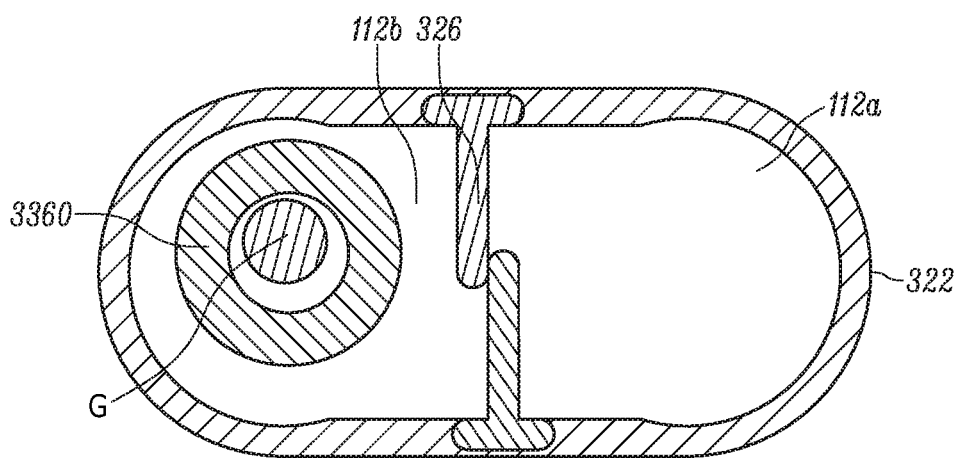
Figure 34D:
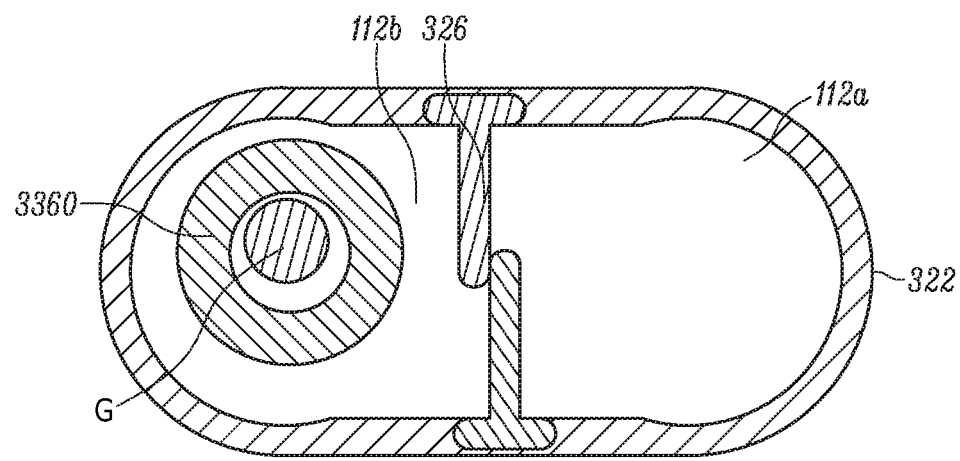
Figure 34E:
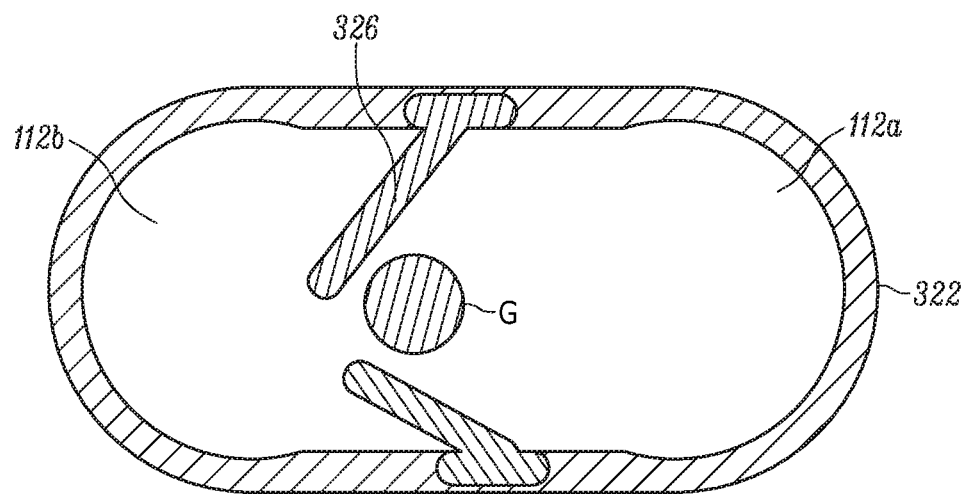
Figure 35:
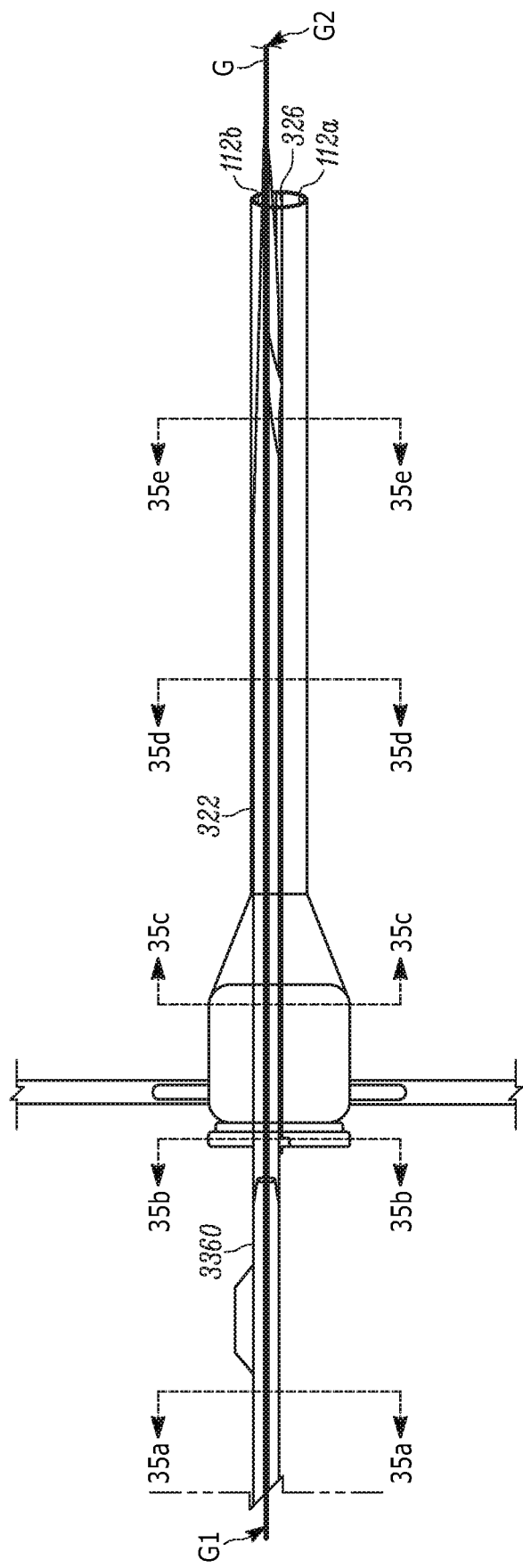
Figure 35A:
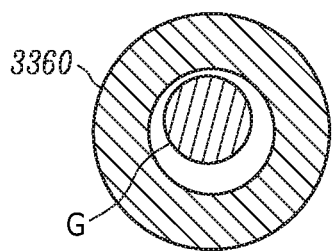
Figure 35B:
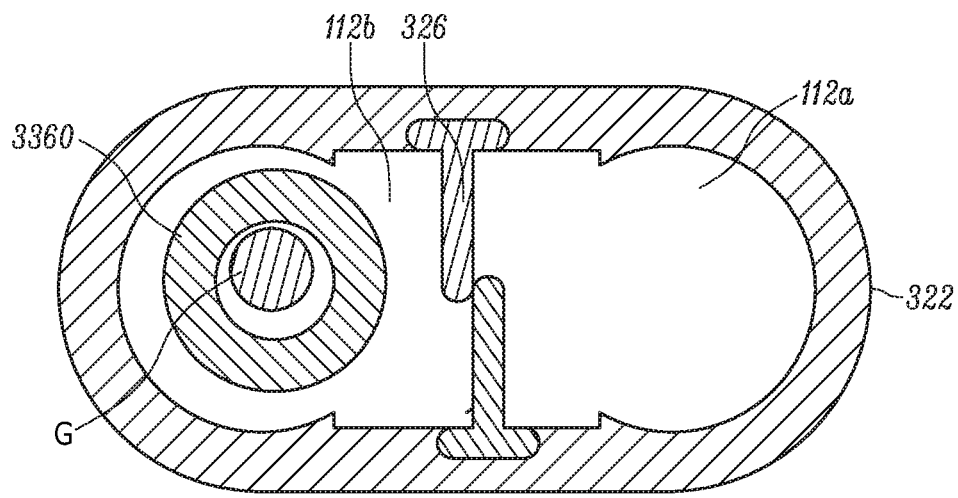
Figure 35C:
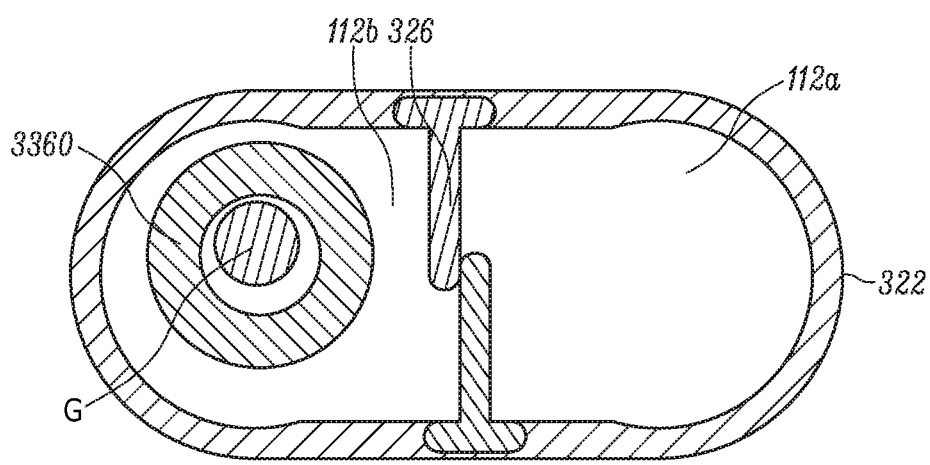
Figure 35D:
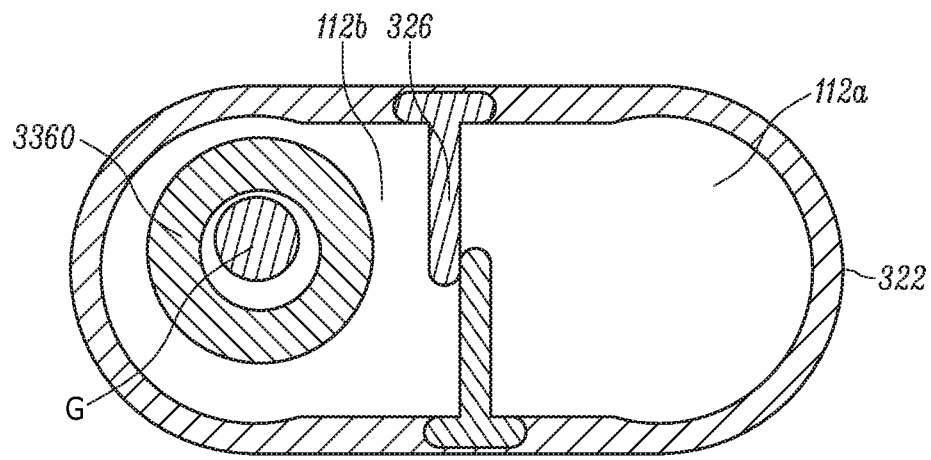
Figure 35E:
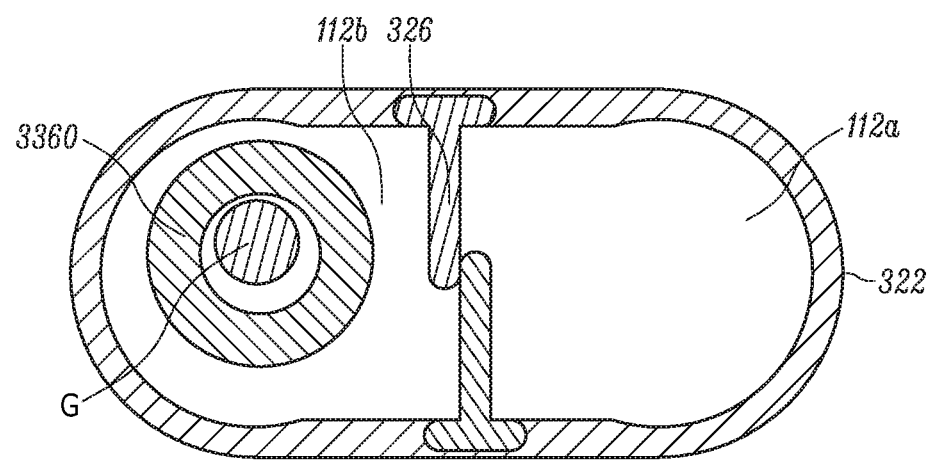

As shown in FIGS. 34-35, the medical instrument 3360 is directed along the guidewire G and at least partially through a second sheath lumen 112 (shown here as the second sheath lumen 112b) of the plurality of sheath lumens 112a, 112b. The medical instrument 3360 urges the guidewire G from the first sheath lumen 112a to the second sheath lumen 112b as the medical instrument 3360 moves at least partially through the second sheath lumen 112b. In particular, the medical instrument 3360 urges the guidewire G from the first sheath lumen 112a to the second sheath lumen 112b by causing at least a portion of the guidewire G to be urged into at least a portion of the septum B 326 to selectively deflect at least a portion of the septum B 326 from the biased condition to the opened condition. The deflection of the septum B 326 at least partially provides fluid communication between the first and second sheath lumens 112a, 112b so that the portion of the guidewire G being urged into the septum B 326 passes into the second sheath lumen 112b from the first sheath lumen 112a. FIGS. 34a-e depict cross-sectional views of various points along the introducer sheath B 322 and the medical instrument 3360, to show the arrangement of the introducer sheath B 322, the septum B 326, and the guidewire G, and the medical instrument 3360 in FIG. 34. FIGS. 35a-e depict cross-sectional views of various points along the introducer sheath B 322 and the medical instrument 3360, to show the arrangement of the introducer sheath B 322, the septum B 326, the guidewire G, and the medical instrument G in FIG. 35.

Figure 36:
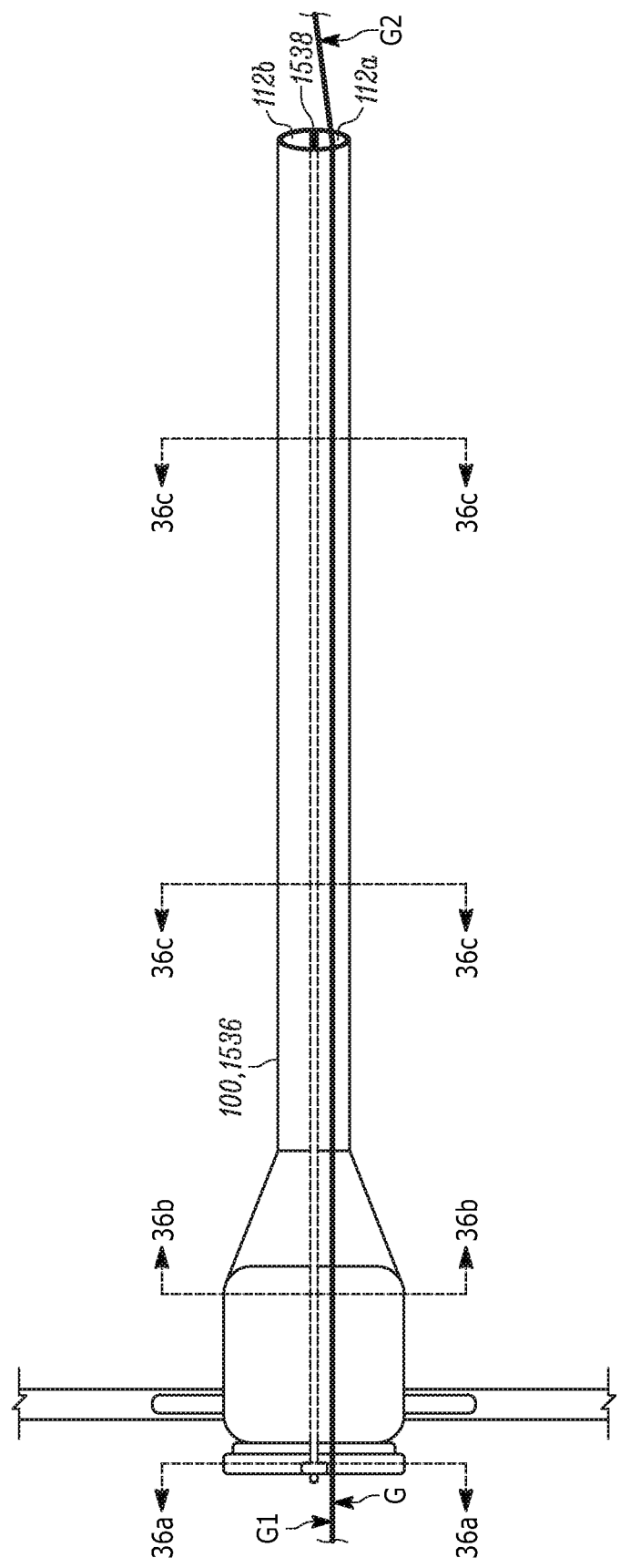
FIGS. 36-41d illustrate an example sequence of operation of a portion of the aspect of FIG. 15, including cross-sectional views.
Figure 36A:
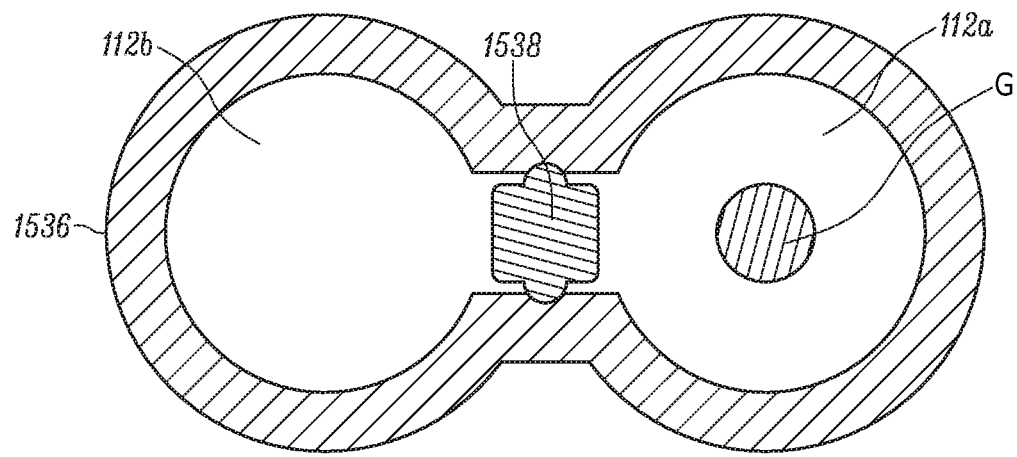
Figure 36B:
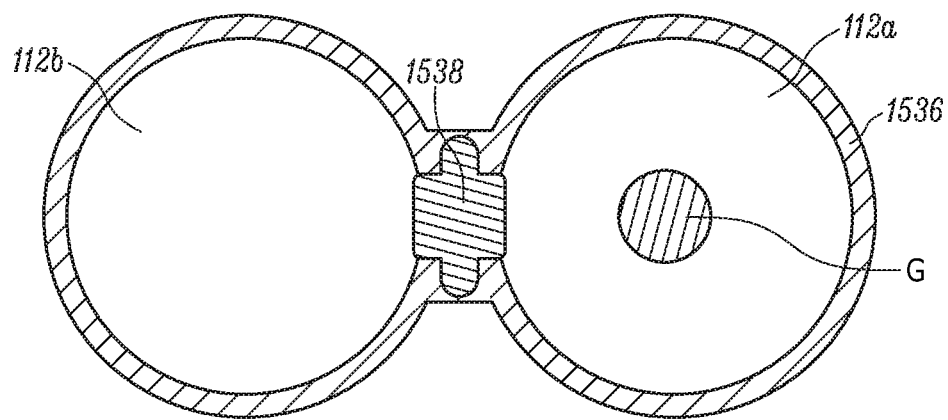
Figure 36C:
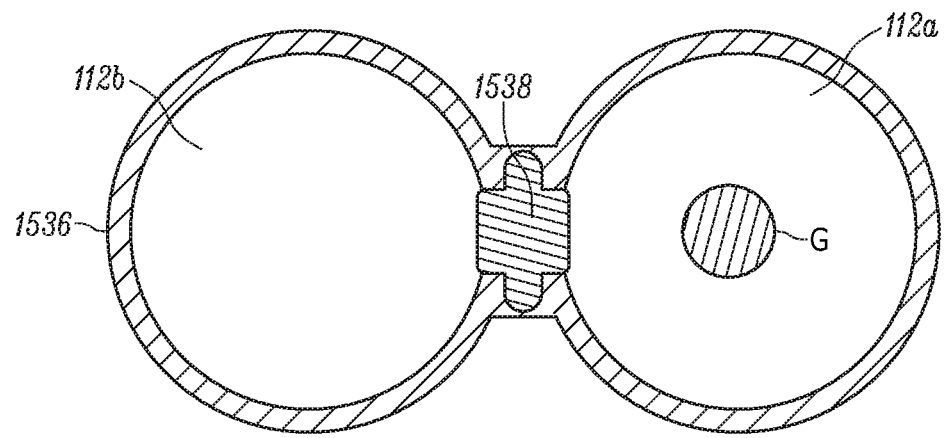
Figure 36D:
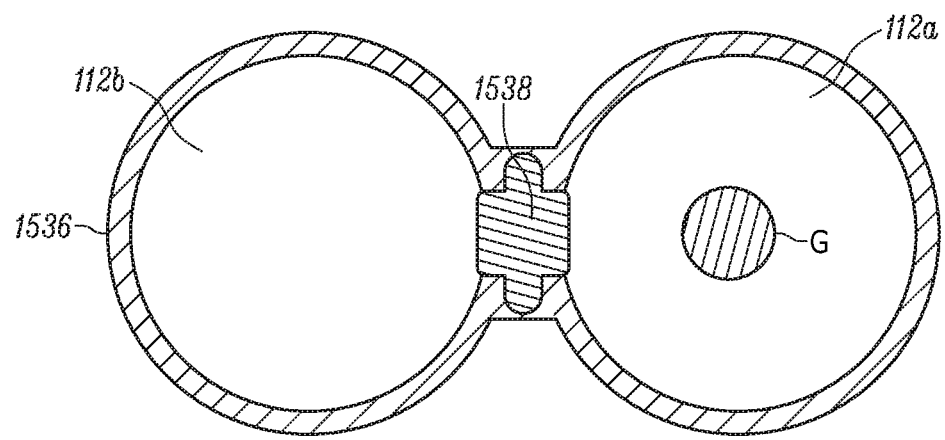
Figure 37:
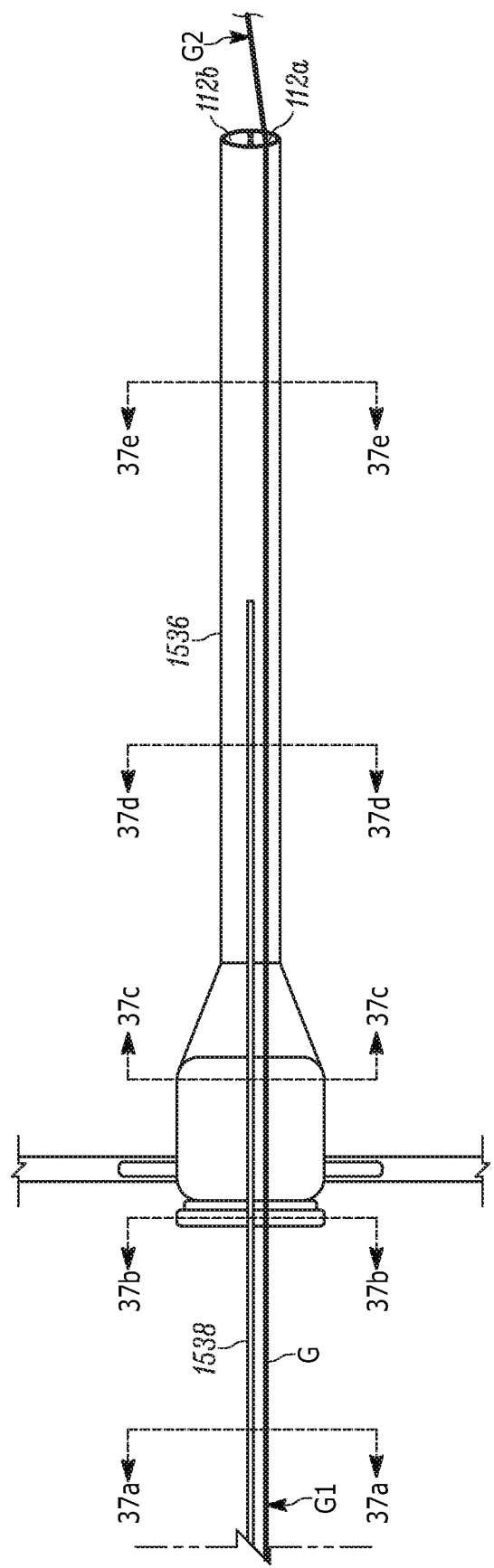
Figure 37A:
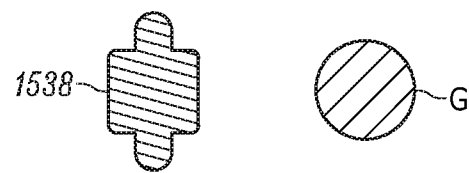
Figure 37B:
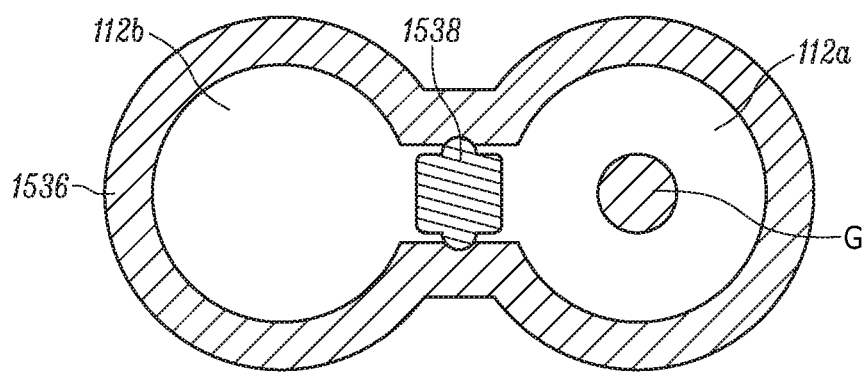
Figure 37C:
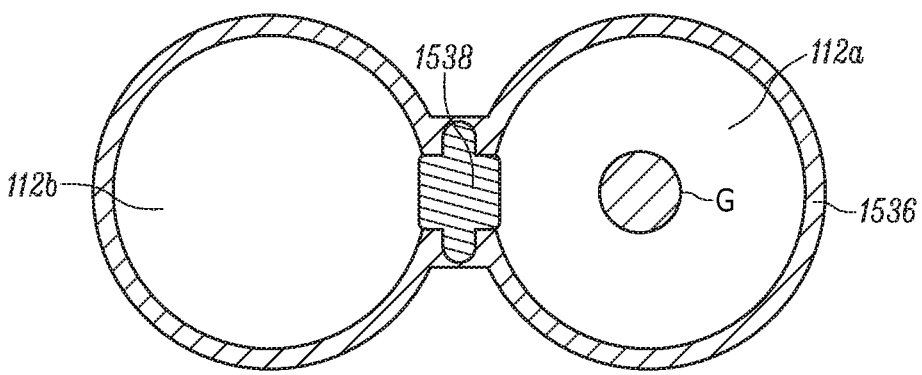
Figure 37D:
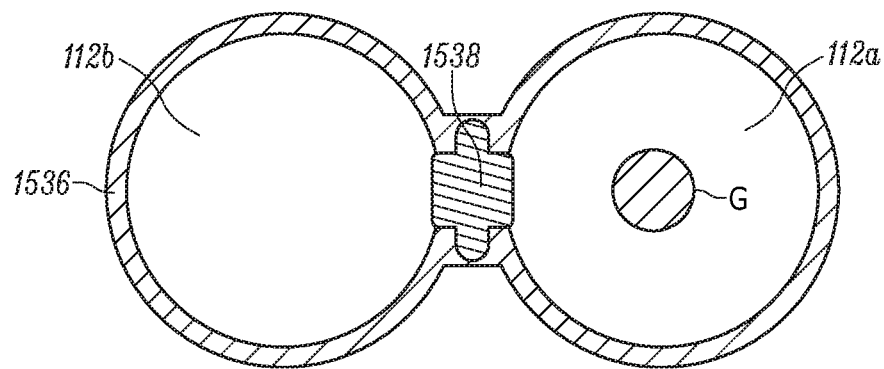
Figure 37E:
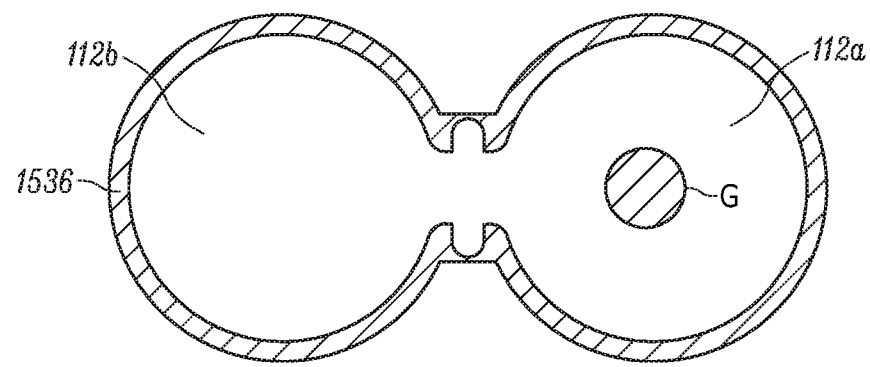
Figure 38:
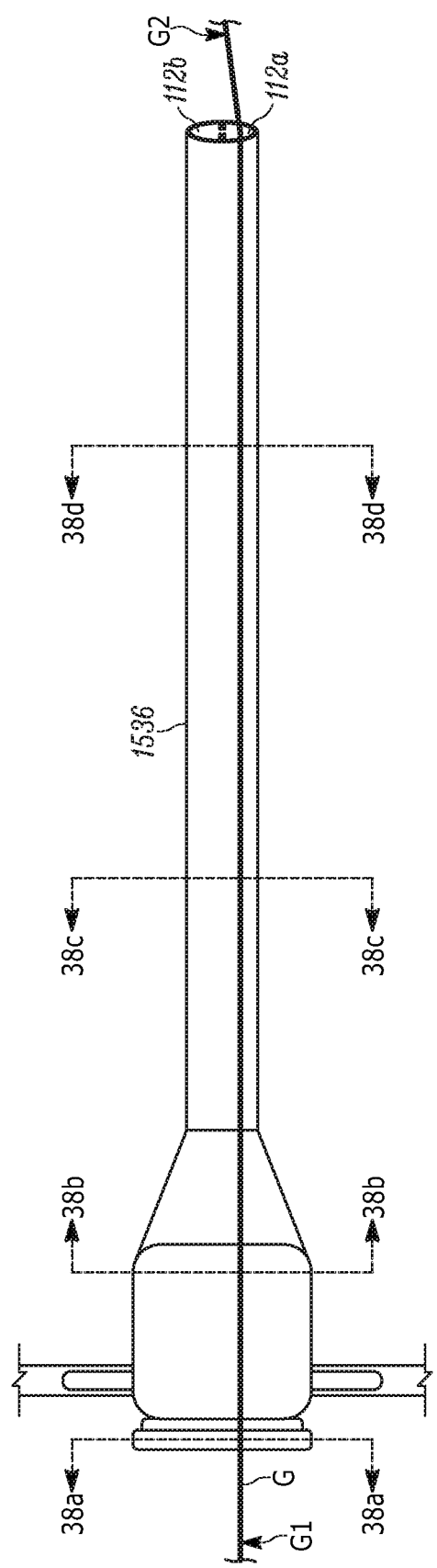
Figure 38A:
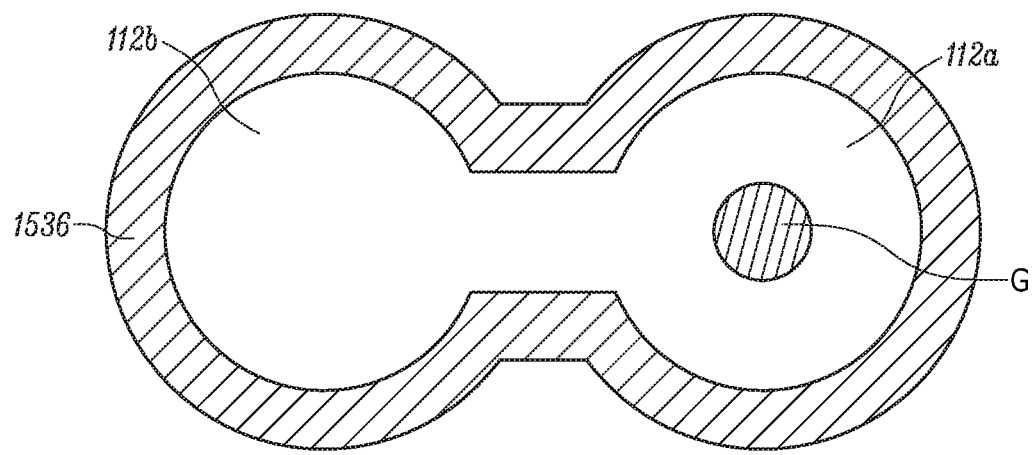
Figure 38B:
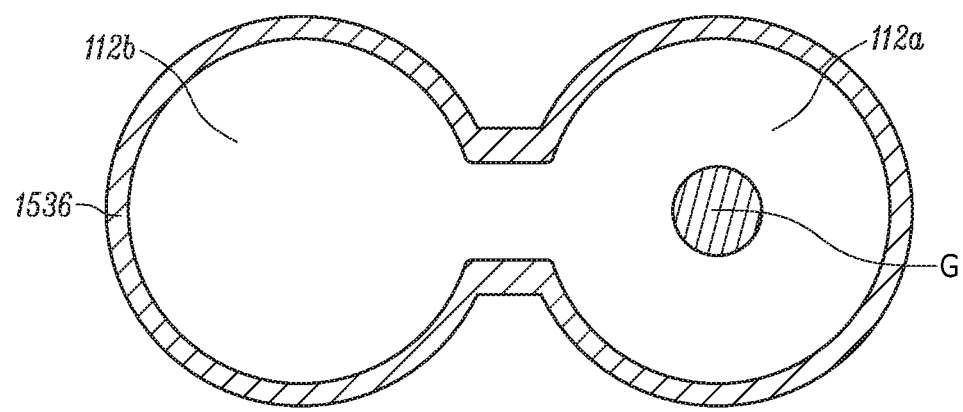
Figure 38C:
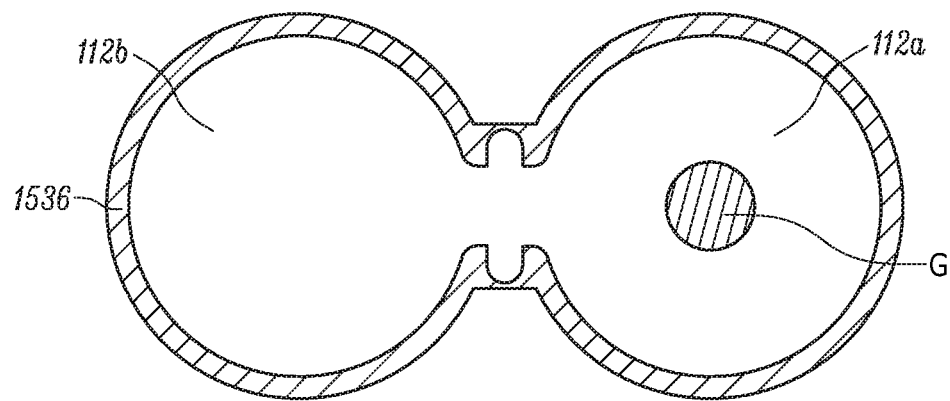
Figure 38D:
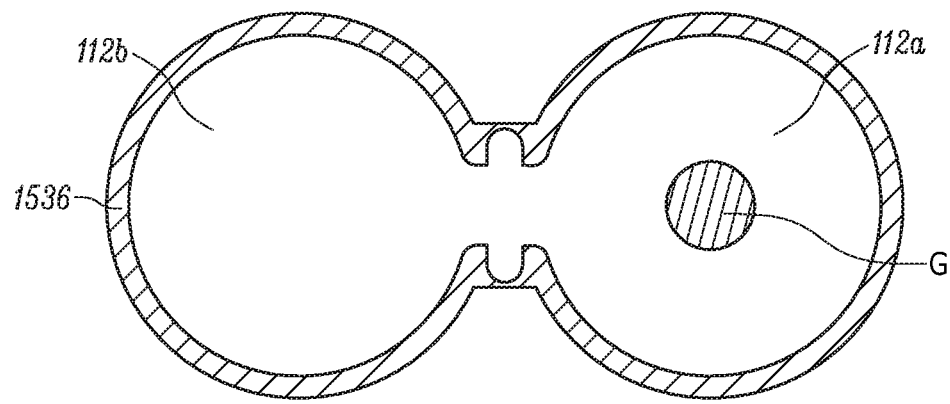

FIGS. 36-41d depict an example transition sequence of a guidewire G from at least one of the plurality of sheath lumens 112 (shown here as the sheath lumens 112a and 112b) to at least one other of the plurality of sheath lumens 112a, 112b in the introducer sheath C 1536. As shown in FIG. 36, with the septum C 1538 inserted in the introducer sheath C 1536, the guidewire proximal end G1 is directed through a first sheath lumen 112 (shown here as the first sheath lumen 112a) of the plurality of sheath lumens 112a, 112b. FIGS. 36a-d depict cross-sectional views of various points along the introducer sheath C 1536, to show the arrangement of the introducer sheath C 1536, the septum C 1538, and the guidewire G in FIG. 36. As shown in FIGS. 37-38, the septum C 1538 may be removed from the introducer sheath C 1536. FIGS. 37a-e depict cross-sectional views of various points along the introducer sheath C 1536, to show the arrangement of the introducer sheath C 1536, the septum C 1538, and the guidewire G in FIG. 37. FIGS. 38a-d depict cross-sectional views of various points along the introducer sheath C 1536, to show the arrangement of the introducer sheath C 1536 and the guidewire G in FIG. 38.

Figure 39:
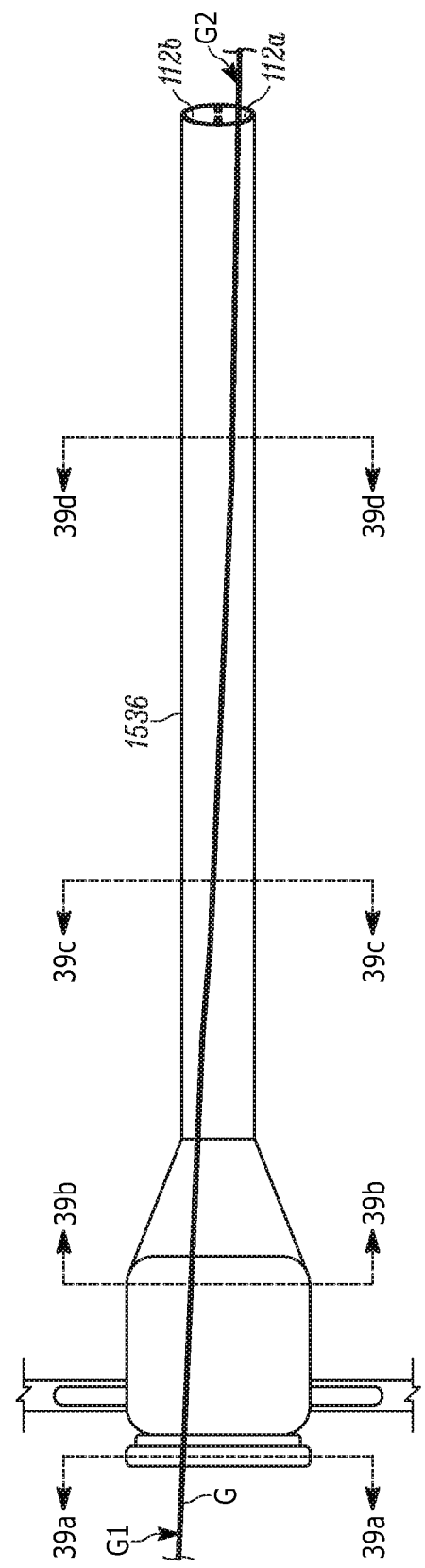
Figure 39A:
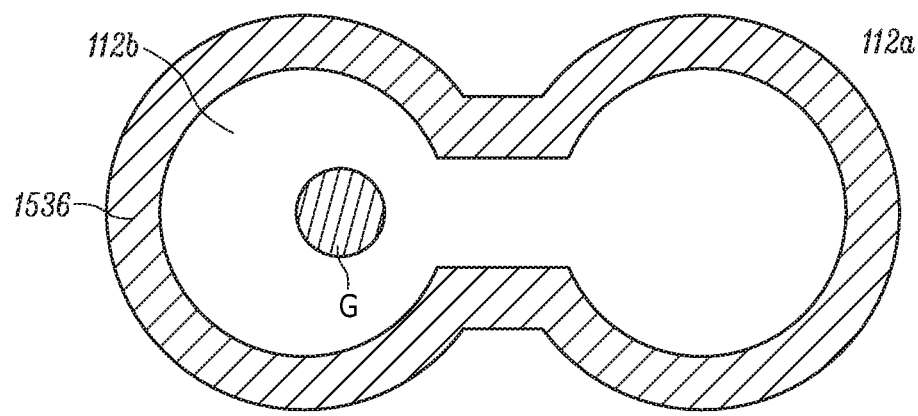
Figure 39B:
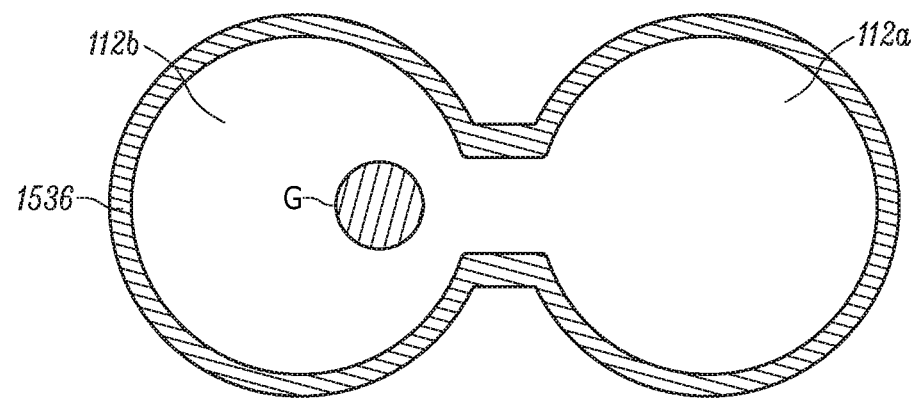
Figure 39C:
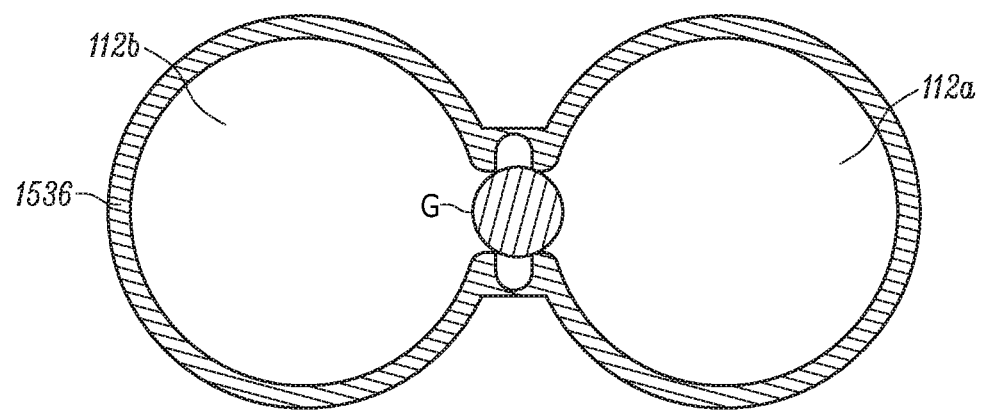
Figure 39D:
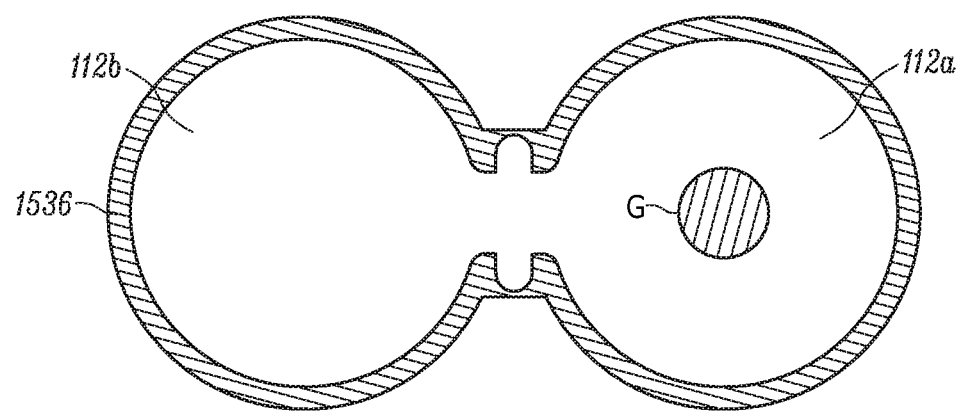

As shown in FIG. 39a, when the septum C 1538 is removed from the introducer sheath C 1536, the first sheath lumen 112a and a second sheath lumen 112 (shown here as the second sheath lumen 112b) are in fluid communication with one another. The guidewire proximal end G1 may then be urged from the first sheath lumen 112a to the second sheath lumen 112b. FIGS. 39a-d depict cross-sectional views of various points along the introducer sheath C 1536, to show the arrangement of the introducer sheath C 1536 and the guidewire G in FIG. 39.

Figure 40:
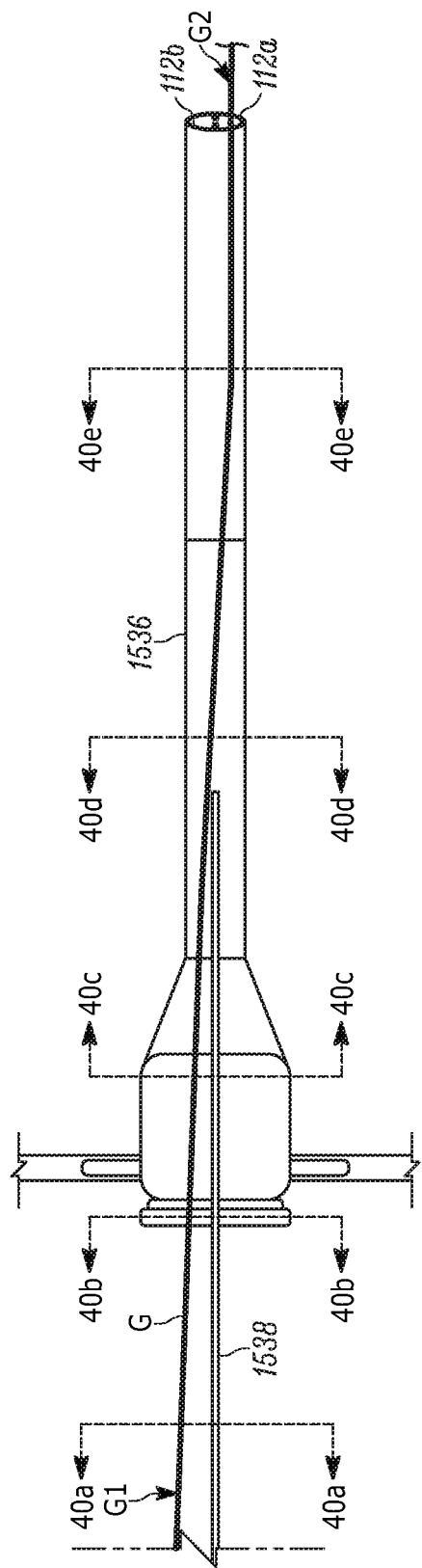
Figure 40A:
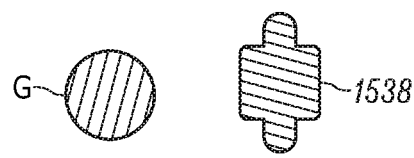
Figure 40B:
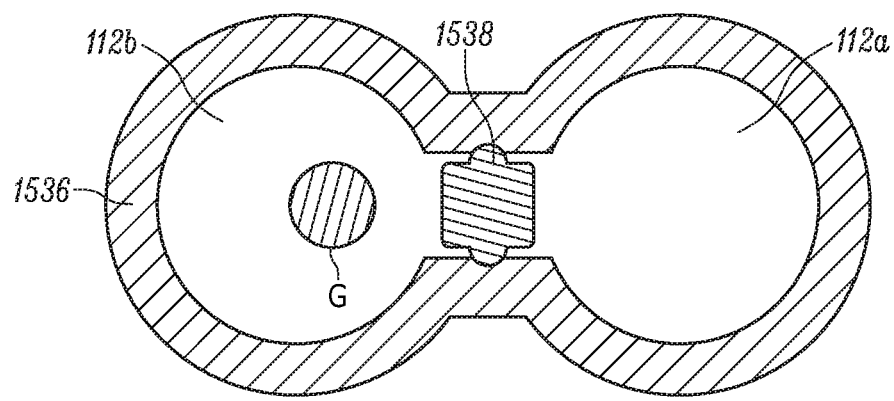
Figure 40C:
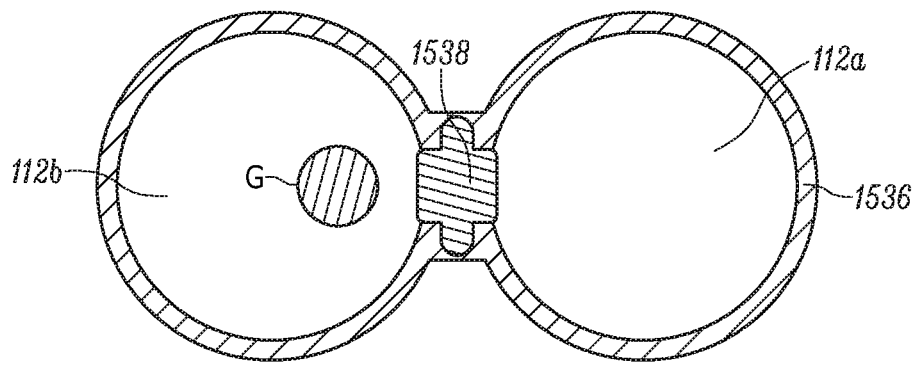
Figure 40D:
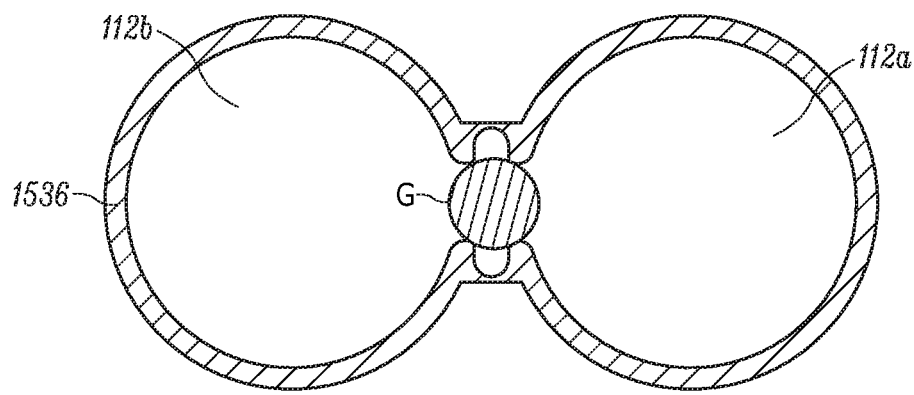
Figure 40E:
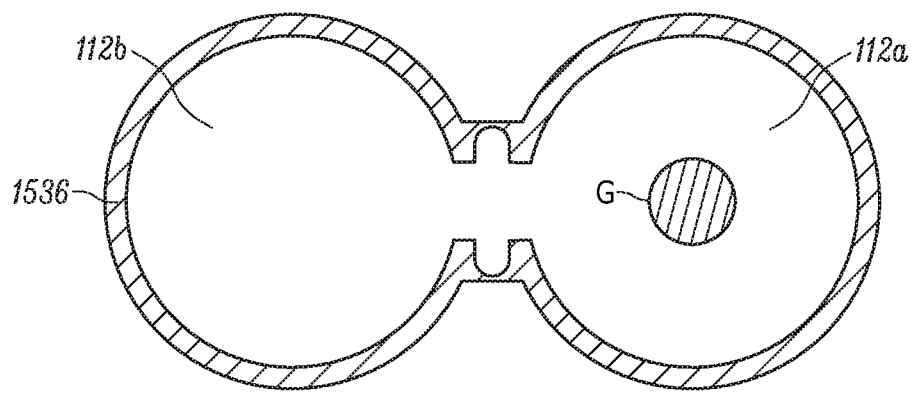
Figure 41:
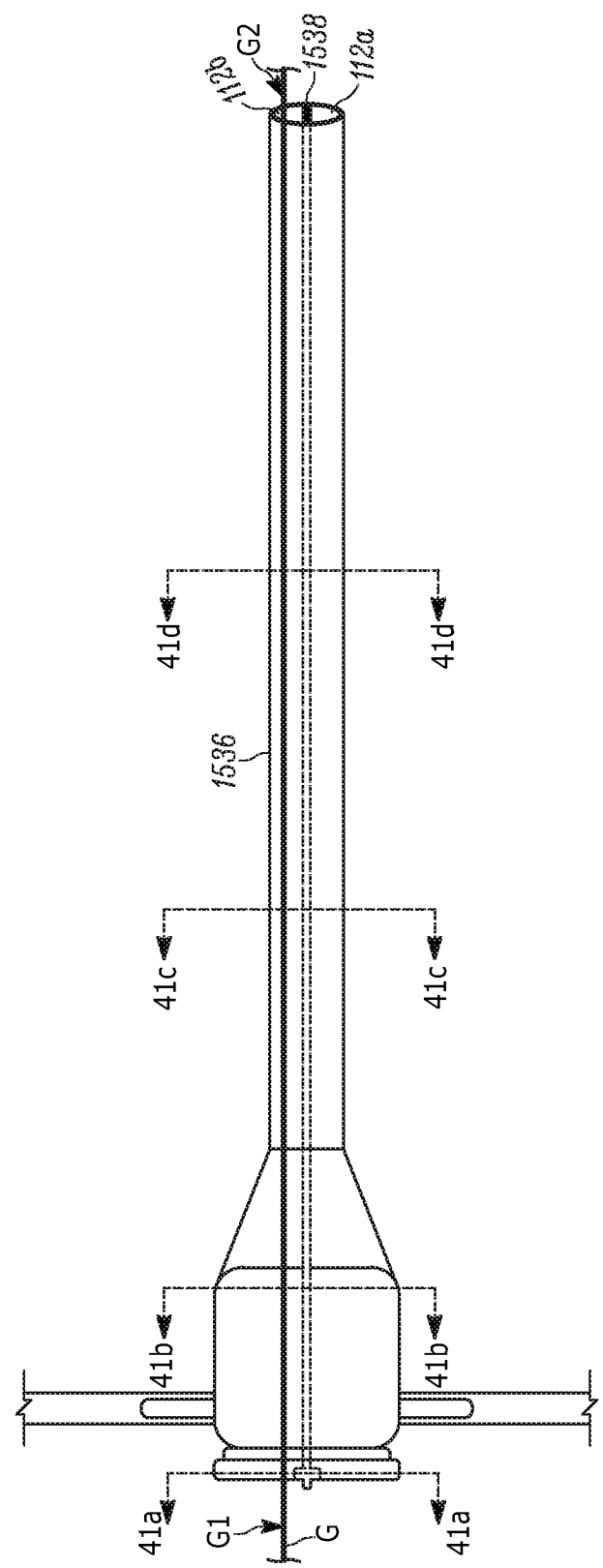
Figure 41A:
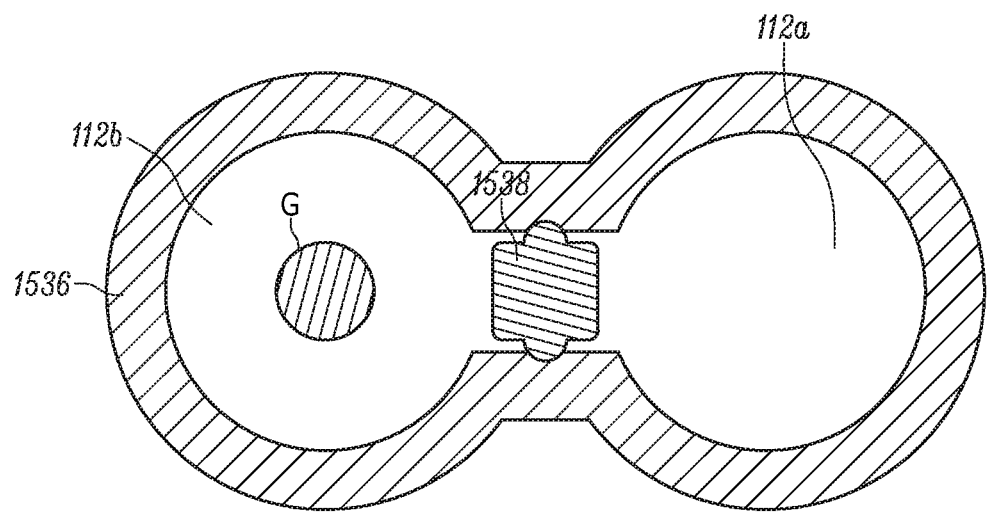
Figure 41B:
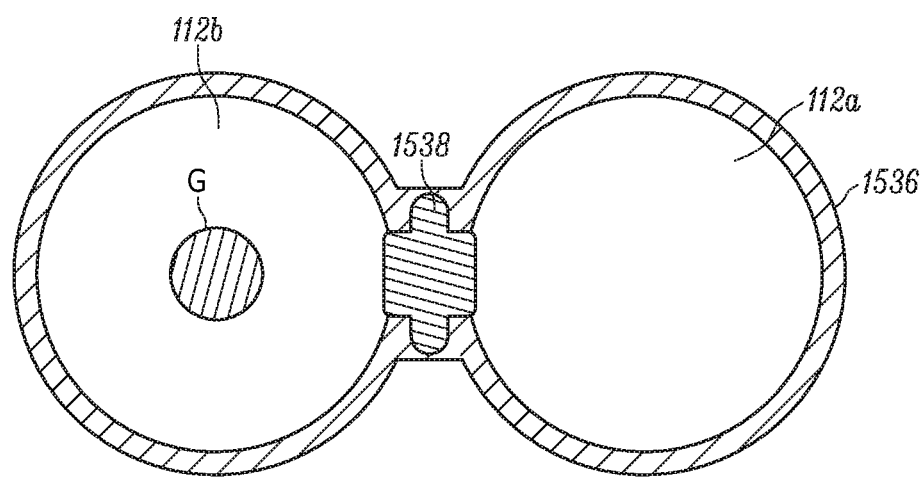
Figure 41C:
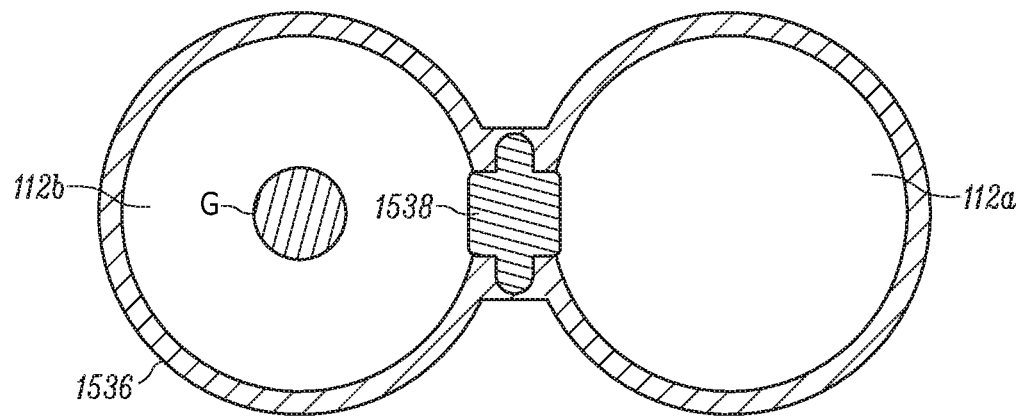
Figure 41D:
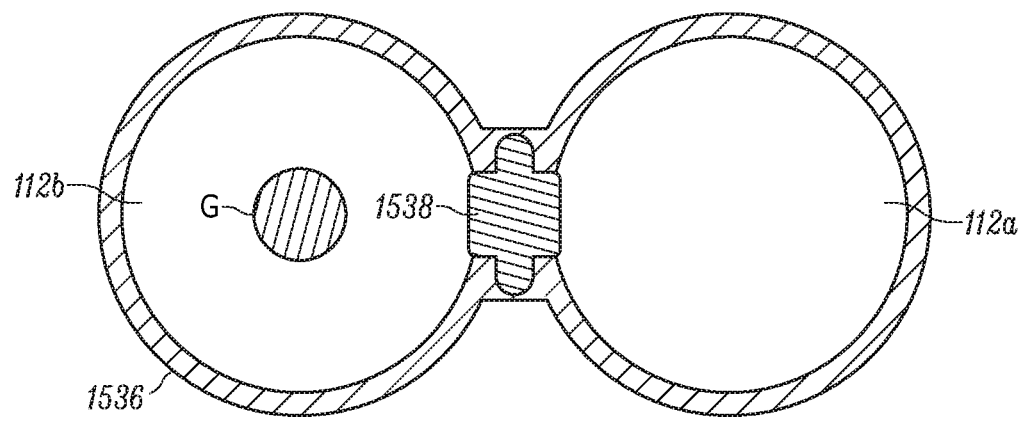

As shown in FIGS. 40-41, with the guidewire proximal end G1 in the second sheath lumen 112b, the septum C 1538 may be inserted into the introducer sheath C 1536. The septum C 1538 urges the guidewire G from the first sheath lumen 112a to the second sheath lumen 112b as the septum C 1538 is inserted into the introducer sheath C 1536. FIGS. 40a-e depict cross-sectional views of various points along the introducer sheath C 1536, to show the arrangement of the introducer sheath C 1536, the septum C 1538, and the guidewire G in FIG. 40. FIGS. 41a-d depict cross-sectional views of various points along the introducer sheath C 1536, to show the arrangement of the introducer sheath C 1536, the septum C 1538, and the guidewire G in FIG. 41.

In use, the introducer sheath 100 having the plurality of sheath lumens 112 extending between the sheath proximal and distal ends 106, 108, as described above, is provided. The introducer sheath 100 may be any alternate configuration of the introducer sheath 100, whether or not expressly discussed herein. For the sake of brevity, not every alternate configuration of the introducer sheath 100 is discussed and/or depicted in the following descriptions. However, it is to be understood that the following descriptions may be applicable to certain alternate configurations of the introducer sheath 100, and one of ordinary skill in the art can configure an introducer sheath 100 having desired features and characteristics for a particular use environment.

At least one medical instrument 3360 may be provided. FIG. 42 depicts a first dilator 4262, which can be a first medical instrument, a second medical instrument, or any other medical instrument. The first dilator 4262 has a dilator proximal end 4264 and a dilator distal end 4266. The dilator proximal end 4264 and the dilator distal end 4266 are longitudinally spaced apart by an elongate dilator body 4268. At least a portion of the dilator distal end 4266 may be inwardly tapered. The term "taper" is defined herein as a gradual diminution of thickness, diameter, or width in an elongated object, as is shown by the gradual diminution in diameter of the dilator distal end 4266 in FIG. 42. The term "inward" is defined herein as a taper that becomes gradually smaller, such as shown as the gradual diminution in diameter between the dilator body 4268 and a dilator open tip 4270, which will be discussed below, in FIG. 42. Further, the inward taper, such as the taper of the dilator distal end 4266, could include no expansion in diameter (or outward taper) distal to the dilator body 4268. The first dilator 4262 has a dilator outer surface 4272 and a dilator lumen 4274. The dilator distal end 4266 has the dilator open tip 4270. The dilator lumen 4274 of the first dilator 4262 may extend between the dilator proximal end 4264 and the dilator open tip 4270.

The first dilator 4262 has a dilator side wall opening 4276. The dilator side wall opening 4276 is longitudinally spaced from the dilator open tip 4270. The dilator side wall opening 4276 is positioned on at least one of the dilator body 4268 and the dilator distal end 4266. The dilator side wall opening 4276 selectively places the dilator outer surface 4272 in fluid communication with the dilator lumen 4274.

The first dilator 4262 has a dilator open slit 4278. The dilator open slit 4278 extends between the dilator side wall opening 4276 and the dilator open tip 4270. The dilator open slit 4278 has a dilator open slit first surface 4280 and a dilator open slit second surface 4282. The dilator open slit first surface 4280 oppositely faces and abuts the dilator open slit second surface 4282. The dilator open slit first surface 4280 and the dilator open slit second surface 4282 are elastically separable. That is, a force may be applied to separate the dilator open slit first surface 4280 and the dilator open slit second surface 4282, as that the dilator open slit first surface 4280 will no longer be abutting the dilator open slit second surface 4282. However, upon the removal of the separating force, the dilator open slit first surface 4280 and the dilator open slit second surface 4282 will tend to return toward their original abutting position due to the elastic nature of the material forming the dilator open slit first surface 4280 and the dilator open slit second surface 4282.

FIG. 43 depicts a second dilator 4384, which can be a first medical instrument, a second medical instrument, or any other medical instrument. Similar to the first dilator 4262, the second dilator 4384 has a dilator proximal end 4264 and a dilator distal end 4266. The dilator proximal end 4264 and the dilator distal end 4266 are longitudinally spaced apart by an elongate dilator body 4268. At least a portion of the dilator distal end 4266 may be inwardly tapered. The second dilator 4384 has a dilator outer surface 4272 and a dilator lumen 4274. The dilator distal end 4266 has a dilator open tip 4270. The dilator lumen 4274 of the second dilator 4384 may extend between the dilator proximal end 4264 and the dilator open tip 4270.

Figure 45:
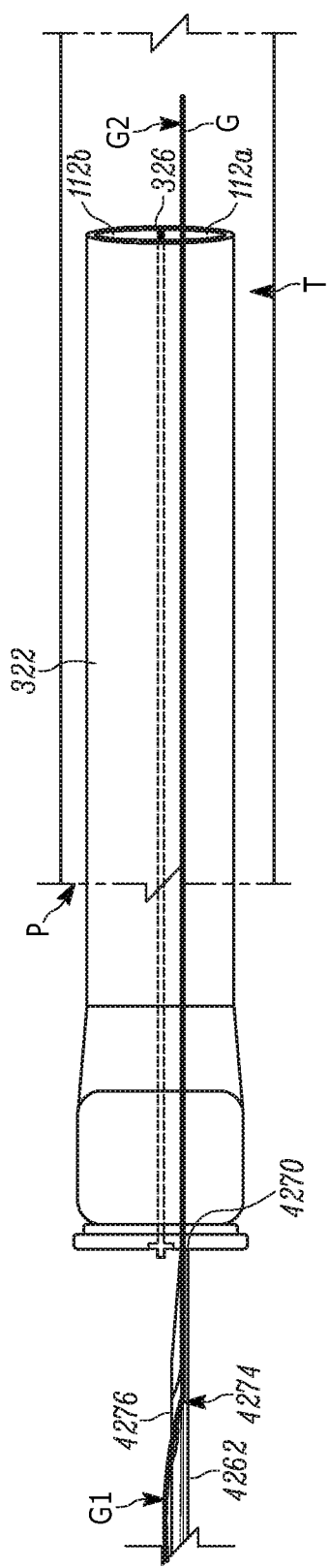
Figure 46:
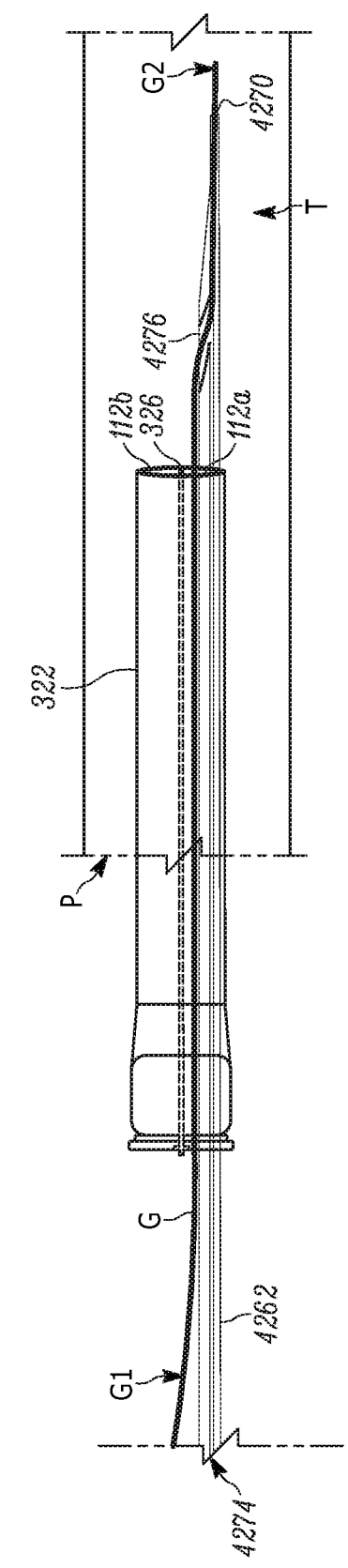

A guidewire distal end G2 is inserted into a target patient tissue site T through a patient tissue access point P. The guidewire proximal end G1 is directed through a first sheath lumen 112 (shown here as the first sheath lumen 112*a*) of the plurality of sheath lumens 112 (shown here as the sheath lumens 112*a* and 112*b*). As shown in FIG. 44, the introducer sheath B 322 is directed toward the target patient tissue site T along the guidewire G. As shown in FIG. 45, the guidewire proximal end G1 may be at least partially directed through the first dilator 4262, when the first dilator 4262 is provided. In particular, the guidewire proximal end G1 is directed into the first dilator open tip 4270, through at least a portion of the dilator lumen 4274, and out of the first dilator 4262, such as through the dilator side wall opening 4276. FIG. 46 depicts the first dilator 4262 being directed to the target patient tissue site G along the guidewire G and at least partially through the first sheath lumen 112*a*.

Figure 47:
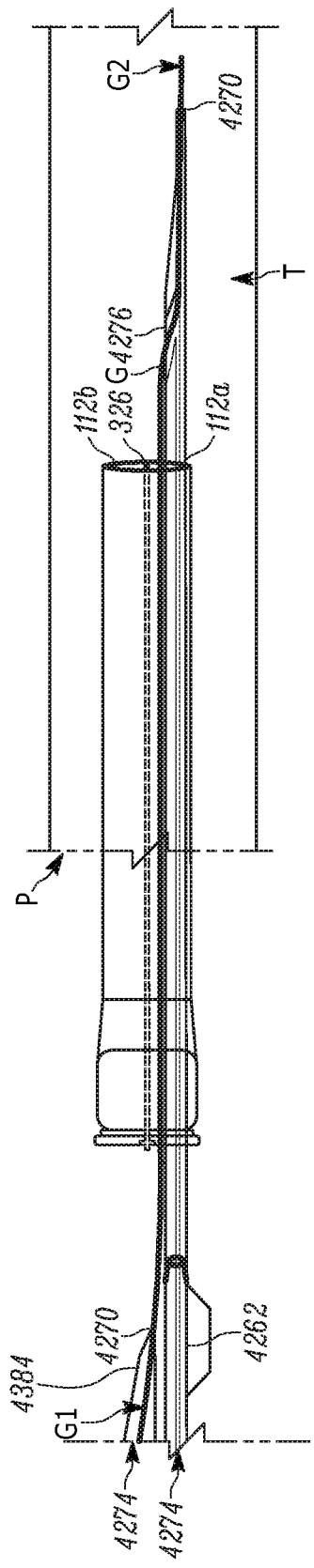
Figure 48:
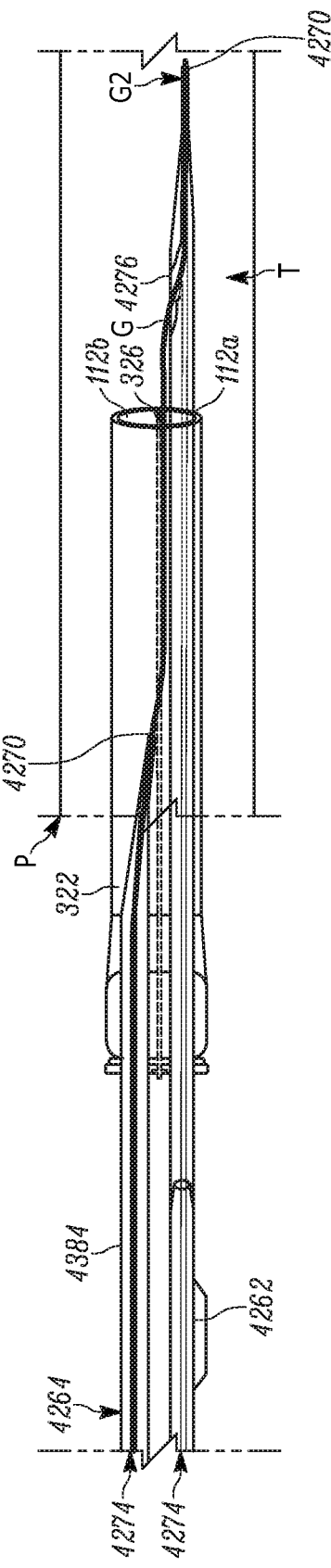
Figure 50A:
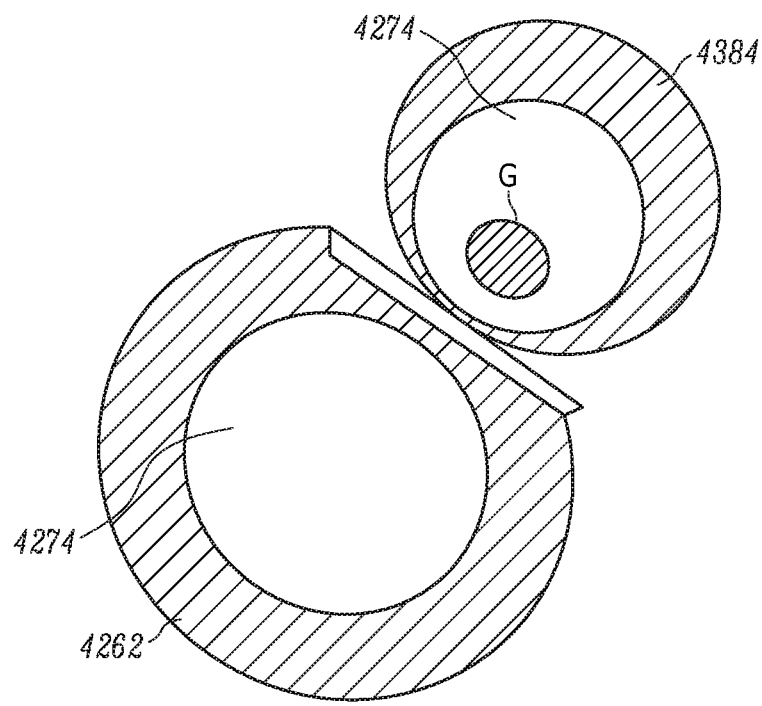
Figure 50B:
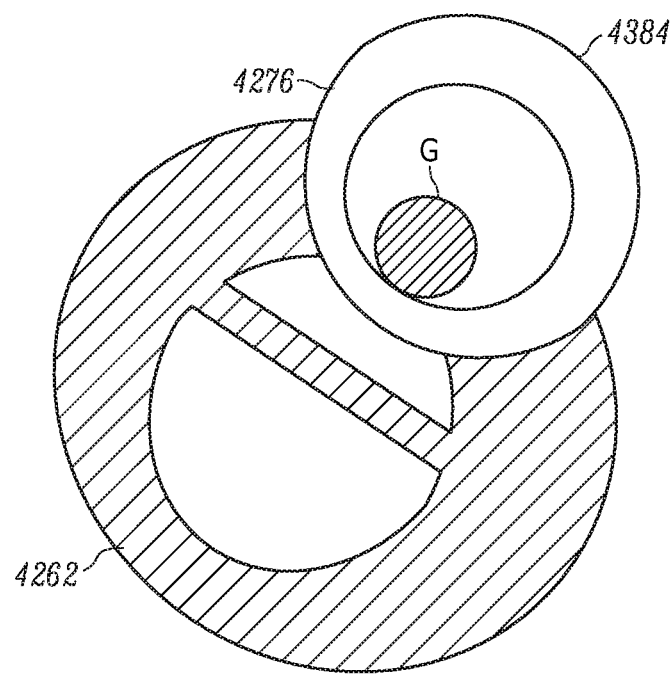
Figure 50C:
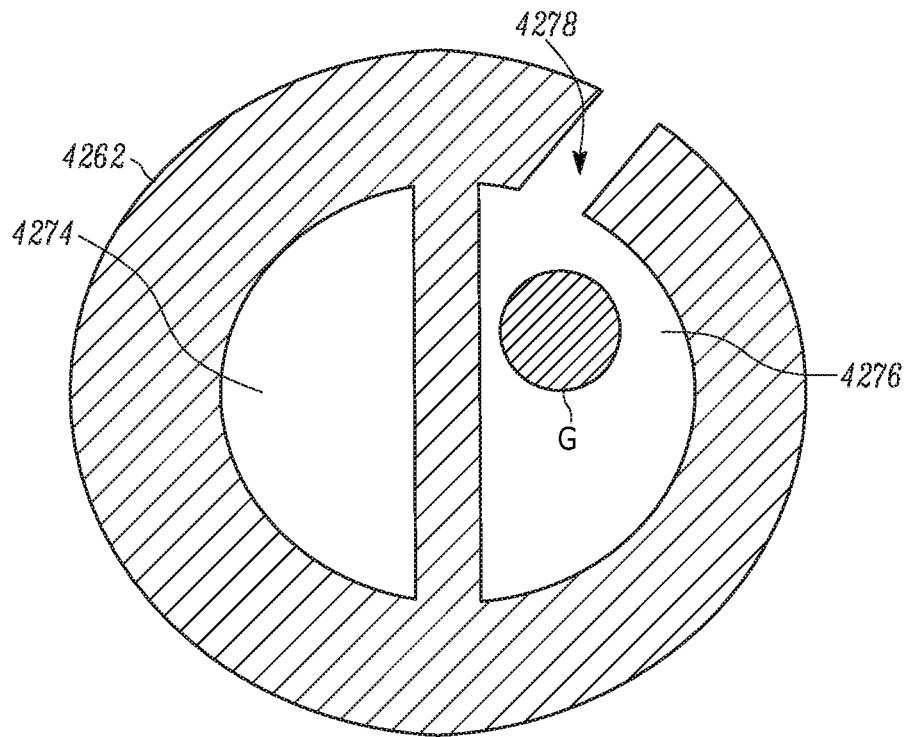
Figure 50D:
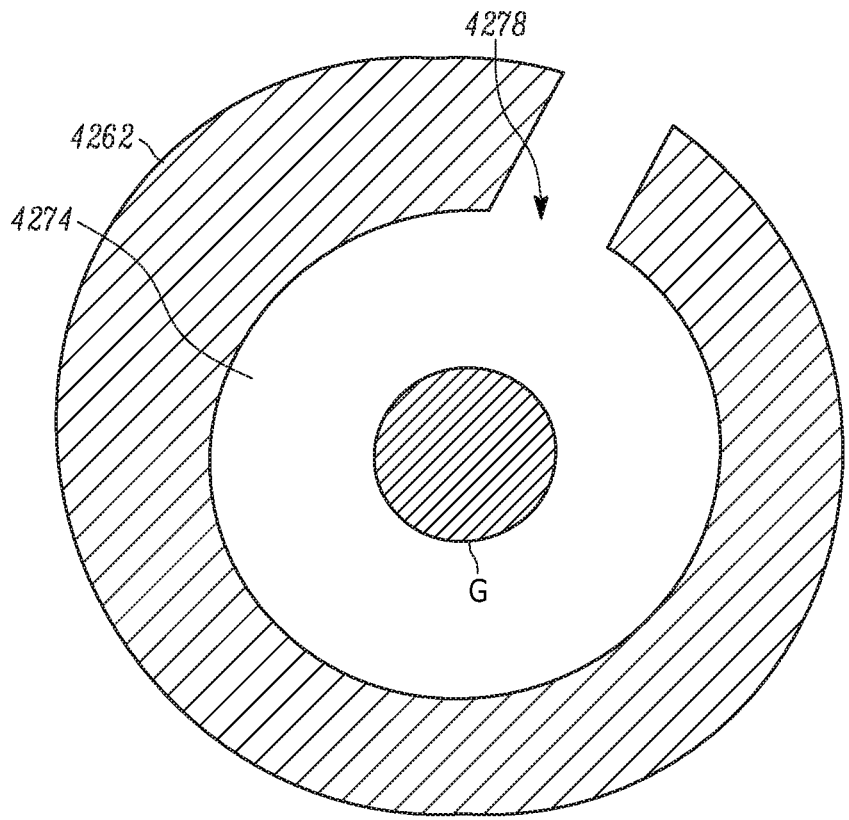
Figure 50E:
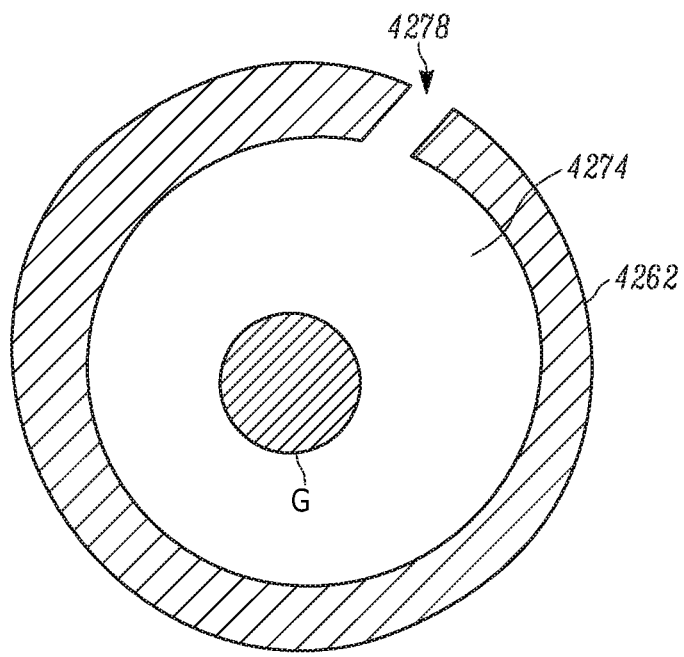

As shown in FIG. 47, the guidewire proximal end G1 is directed through the second dilator 4384, when the second dilator 4384 is provided. In particular, the guidewire proximal end G1 is directed into the dilator open tip 4270, through at least a portion of the dilator lumen 4274, and out from the second dilator 4384, such as through the dilator proximal end 4264 of the second dilator 4384. As shown in FIGS. 48-49, the second dilator 4384 is directed toward the target patient tissue site T along the guidewire G and at least partially through a second sheath lumen (shown here as the second sheath lumen 112*b*) until the dilator open tip 4270 of the second dilator 4384 is adjacent to the dilator side wall opening 4276 of the first dilator 4262. The second dilator 4384 urges the guidewire G from the first sheath lumen 112*a* to the second sheath lumen 112*b* as the second dilator 4384 moves at least partially through the second sheath lumen 112*b*, while the guidewire G is maintained at the target patient tissue site T. The second dilator 4384 urges the guidewire G from the first sheath lumen 112*a* to the second sheath lumen 112*b* by causing at least a portion of the guidewire G to be urged into at least a portion of the septum B 326 to selectively deflect at least a portion of the septum B 326 from the biased condition. The deflection of the septum B 326 at least partially provides fluid communication between the first and second sheath lumens 112*a*, 112*b* so that the portion of the guidewire G being urged into the septum B 326 passes into the second sheath lumen 112*b* from the first sheath lumen 112*a*.

Figure 51:
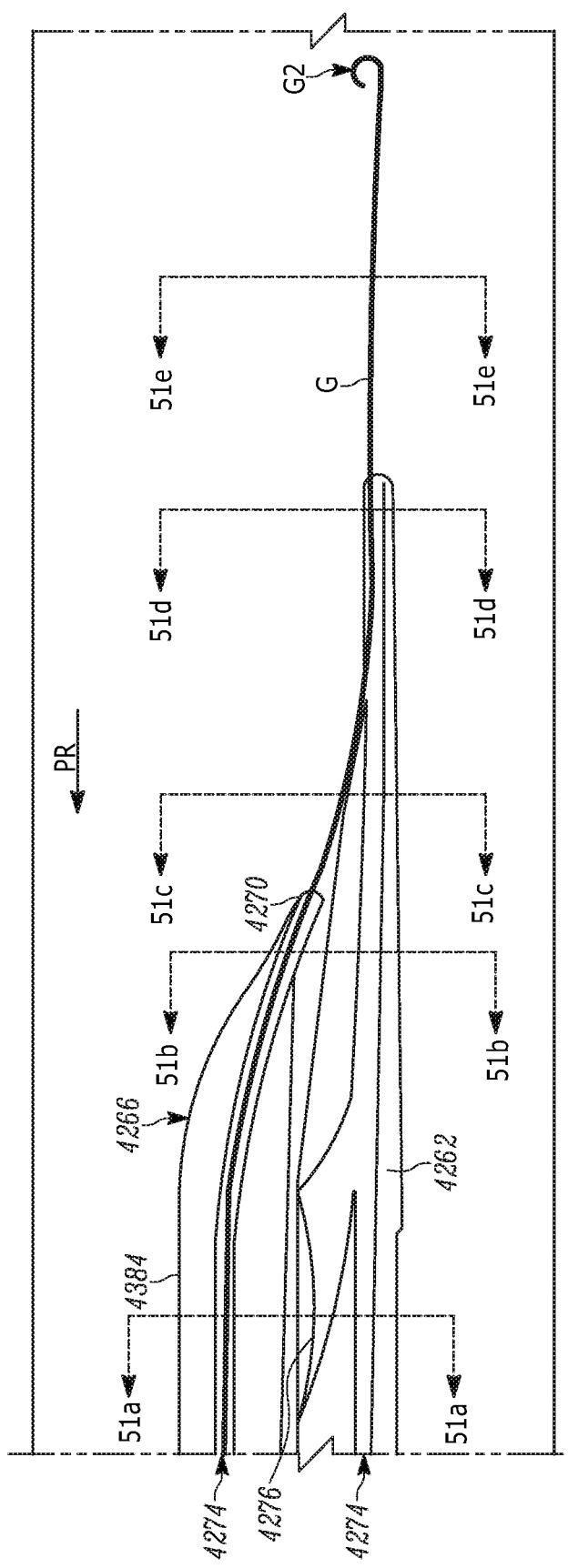
Figure 51A:
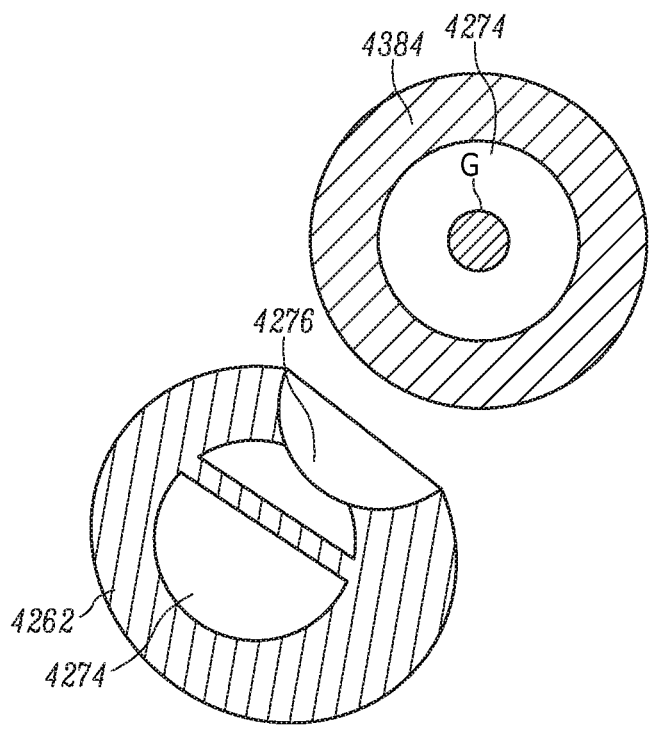
Figure 51B:
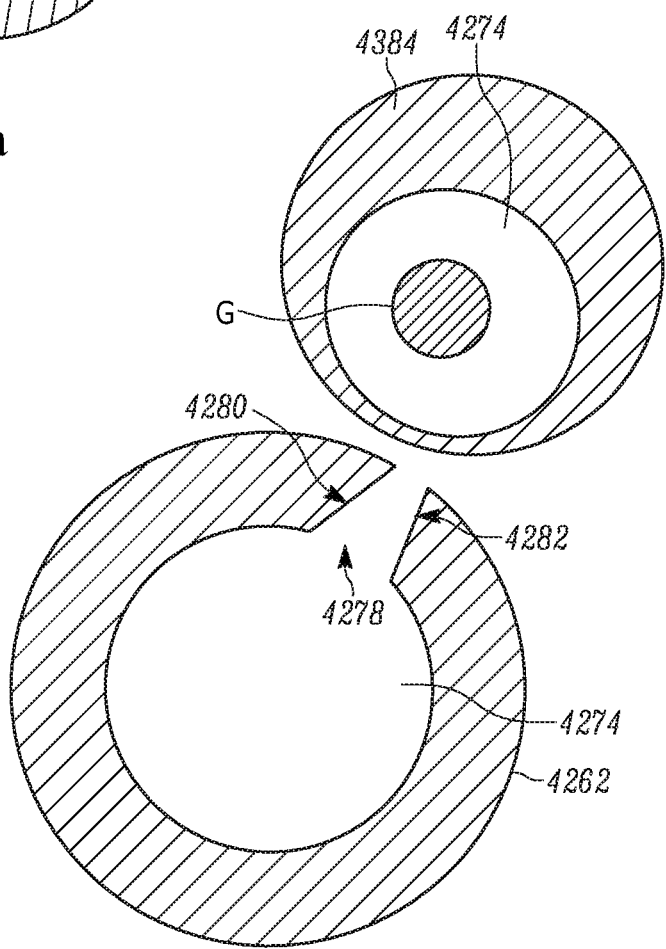
Figure 51C:
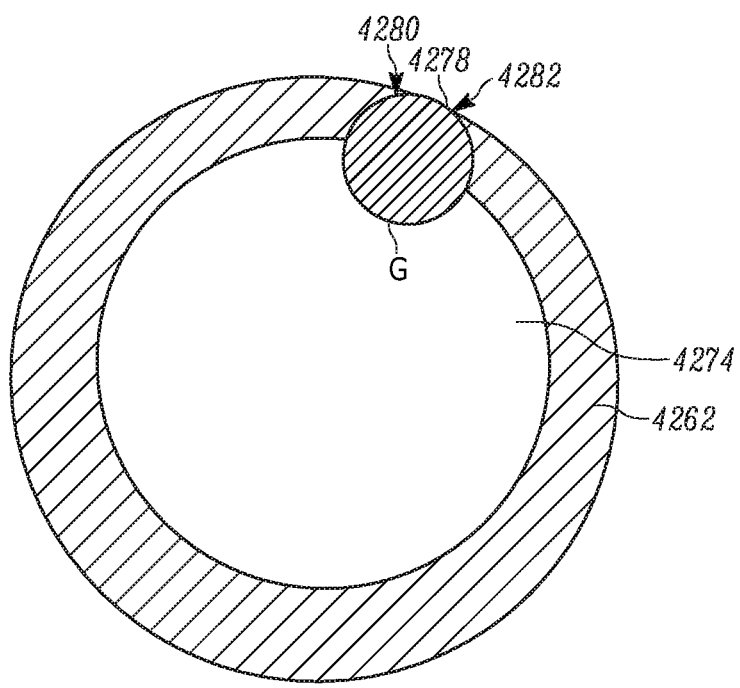
Figure 51D:
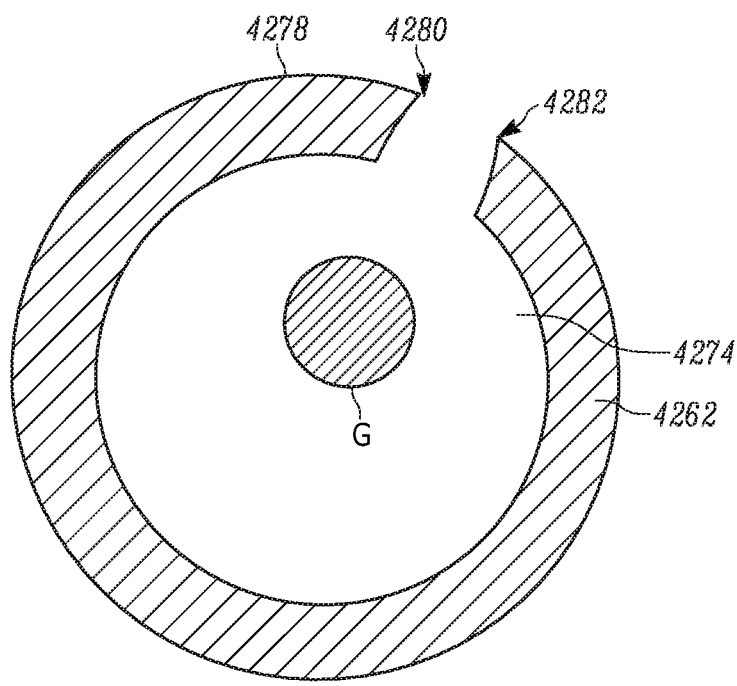
Figure 51E:
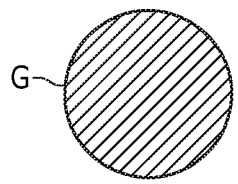
Figure 52:
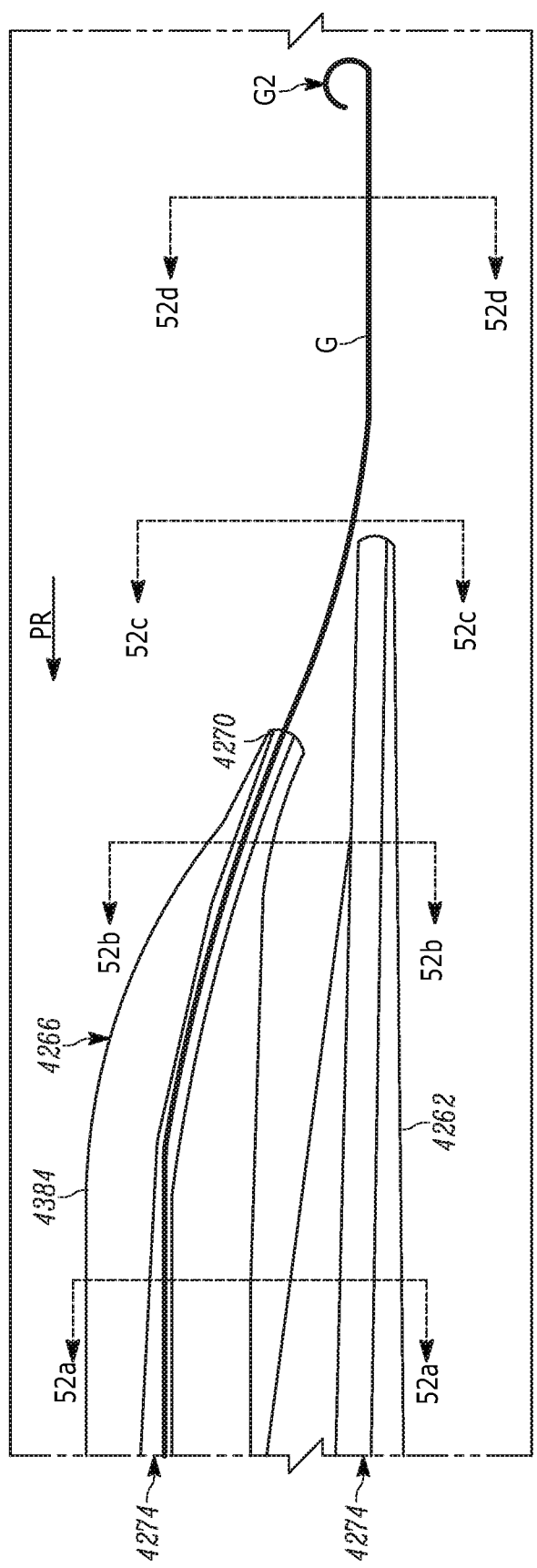
Figure 52A:
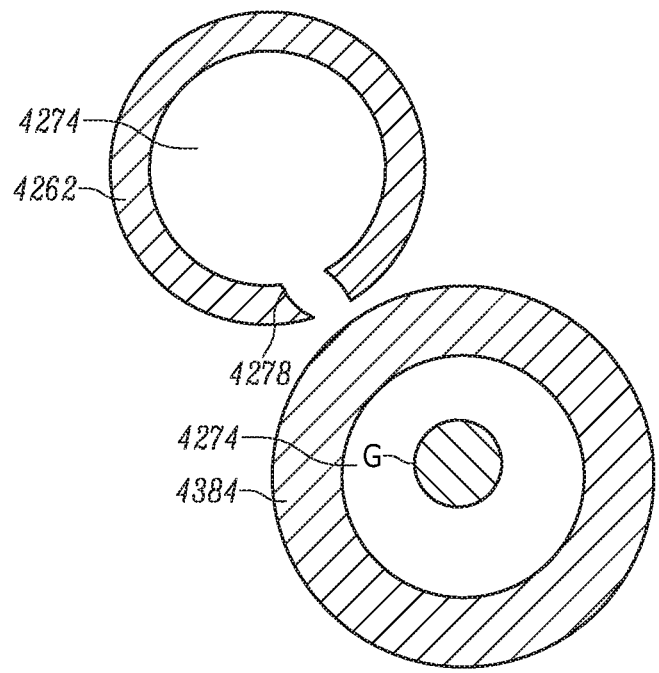
Figure 52B:
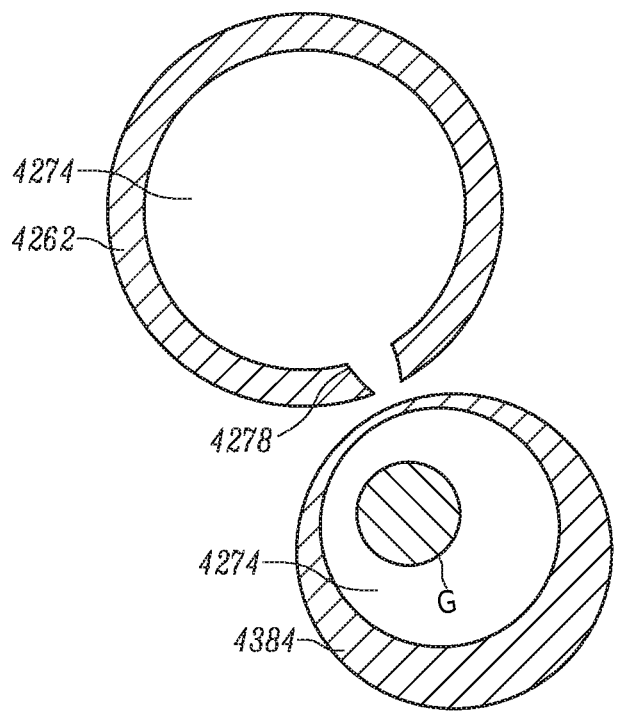
Figure 52C:
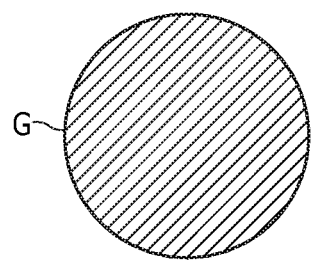
Figure 52D:
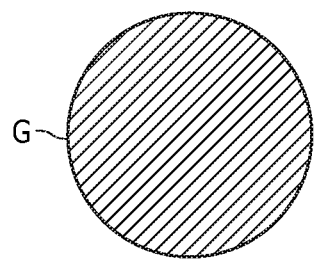

As shown in FIG. 50, with the first and second dilators 4262, 4384 at or adjacent to the target patient tissue site T, the dilator open tip 4270 and at least a portion of the dilator distal end 4266 of the second dilator 4384 may each be directed at least one of adjacent to and into the dilator side wall opening 4276 of the first dilator 4262. FIGS. 50*a-e* depict cross-sectional views of various points along the first and second dilators 4262, 4384, to show the arrangement of the first and second dilators 4262, 4384 and the guidewire G in FIG. 50. As shown in FIGS. 51 and 52, with the dilator distal end 4266 of the second dilator 4384 at least one of adjacent to and at least partially in the dilator side wall opening 4276 of the first dilator 4262, the first dilator 4262 may be longitudinally moved toward a proximal direction (shown as the arrow PR in FIGS. 51 and 52) to remove the first dilator 4262 from the guidewire G, while the guidewire G is maintained at the target patient tissue site T. In particular, as the first dilator 4262 is moved toward the proximal direction, the dilator distal end 4266 of the second dilator 4384 selectively urges the dilator open slit first surface 4280 of the first dilator 4262 elastically apart from the dilator open slit second surface 4282 of the first dilator 4262 and the first dilator 4262 is removed from the guidewire G. Thus, the dilator distal end 4266 of the second dilator 4384 can be thought of as acting as a pivot arrangement to urge the first dilator 4262 from the guidewire G. FIGS. 51*a-e* depict cross-sectional views of various points along the first and second dilators 4262, 4384, to show the arrangement of the first and second dilators 4262, 4384 and the guidewire G in FIG. 51. FIGS. 52*a-d* depict cross-sectional views of various points along the first and second dilators 4262, 4384, to show the arrangement of the first and second dilators 4262, 4384 and the guidewire G in FIG. 52.

Figure 53:
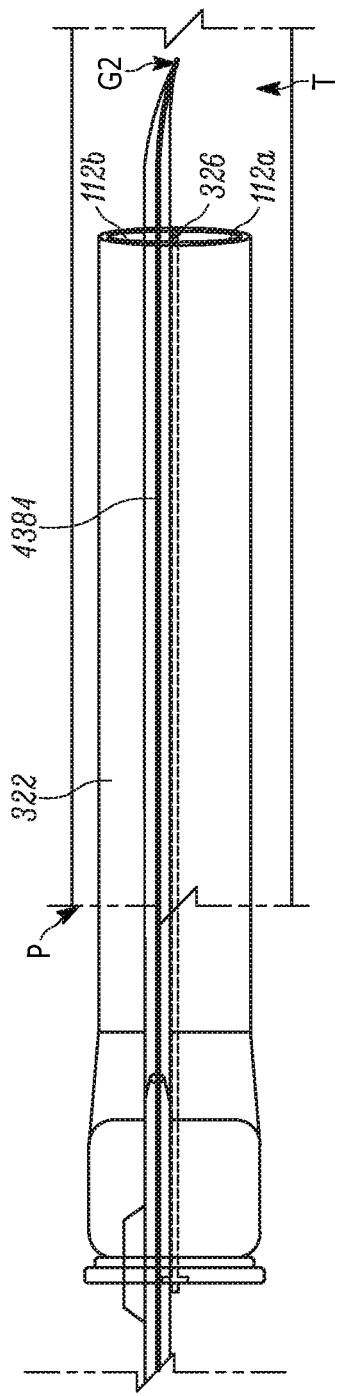

Once the first dilator 4262 is fully removed from the guidewire G, a second guidewire (not shown) may be inserted through the dilator lumen 4274 of the first dilator 4262 and toward the target patent tissue site T. Instead of, or in addition to the above, once the first dilator 4262 is fully removed from the guidewire G, the first dilator 4262 may be removed from the target patient tissue site T and the introducer sheath B 322, as shown in FIG. 53. The second dilator 4384 may also be removed from the guidewire G and the introducer sheath B 322 by longitudinally moving the second dilator 4384 in the proximal direction PR.

Similar to the above sequence of operation in FIGS. 42-53, the introducer sheath B 322 and the first and second dilators 4262, 4384 may be used to insert the introducer sheath B 322 through the patient tissue access point P. In such case, the guidewire distal end is G2 inserted through the patient tissue access point P. The guidewire proximal end G1 is directed through the first sheath lumen 112a of the plurality of sheath lumens 112a, 112b. The guidewire proximal end G1 is directed at least partially through the first dilator 4262, in a similar sequence as discussed above. The first dilator 4262 is directed over the guidewire G and at least partially through the first sheath lumen 112a. The guidewire proximal end G1 is directed at least partially through the second dilator 4384, in a similar sequence as discussed above. The second dilator 4384 is directed over the guidewire G and at least partially through the second sheath lumen 112b of the plurality of sheath lumen 112a, 112b. The second dilator 4384 urges the guidewire G from the first sheath lumen 112a to the second sheath lumen 112b as the second dilator 4384 moves at least partially through the second sheath lumen 112b, while the guidewire G is maintained through the patient tissue access point P.

The first and second dilators 4262, 4384 are aligned with the introducer sheath B 322 so that at least a portion of both of the first and second dilators 4262, 4384 extend out from the introducer sheath B 322 and form a smooth outer contour with the sheath distal end 108 of the introducer sheath B 322. The term "smooth" is defined herein as moving or progressing without significant breaks, sudden changes, or shifts. The smooth outer contour may allow for a smooth dilation of the patient tissue access point P. With the first and second dilators 4262, 4384 aligned with the introducer sheath B 322, the introducer sheath B 322, the first dilator 4262, and the second dilator 4384 may be collectively directed through the patient tissue access point P along the guidewire G. Once the introducer sheath B 322, the first dilator 4262, and the second dilator 4384 are collectively directed through the patient tissue access point P, the introducer sheath B 322, the first dilator 4262, and the second dilator 4384 may be directed toward the target patient tissue site T and/or at least one of the first and second dilators 4262, 4384 may be removed from the guidewire in a similar sequence as described above.

Figure 54:
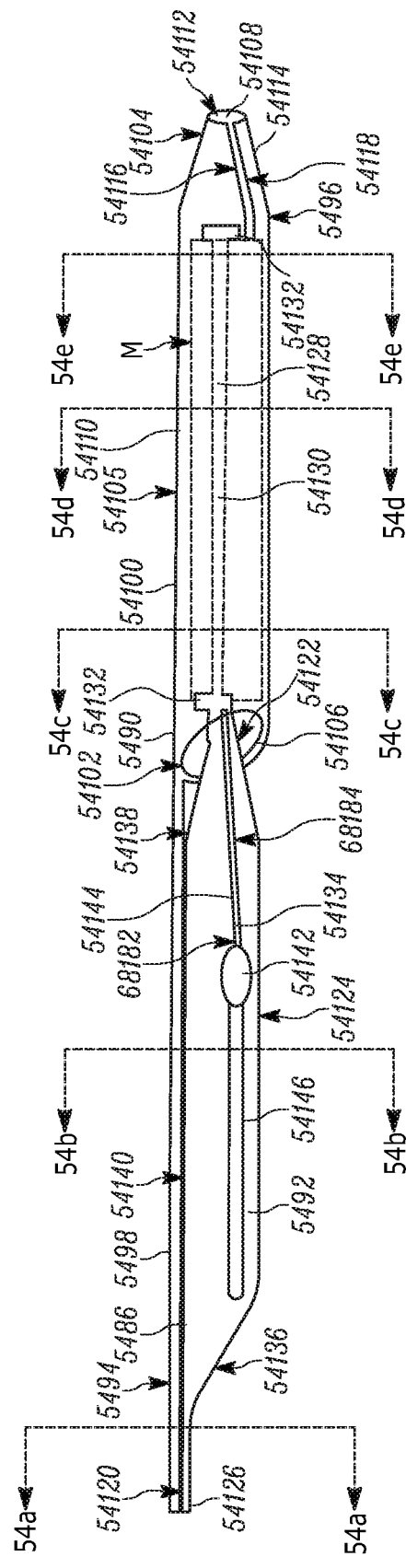
FIGS. 54-72e illustrate an example sequence of operation of a portion of the aspect of FIG. 3, including cross-sectional views.
Figure 54A:
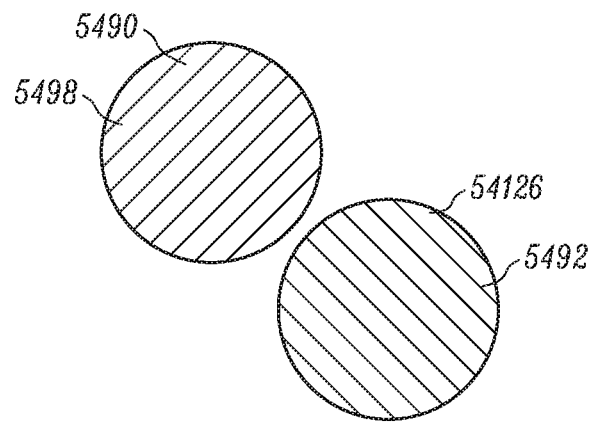
Figure 54B:
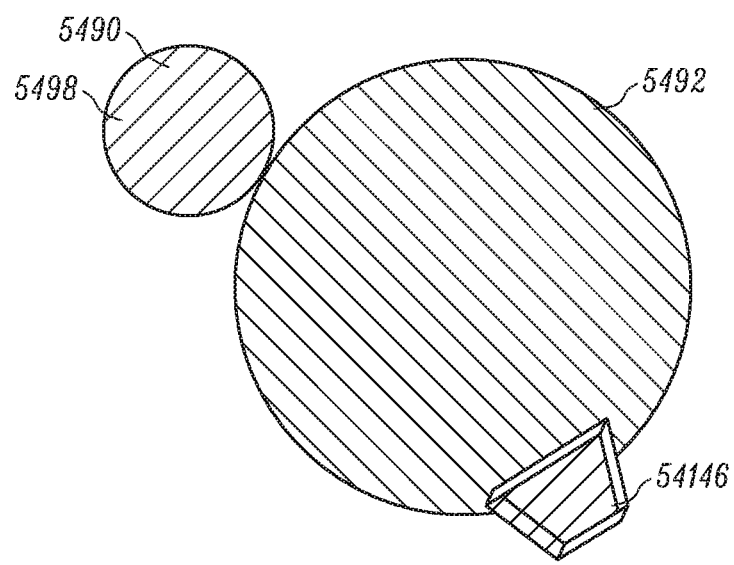
Figure 54C:
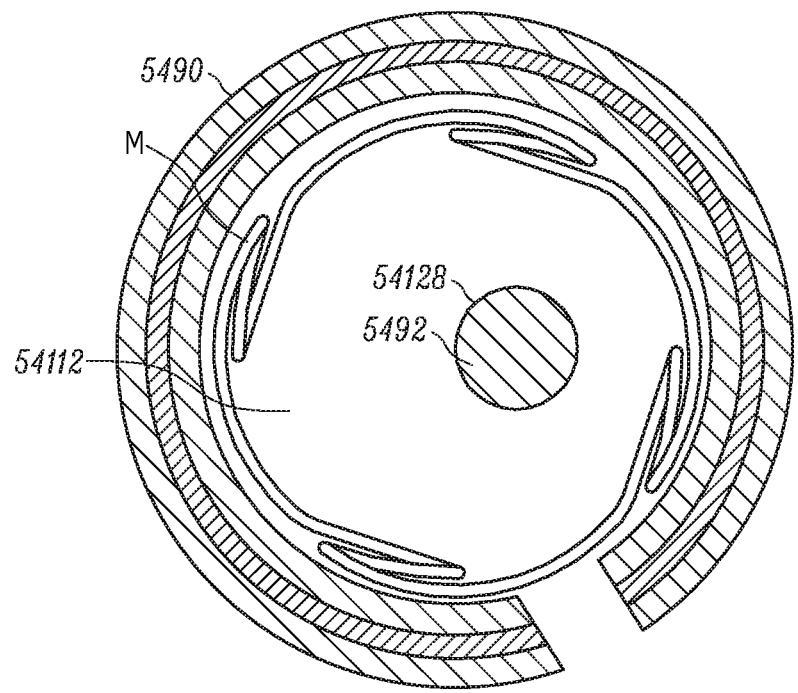
Figure 54D:
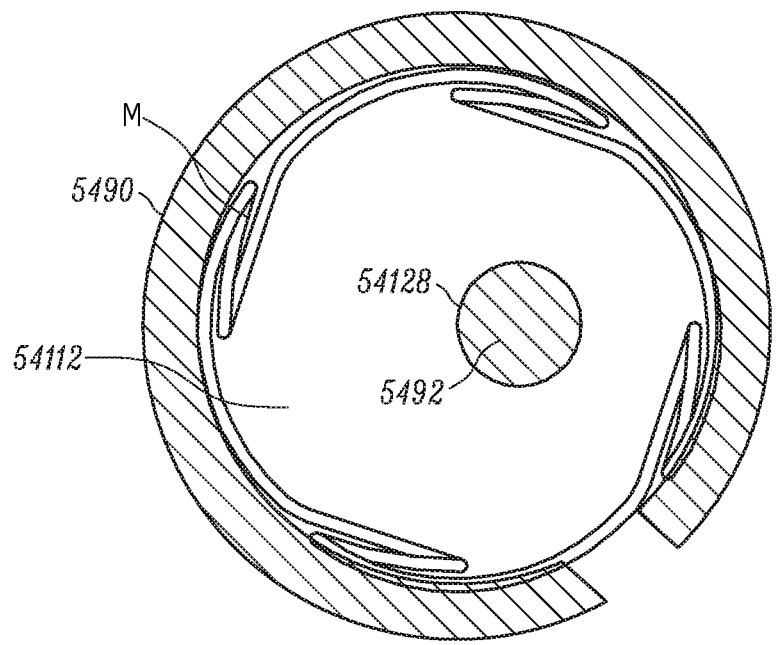
Figure 54E:
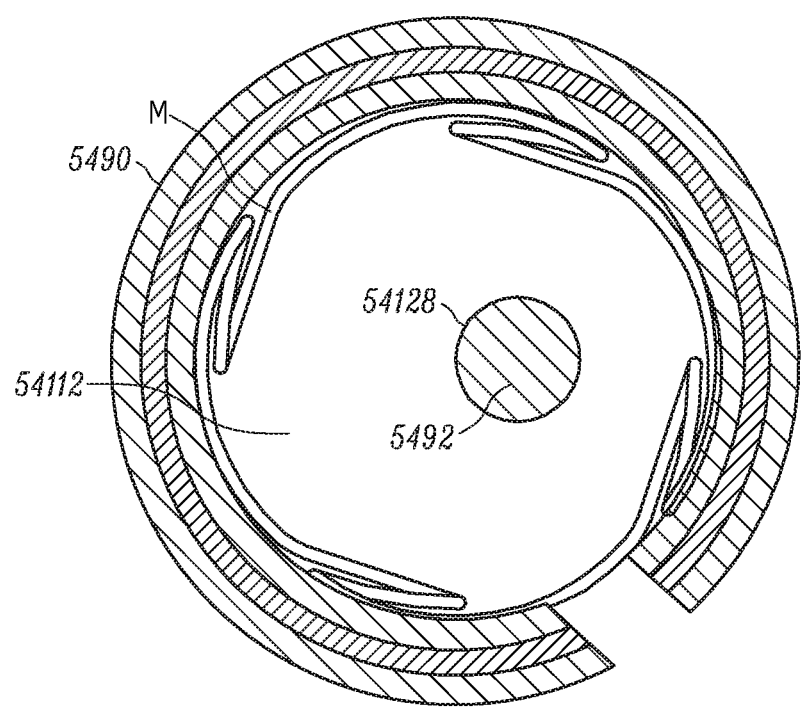
Figure 55B:
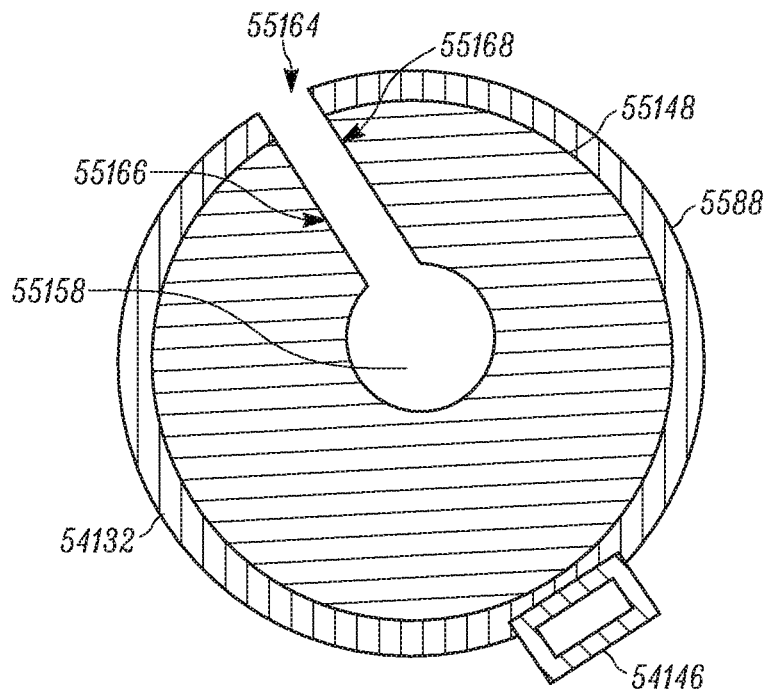
Figure 55C:
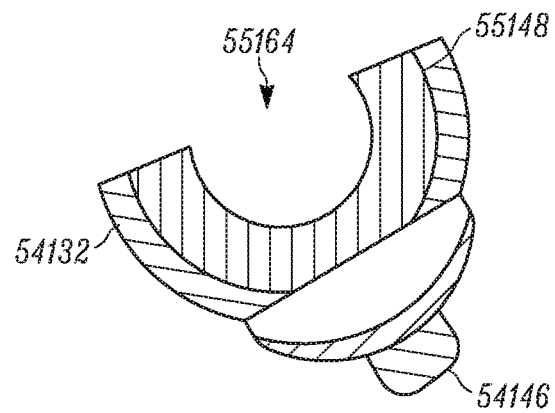
Figure 55D:
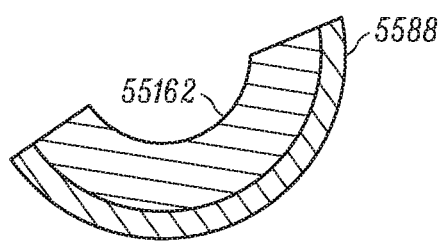

FIGS. 54-72e depict the use of the introducer sheath B 322 to deliver a implant delivery system 5486, which can be a first medical instrument, a second medical instrument, or any other medical instrument, and a balloon dilation device 5588, which can be a first medical instrument, a second medical instrument, or any other medical instrument, toward a target patient tissue site T. FIG. 54 depicts the implant delivery system 5486. The implant delivery system 5486 includes an outer sheath 5490 and a shaft 5492. The outer sheath 5490 has an outer sheath proximal end 5494 and an outer sheath distal end 5496. The outer sheath proximal end 5494 has an outer sheath delivery element 5498. The outer sheath delivery element 5498 may be a stiff wire, or any other appropriate element for delivering the outer sheath 5490 to, or from, a target patient tissue site T. The stiff wire may be, for example, a solid (i.e., non-hollow) structure, such as, but not limited to, a stainless steel or plastic wire. The stiff wire may instead be, for example, an at least partially tubular or hollow structure, such as, but not limited to a catheter with an internal lumen for a guidewire G.

The outer sheath distal end 5496 has an implant holding pod 54100. The implant holding pod 54100 has an implant holding pod proximal end 54102 and an implant holding pod distal end 54104. The implant holding pod 54100 has an implant holding pod body 54105 longitudinally extending between the implant holding pod proximal and distal ends 54102, 54104. The implant holding pod proximal end 54102 has an implant holding pod proximal opening 54106. The implant holding pod proximal opening 54106 of the outer sheath 5490 may face substantially laterally downward. At least a portion of the implant holding pod distal end 54104 may be inwardly tapered.

The implant holding pod distal end 54104 has an implant holding pod open tip 54108. The implant holding pod 54100 has an implant holding pod outer surface 54110 and an implant holding pod lumen 54112. The implant holding pod lumen 54112 of the outer sheath 5490 may extend between the implant holding pod proximal opening 54106 and the implant holding pod open tip 54108. The implant holding pod lumen 54112 is at least partially configured for selectively holding an expandable implant M therein. The expandable implant M may be a stent, an embolization coil, an embolization plug, a shunt closure device, any self-expandable device, any other expandable device, or any combination thereof.

The implant holding pod 54100 has an implant holding pod open slit 54114. The implant holding pod open slit 54114 may extend at least partially between the implant holding pod open tip 54108 and the implant holding pod proximal end 54102. In particular, the implant holding pod open slit 54114 of the outer sheath 5490 may extend between the implant holding pod open tip 54108 and the implant holding pod proximal opening 54106. The implant holding pod open slit 54114 has an implant holding pod open slit first surface 54116 and an implant holding pod open slit second surface 54118. The implant holding pod open slit first surface 54116 oppositely faces and abuts the implant holding pod open slit second surface 54118. The implant holding pod open slit first surface 54116 and the implant holding pod open slit second surface 54118 may be selectively elastically separable. That is, a force may be applied to separate the implant holding pod open slit first surface 54116 and the implant holding pod open slit second surface 54118, as that the implant holding pod open slit first surface 54116 will no longer be abutting the implant holding pod open slit second surface 54118. However, upon the removal of the separating force, the implant holding pod open slit first surface 54116 and the implant holding pod open slit second surface 54118 will return to their original abutting position due to the elastic nature of the material forming the implant holding pod open slit first surface 54116 and the implant holding pod open slit second surface 54118.

The shaft 5492 has a shaft proximal end 54120, a shaft distal end 54122, and a shaft body 54124 that longitudinally extends between the shaft proximal and distal ends 54120, 54122. The shaft proximal end 54120 has a shaft delivery element 54126. The shaft distal end 54122 has an implant delivery element 54128. The implant delivery element 54128 of the shaft has an implant delivery element outer surface 54130 for selectively circumferentially mounting an expandable implant M thereon. The implant delivery element outer surface 54130 has at least one projection 54132 that extends at least partially circumferentially about the implant delivery element outer surface 54130. The projection 54132 of the shaft 5492 is for substantially preventing the egress of an expandable implant M mounted circumferentially about the implant delivery element outer surface

54130 from a desired position on the implant delivery element outer surface 54130. At least one of the shaft body 54124 and the implant delivery element 54128 has a shaft open slit 54134.

The shaft body 54124 has a shaft body proximal end 54136, a shaft body distal end 54138, and a shaft body length 54140 that longitudinally extends between the shaft body proximal and distal ends 54136, 54138. At least one of the shaft body proximal end 54136, the shaft body distal end 54138, and the shaft body length 54140 has a shaft side wall opening 54142. The shaft side wall opening 54142 is in selective fluid communication with the shaft open slit 54134. The shaft open slit 54134 may extend between the shaft side wall opening 54142 and at least one of the shaft body distal end 54138 and the at least one projection 54132. At least a portion of the shaft open slit 54134 and at least a portion of the shaft side wall opening 54142 may collectively form a shaft lumen 54144 for at least partially selectively holding a guidewire G therein. At least one of the shaft body proximal end 54136, the shaft body distal end 54138, and the shaft body length 54140 may have an outer sheath splitter 54146 for facilitating the elastic separation of the implant holding pod open slit first surface 54116 and the implant holding pod open slit second surface 54118. FIGS. 54*a-e* depict cross-sectional views of various points along the implant delivery system 5486, to show structural features of the implant delivery system 5486 of FIG. 54.

FIG. 55 depicts the balloon dilation device 5588. The balloon dilation device 5588 may have a balloon dilation rod 55148. The balloon dilation rod 55148 has a balloon dilation rod proximal end 55150, a balloon dilation rod distal end 55152, and an elongate balloon dilation rod body 55154 that longitudinally extends between the balloon dilation rod proximal and distal ends 55150, 55152. The balloon dilation rod 55148 has a balloon dilation rod outer surface 55156 and a balloon dilation rod lumen 55158.

The balloon dilation rod 55148 has a balloon dilation rod side wall opening 55160. The balloon dilation rod side wall opening 55160 selectively places the balloon dilation rod outer surface 55156 in fluid communication with the balloon dilation rod lumen 55158. The balloon dilation rod distal end 55152 has a balloon dilation rod open tip 55162. The balloon dilation rod lumen 55158 of the balloon dilation device 5588 may extend between the balloon dilation rod side wall opening 55160 and the balloon dilation rod open tip 55162. The balloon dilation rod 55148 has a balloon dilation rod open slit 55164. The balloon dilation rod open slit 55164 may extend between the balloon dilation rod side wall opening 55142 and the balloon dilation rod open tip 55162. The balloon dilation rod open slit 55164 has a balloon dilation rod open slit first surface 55166 and a balloon dilation rod open slit second surface 55168. The balloon dilation rod open slit first surface 55166 oppositely faces and abuts the balloon dilation rod open slit second surface 55168. The balloon dilation rod open slit first surface 55166 and the balloon dilation rod open slit second surface 55168 are selectively elastically separable.

An expandable balloon 55170 may be positioned on at least one of the balloon dilation rod body 55154 and the balloon dilation rod distal end 55152. The expandable balloon 55170 may have a balloon open slit 55172 that at least partially extends for at least a partial length of the expandable balloon 55170. The balloon open slit 55172 may be aligned with the balloon dilation rod open slit 55164. The balloon dilation device 5588 may include a balloon inflation channel 55174 that longitudinally extends between the balloon dilation rod proximal end 55150 and a balloon inflation side wall opening 55176. The balloon inflation channel 55174 may be placed in fluid communication with an outside fluid source (not shown) in any desired manner. The balloon inflation side wall opening 55176 selectively places a balloon expanding chamber 55178 in fluid communication with at least one of the balloon inflation channel 55174 and the outside fluid source. The balloon inflation channel 55174 may be separate from the balloon dilation rod lumen 55158.

The balloon dilation rod distal end 55152 may have a nosecone 55180. The nosecone 55180 may point, or narrow, toward a longitudinally distal direction (shown as an arrow DI in FIG. 55). The balloon dilation rod distal end 55152 may have an outer sheath splitter 54146 for facilitating the elastic separation of another device having an open slit. For example, the outer sheath splitter 54146 may facilitate the elastic separation of the implant holding pod open slit first surface 54116 and the implant holding pod open slit second surface 54118 when the balloon dilation device 5588 is used in conjunction with the outer sheath 5490. The outer sheath splitter 54146 of the balloon dilation device 5588 may be arrow-shaped. The arrow-shaped outer sheath splitter 54146 may point toward the longitudinally distal direction. FIGS. 55*a-d* depict cross-sectional views of various points along the balloon dilation device 5588, to show the structural features of the balloon dilation device 5588 in FIG. 55.

Figure 56:
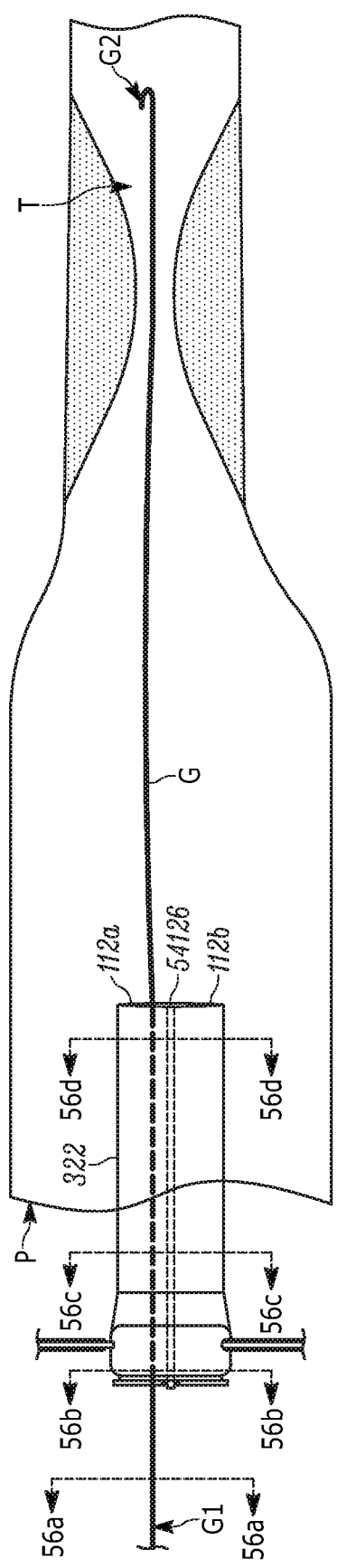
Figure 56A:
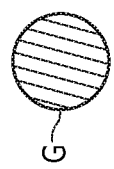
Figure 56B:
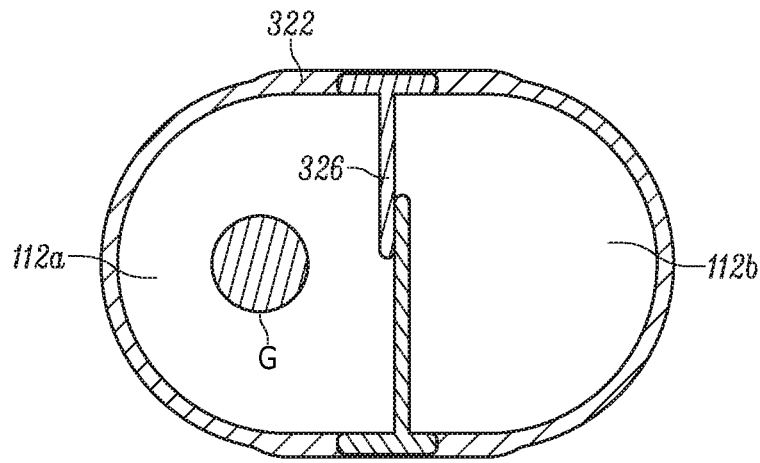
Figure 56C:
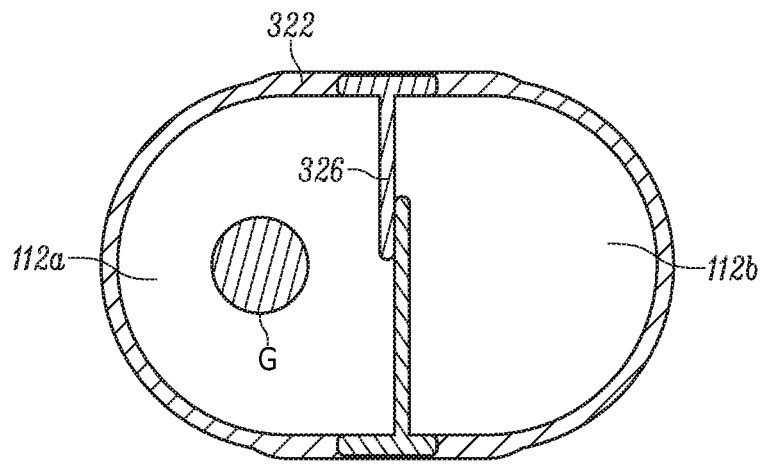
Figure 56D:
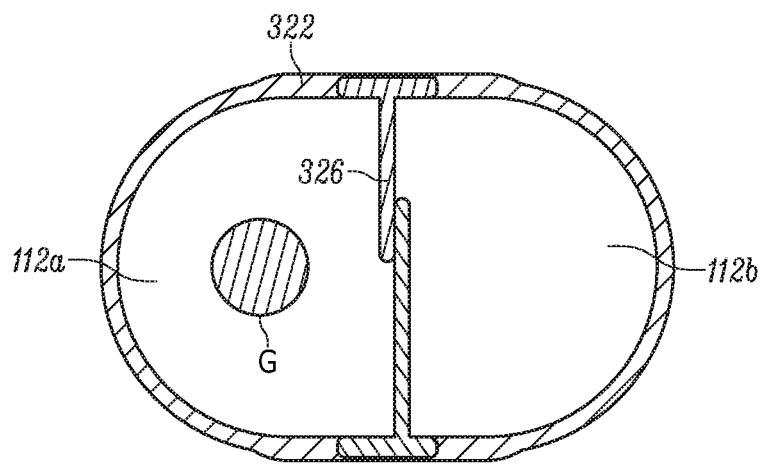

A guidewire distal end G2 is inserted into a target patient tissue site T through a patient tissue access point P. A guidewire proximal end G1 is directed through a first sheath lumen 112 (shown here as the first sheath lumen 112*a*) of the plurality of sheath lumens 112 (shown here as the sheath lumens 112*a* and 112*b*). As shown in FIG. 56, the introducer sheath B 322 is directed toward the target patient tissue site T along the guidewire G. FIGS. 56*a-d* depict cross-sectional views of various points along the introducer sheath B 322 and the guidewire G, to show the arrangement of the introducer sheath B 322 and the guidewire G in FIG. 56.

A collapsed expandable implant M may be placed in operative engagement with the implant delivery element 54128. In particular, the expandable implant M may be mounted circumferentially about the implant delivery element outer surface 54130, in any desired manner. With the expandable implant M mounted to the implant delivery element outer surface 54130, and the expandable implant M in a collapsed condition, at least one of the shaft body 54124, the implant delivery element 54128, and the expandable implant M may be collectively inserted at least partially into the implant holding pod lumen 54112. Alternatively, instead of mounting the expandable implant M to the implant delivery element outer surface 54130 prior to inserting at least a portion of the shaft 5492 into the implant holding pod lumen 54112, a collapsed expandable implant M may be placed within the implant holding pod lumen 54112 prior to inserting at least a portion of the shaft 5492 into the implant holding pod lumen 54112. In such case, after at least a portion of the shaft 5492 is inserted into the implant holding pod lumen 54112, the collapsed expandable implant M may be placed in operative engagement with the implant delivery element 54128 by mounting the expandable implant M to the implant delivery element outer surface 54130.

Figure 57:
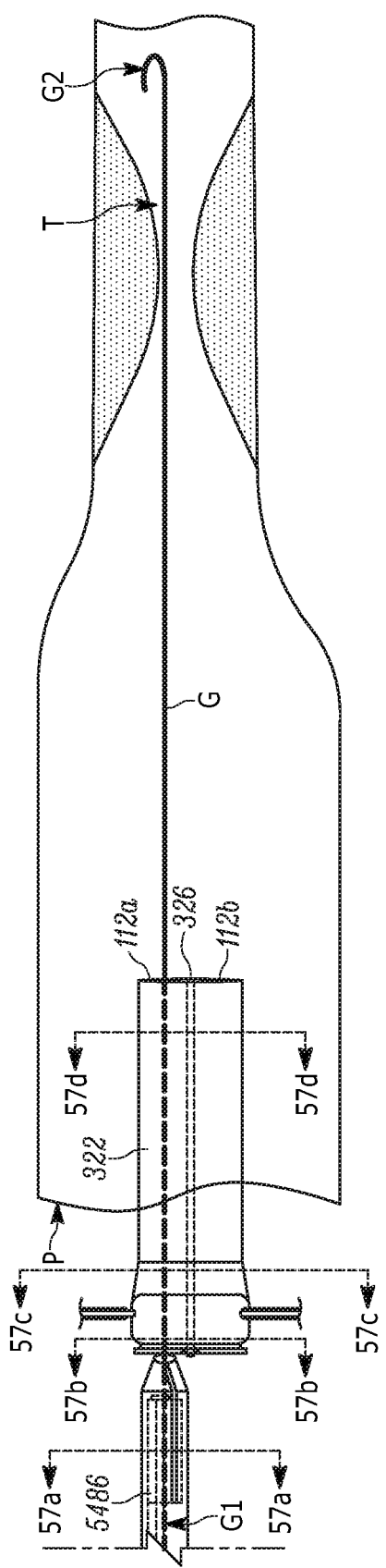
Figure 57A:
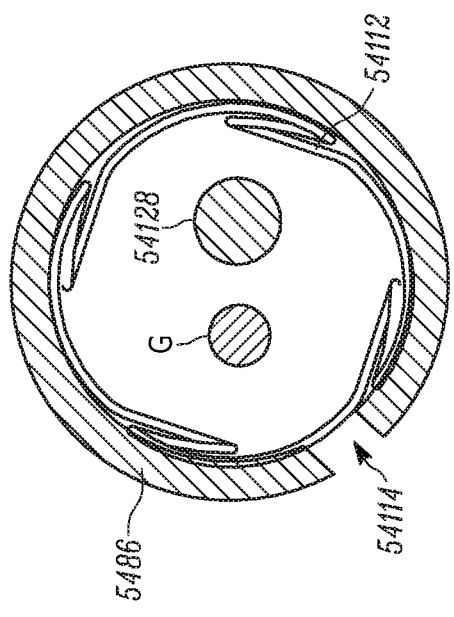
Figure 57B:
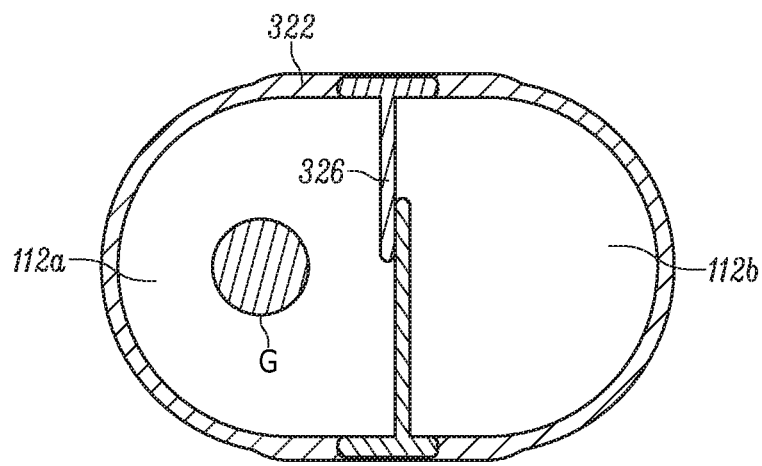
Figure 57C:
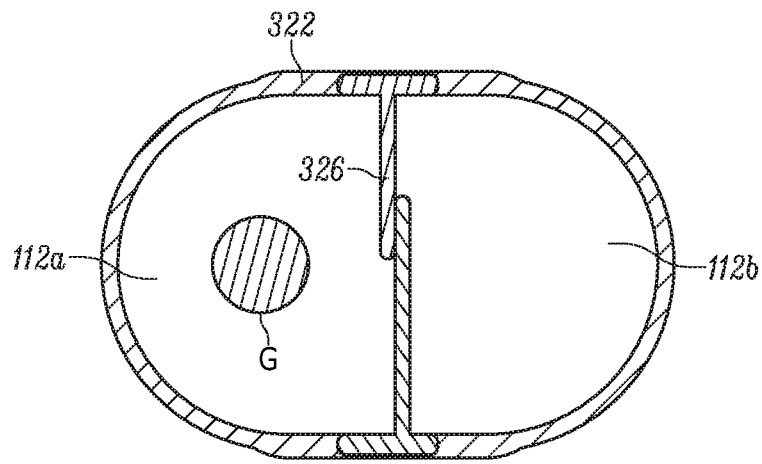
Figure 57D:
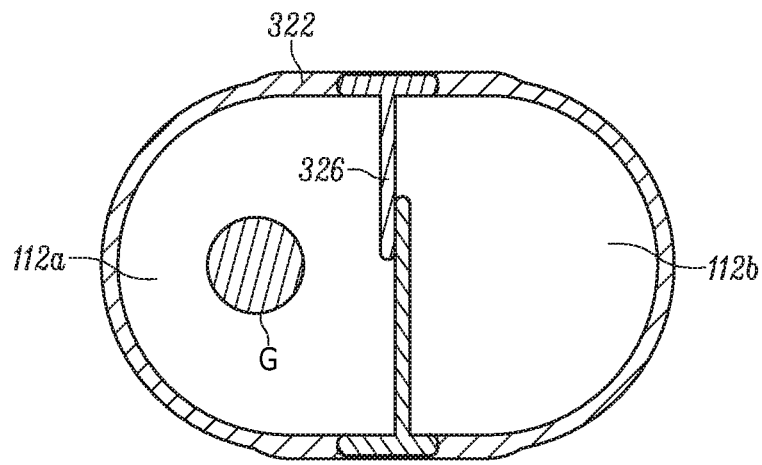
Figure 58:
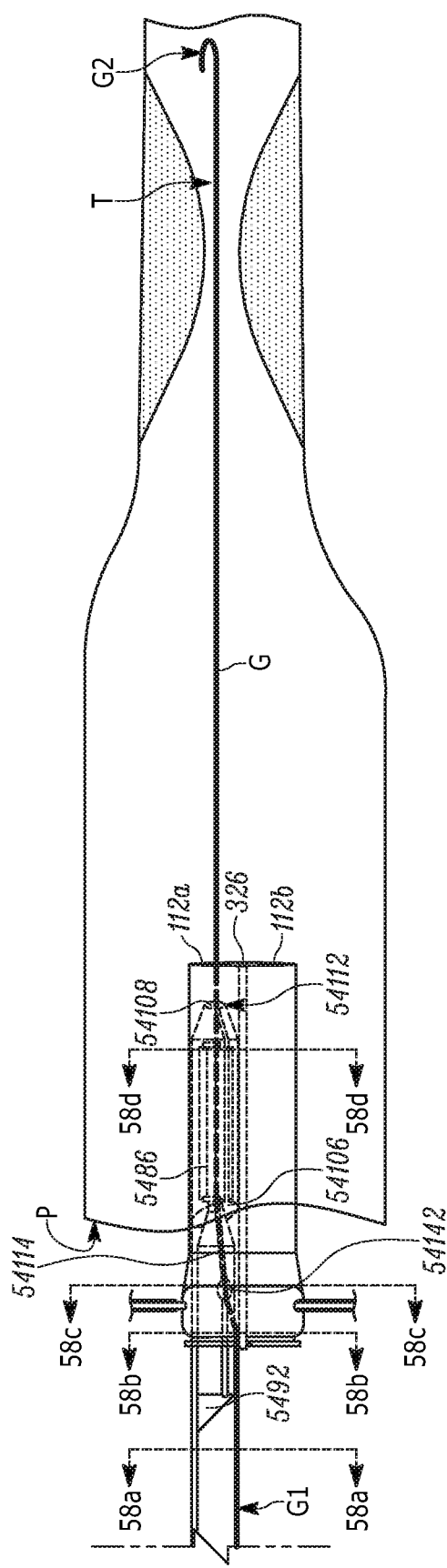
Figure 58A:
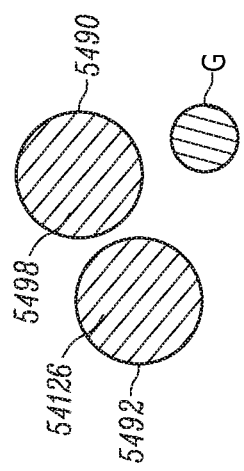
Figure 58B:
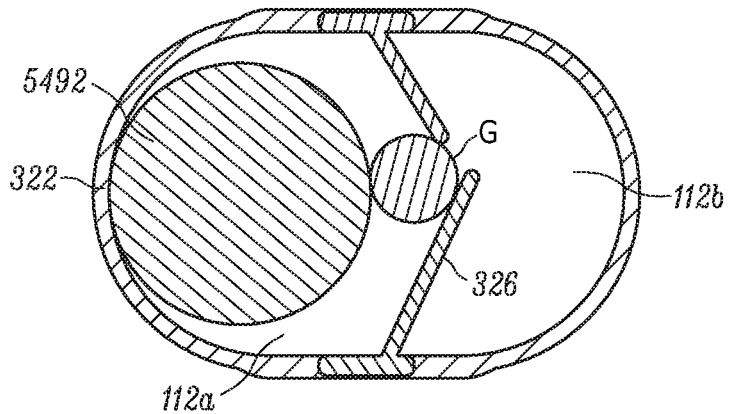
Figure 58C:
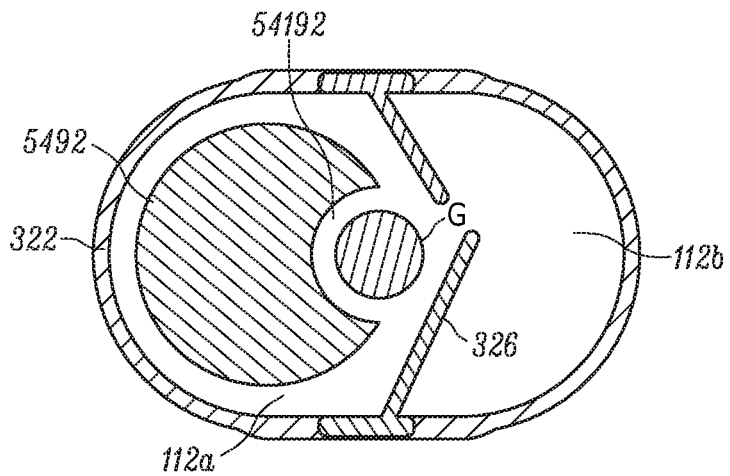
Figure 58D:
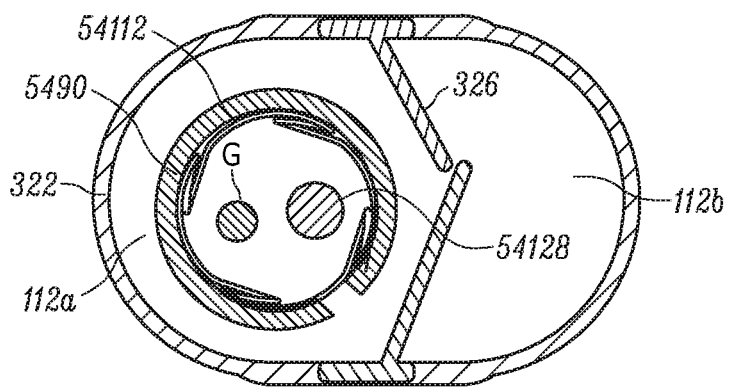

With at least a portion of the shaft 5492 and the expandable implant M at least partially inserted in the implant holding pod lumen 54112, the shaft 5492 may be aligned in the implant holding pod lumen 54112 with at least a portion of the shaft open slit 54134 being laterally spaced from the implant holding pod open slit 54114. As shown in FIGS. 57 and 58, the guidewire proximal end G1 is directed through the implant delivery system 5486. In particular, the guidewire proximal end G1 may be directed through the implant holding pod open tip 54108, through at least a portion of the implant holding pod lumen 54112, through the implant holding pod proximal opening 54106 and the shaft lumen 54144, and out from the shaft 5492, such as through the shaft side wall opening 54142. FIGS. 57*a-d* depict cross-sectional views of various points along the introducer sheath B 322, the implant delivery system 5486, and the guidewire G, to show the arrangement of the introducer sheath B 322, the implant delivery system 5486, and the guidewire G in FIG. 57.

Figure 59:
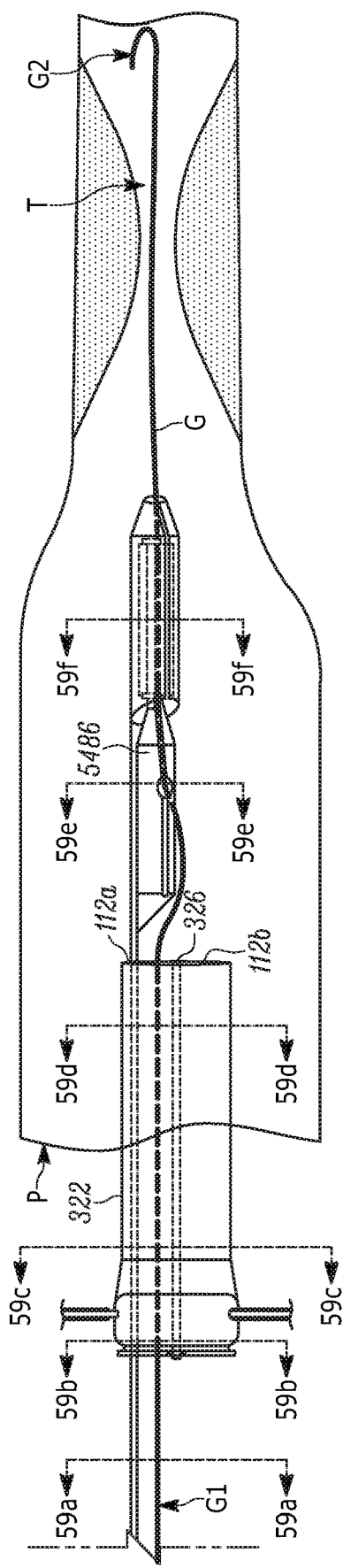
Figure 59A:
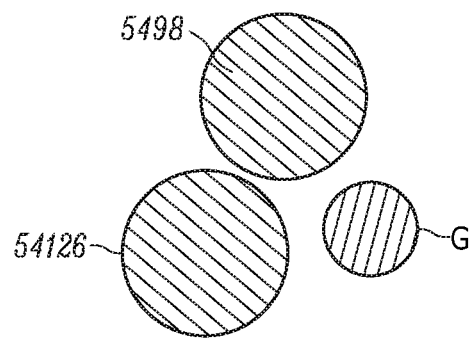
Figure 59B:
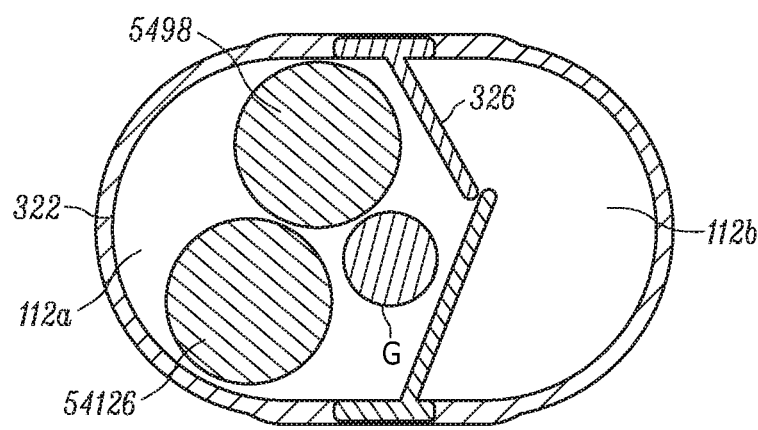
Figure 59C:
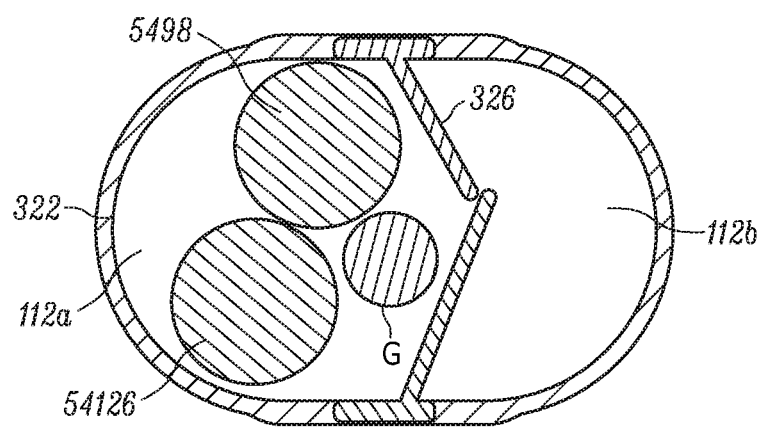
Figure 59D:
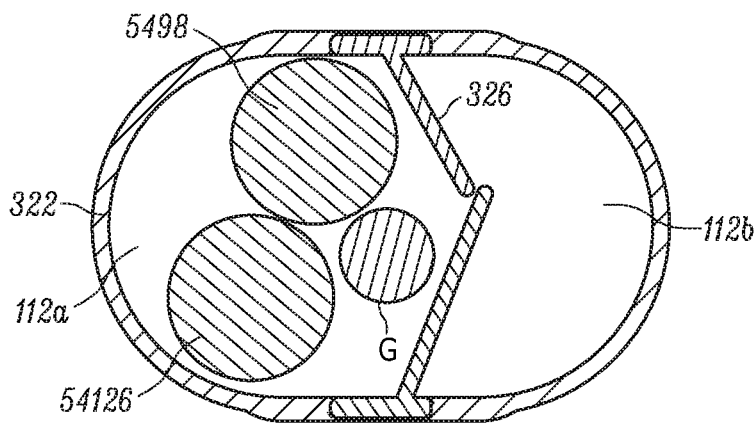
Figure 59E:
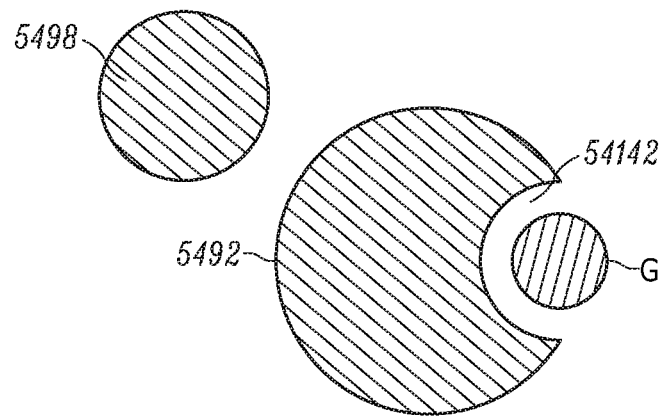
Figure 59F:
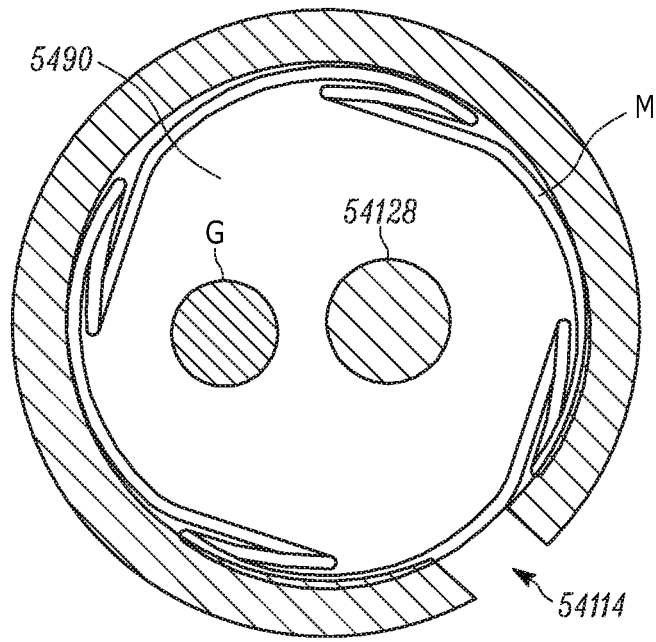

As shown in FIGS. 58 and 59, the implant delivery system 5486 is directed toward the target patient tissue site T along the guidewire G and at least partially through the first sheath lumen 112*a*. As the implant delivery system 5486 is at least partially directed through the first sheath lumen 112*a*, portions of the implant delivery system 5486 may cause portions of the septum B 326 to at least partially deflect from the biased condition due to portions of the implant delivery system 5486 pushing against the septum B 326 (FIGS. 58*b-d*, 59*b-d*). FIGS. 58*a-d* depict cross-sectional views of various points along the introducer sheath B 322, the implant delivery system 5486, and the guidewire G, to show the arrangement of the introducer sheath B 322, the implant delivery system 5486, and the guidewire G in FIG. 58. FIGS. 59*a-f* depict cross-sectional views of various points along the introducer sheath B 322, the implant delivery system 5486, and the guidewire G, to show the arrangement of the introducer sheath B 322, the implant delivery system 5486, and the guidewire G in FIG. 59.

Figure 60:
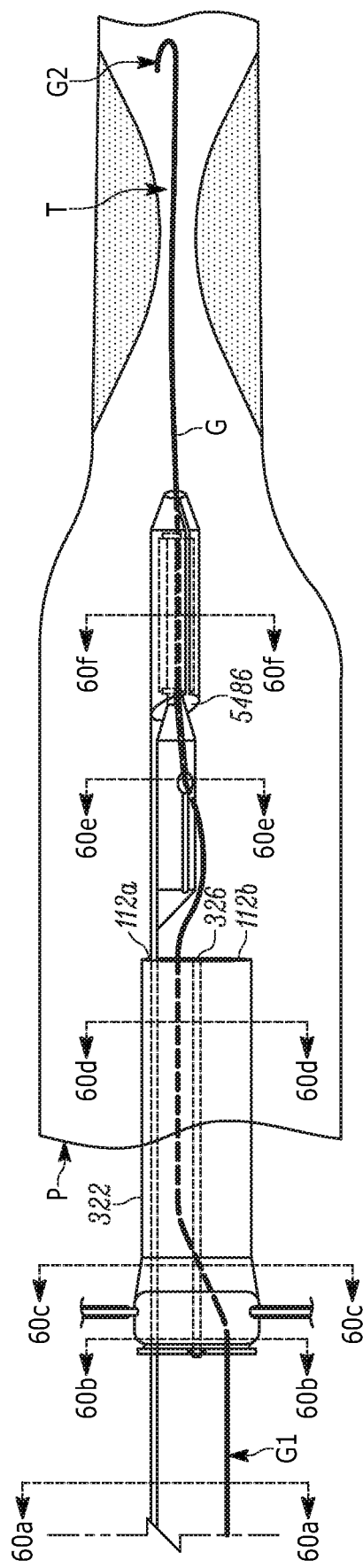
Figure 60A:
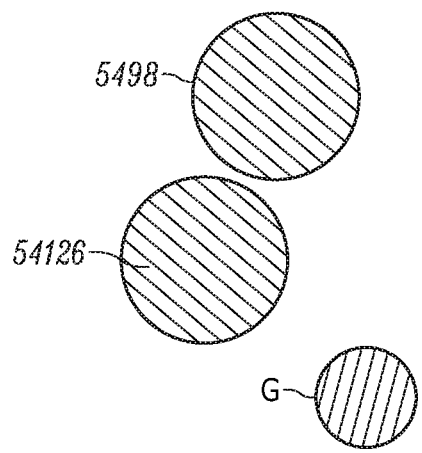
Figure 60B:
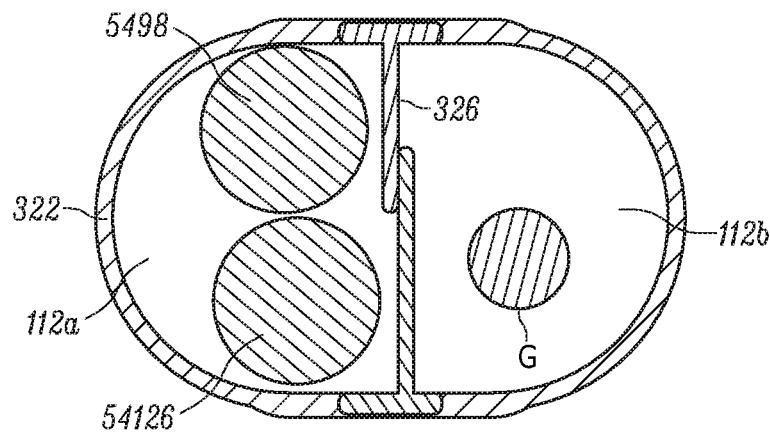
Figure 60C:
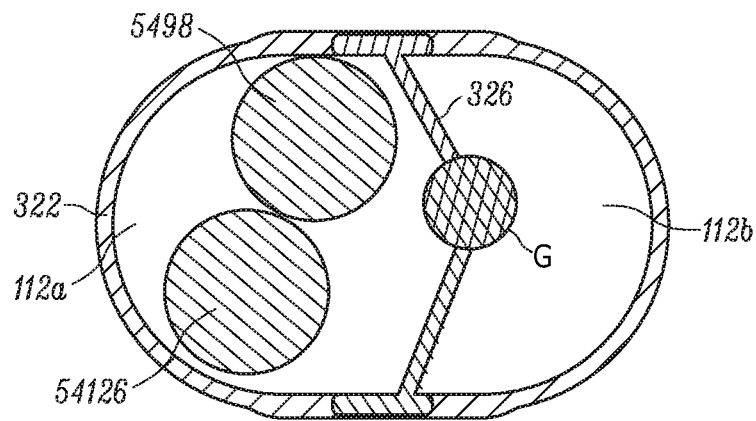
Figure 60D:
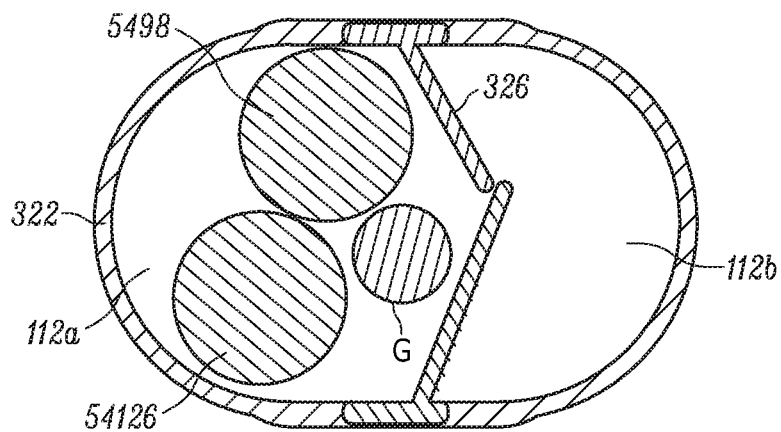
Figure 60E:
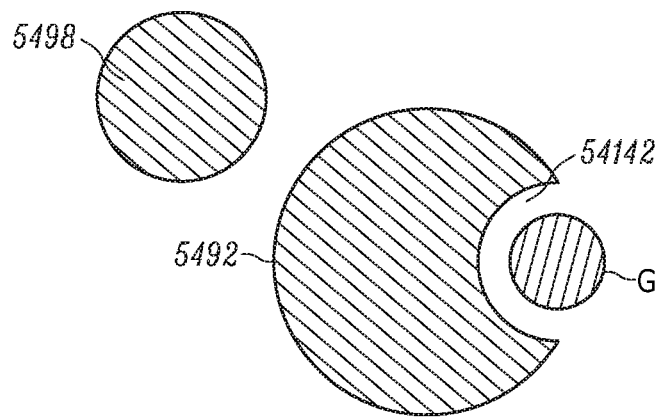
Figure 60F:
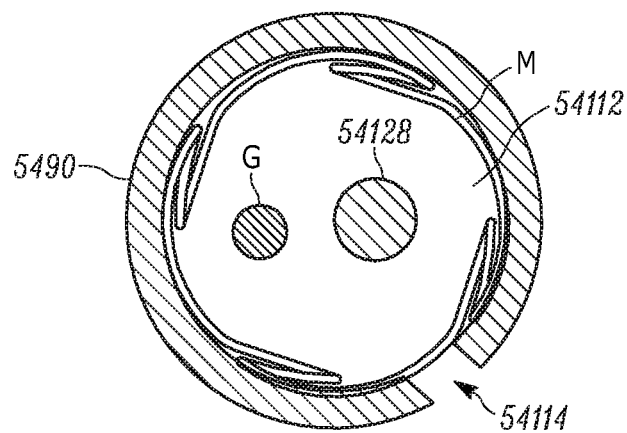
Figure 61:
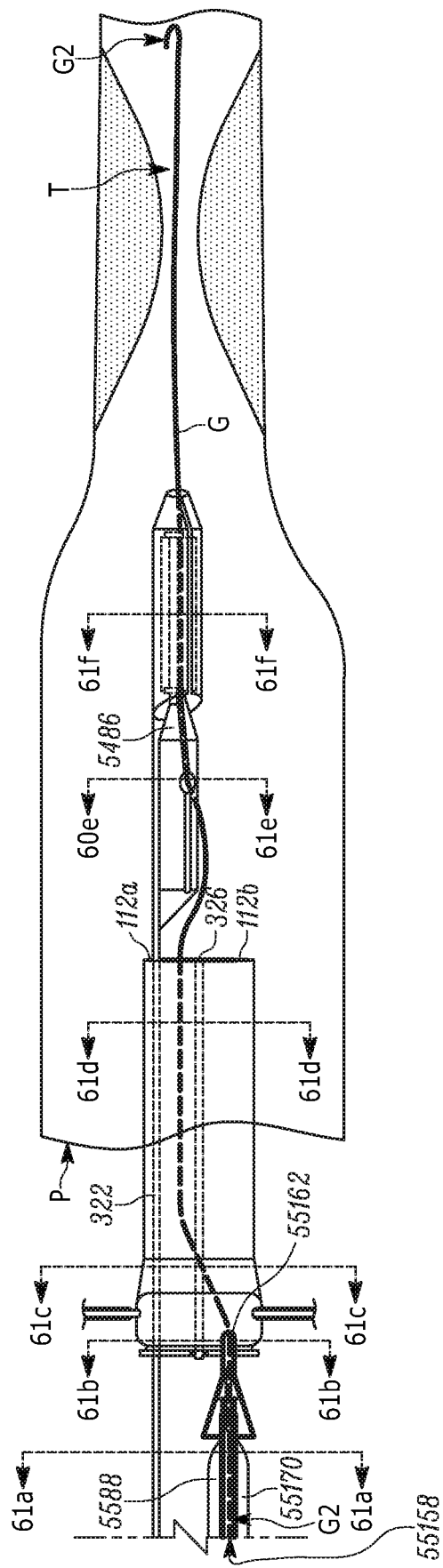
Figure 61A:
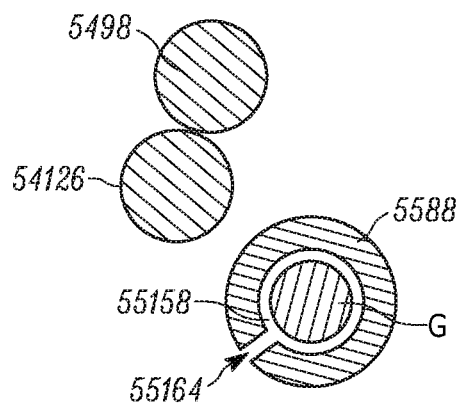
Figure 61B:
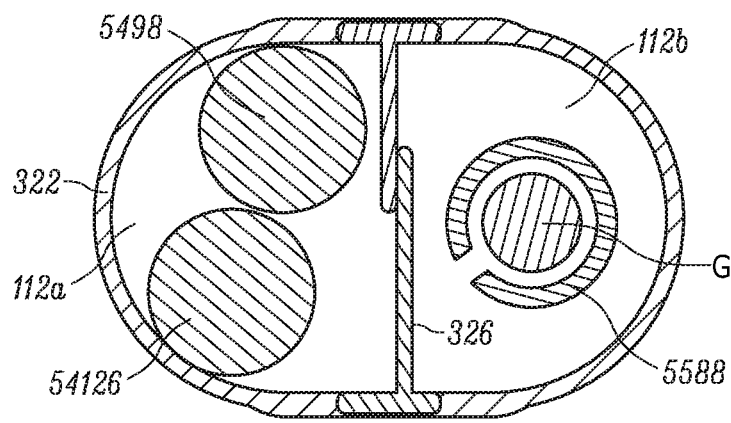
Figure 61C:
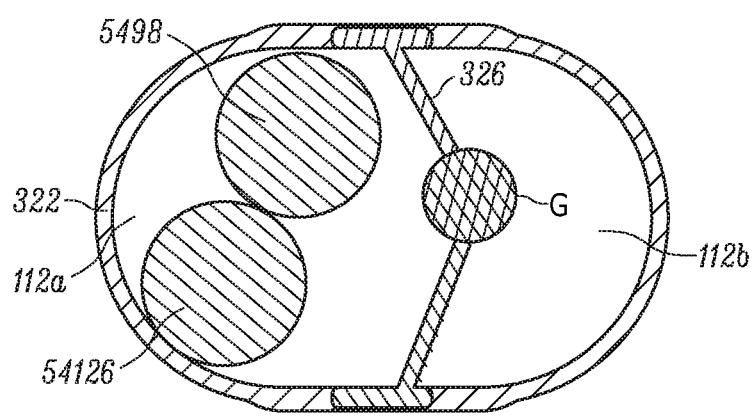
Figure 61D:
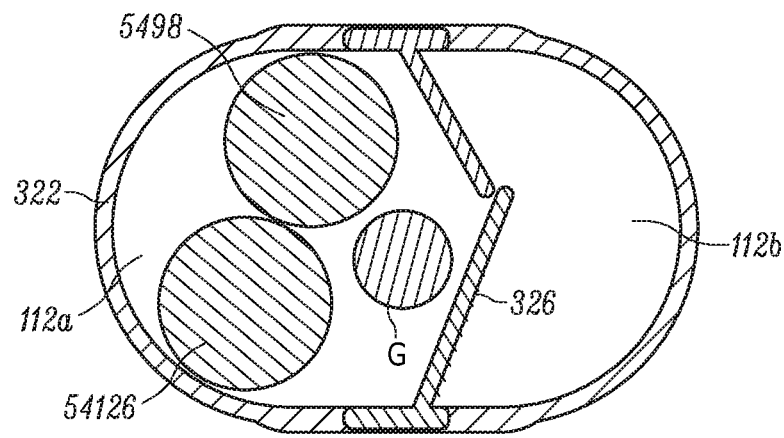
Figure 61E:
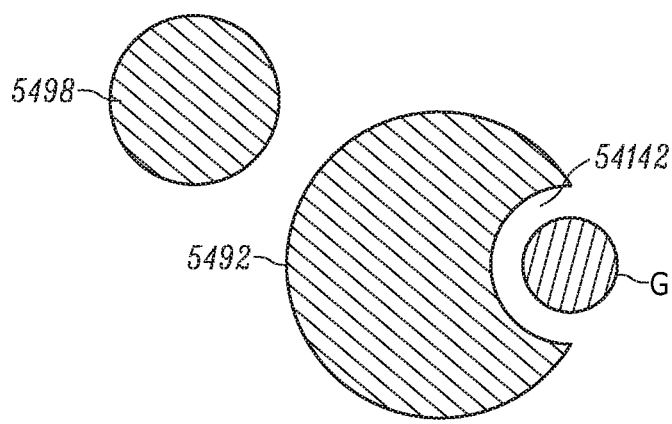
Figure 61F:
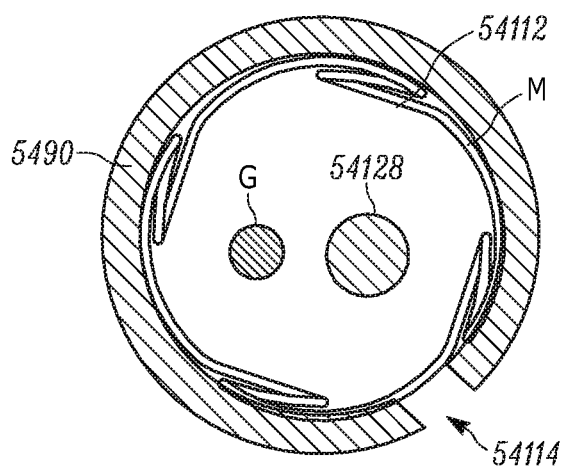

As shown in FIG. 60, at least a portion of the guidewire proximal end G1 may be urged from the first sheath lumen 112*a* to a second sheath lumen 112 (shown here as the second sheath lumen 112*b*). FIGS. 60*a-f* depict cross-sectional views of various points along the introducer sheath B 322, the implant delivery system 5486, and the guidewire G, to show the arrangement of the introducer sheath B 322, the implant delivery system 5486, and the guidewire G in FIG. 60. As shown in FIG. 61, the guidewire proximal end G1 is at least partially directed through the balloon dilation device 5588, when provided. In particular, the guidewire proximal end G1 is directed into the balloon dilation rod open tip 55162, through at least a portion of the balloon dilation rod lumen 55158, and out of the balloon dilation device 5588, such as through the balloon dilation rod side wall opening 55160. FIGS. 61*a-f* depict cross-sectional views of various points along the introducer sheath B 322, the implant delivery system 5486, the balloon dilation device 5588, and the guidewire G, to show the arrangement of the introducer sheath B 322, the implant delivery system 5486, the balloon dilation device 5588, and the guidewire G in FIG. 61.

Figure 62:
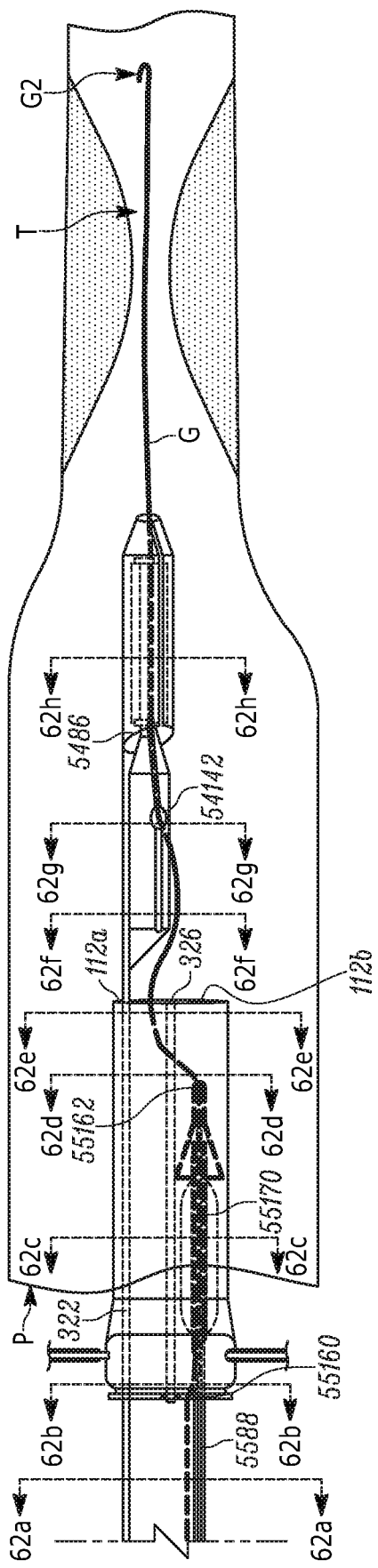
Figure 62A:
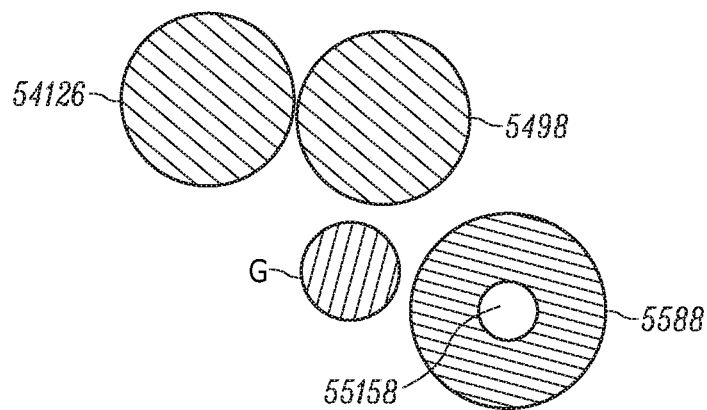
Figure 62B:
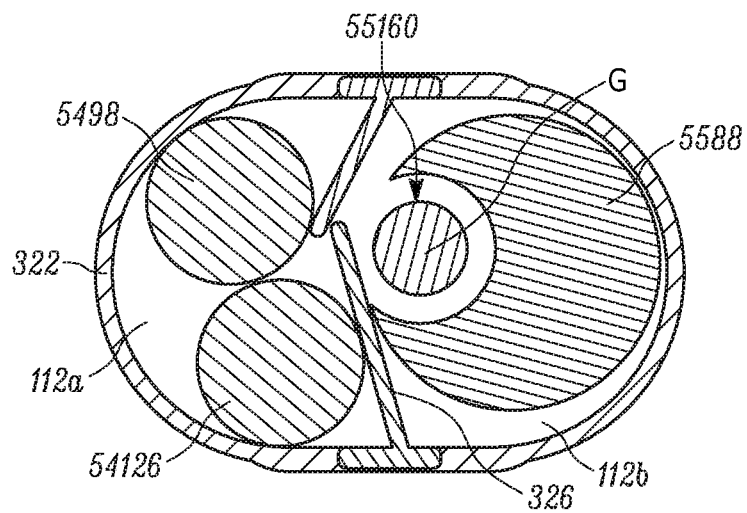
Figure 62C:
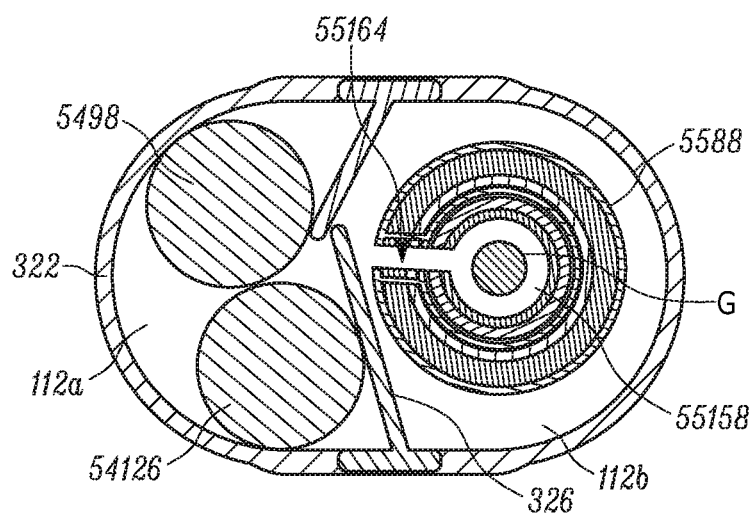
Figure 63:
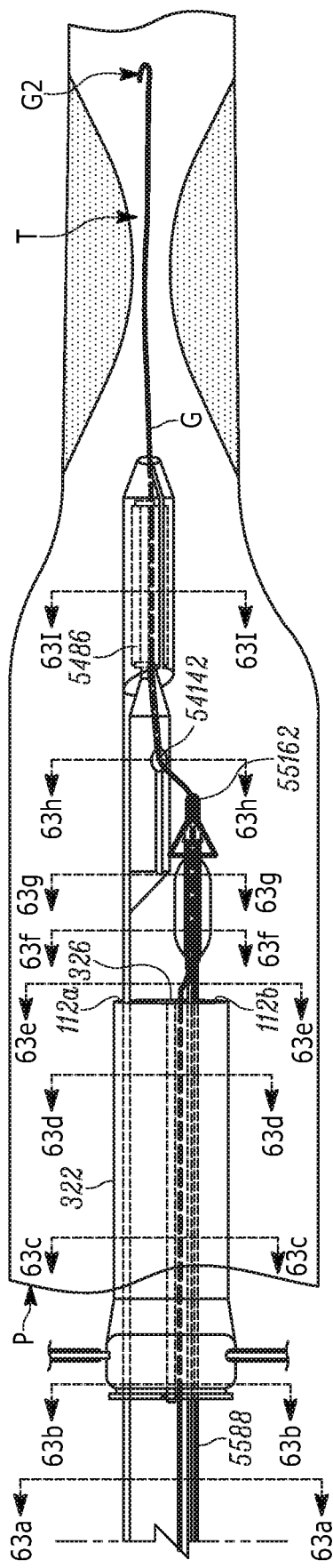
Figure 63A:
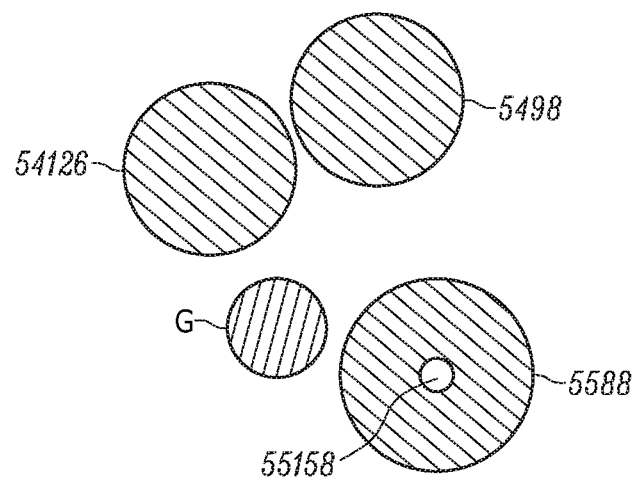
Figure 63B:
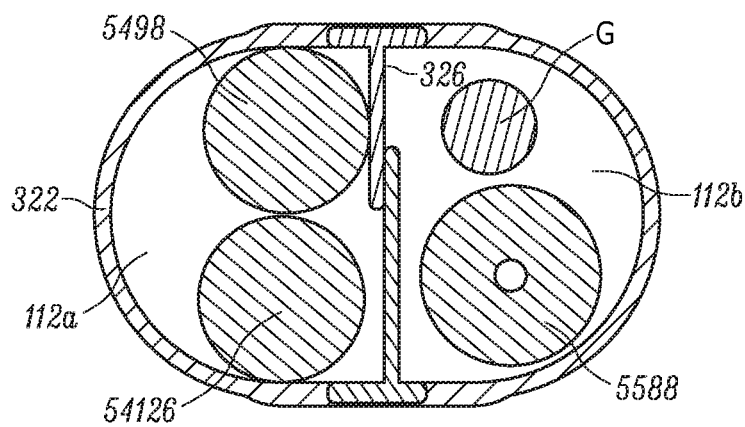
Figure 63C:
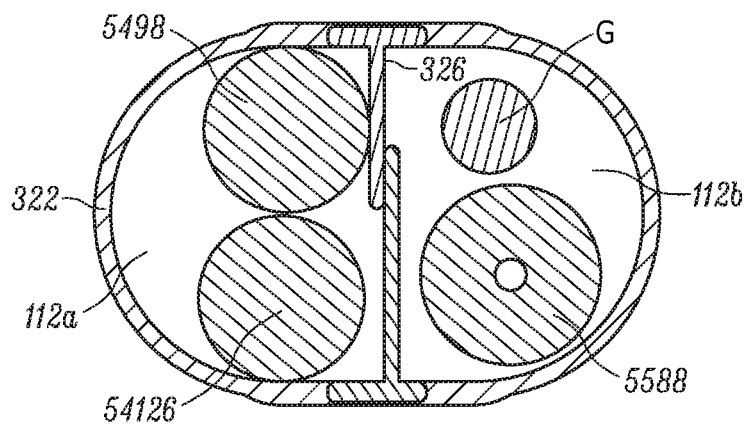
Figure 63D:
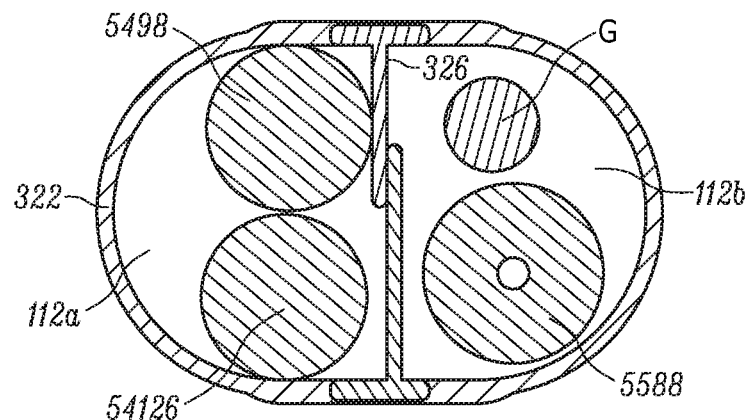
Figure 63E:
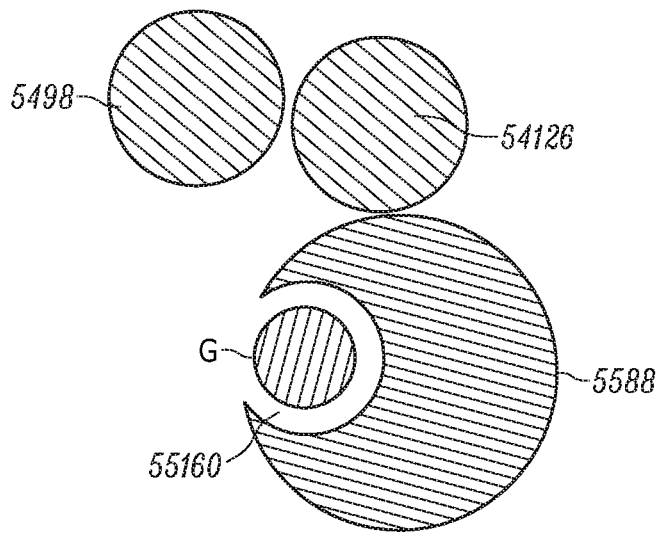
Figure 63F:
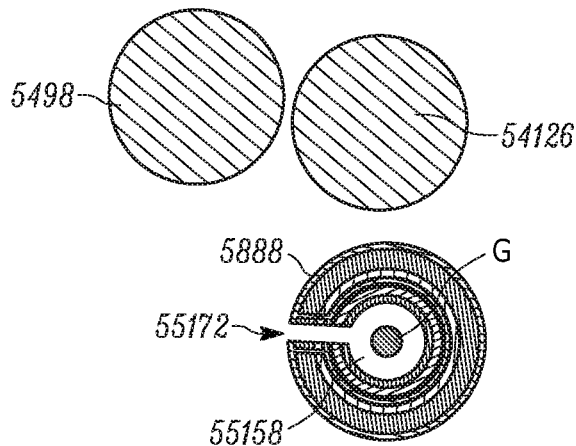
Figure 63G:
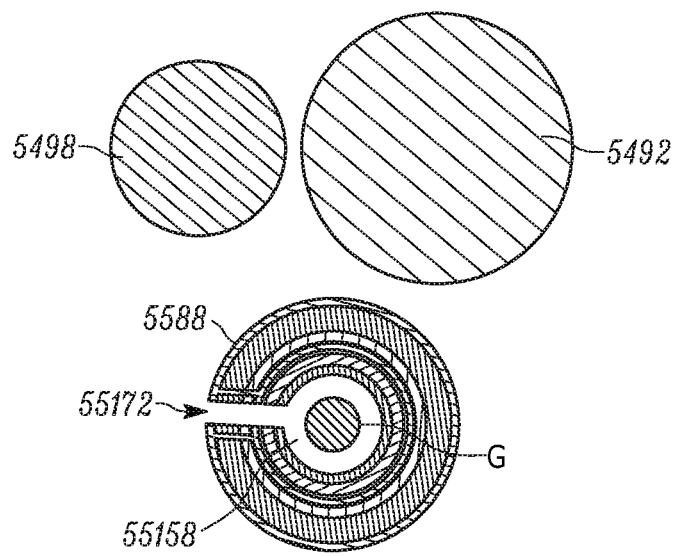
Figure 63H:
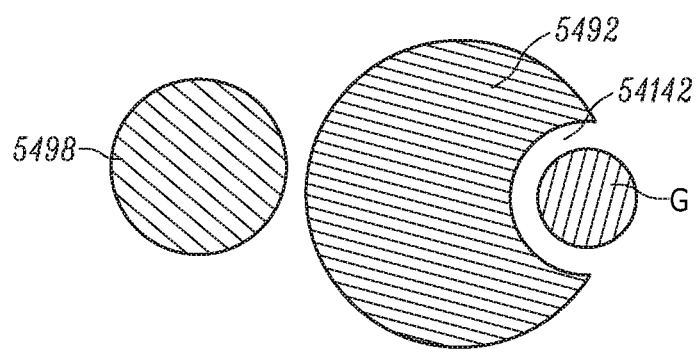
Figure 63I:
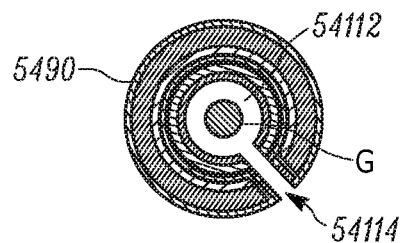

As shown in FIGS. 62 and 63, the balloon dilation device 5588 is directed toward the target patient tissue site T along the guidewire G and at least partially through the second sheath lumen 112*b* until the balloon dilation rod open tip 55162 is adjacent to the shaft side wall opening 54142. The balloon dilation device 5588 urges the guidewire G from the first sheath lumen 112*a* to the second sheath lumen 112*b* as the balloon dilation device 5588 moves at least partially through the second sheath lumen 112*b*, while the guidewire G is maintained at the target patient tissue site T. The balloon dilation device 5588 urges the guidewire G from the first sheath lumen 112*a* to the second sheath lumen 112*b* by causing at least a portion of the guidewire G to be urged into at least a portion of the septum B 326 to selectively deflect at least a portion of the septum B 326 from the biased condition. The deflection of the septum B 326 at least partially providing fluid communication between the first and second sheath lumens 112*a*, 112*b* so that the portion of the guidewire G being urged into the septum B 326 passes into the second sheath lumen 112*b* from the first sheath lumen 112*a*.

Figure 62D:
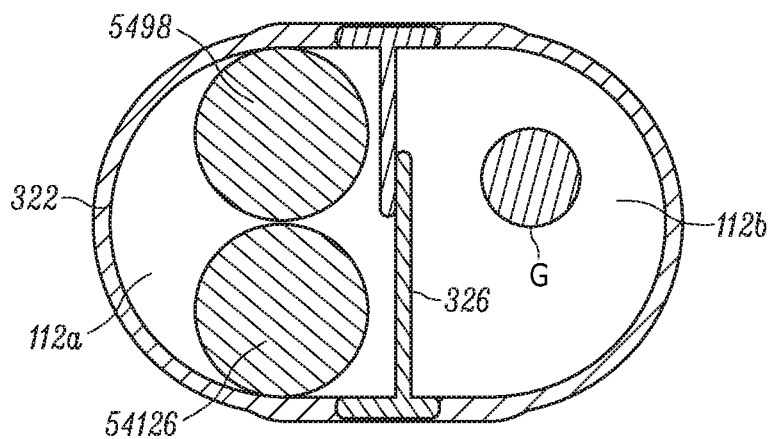
Figure 62E:
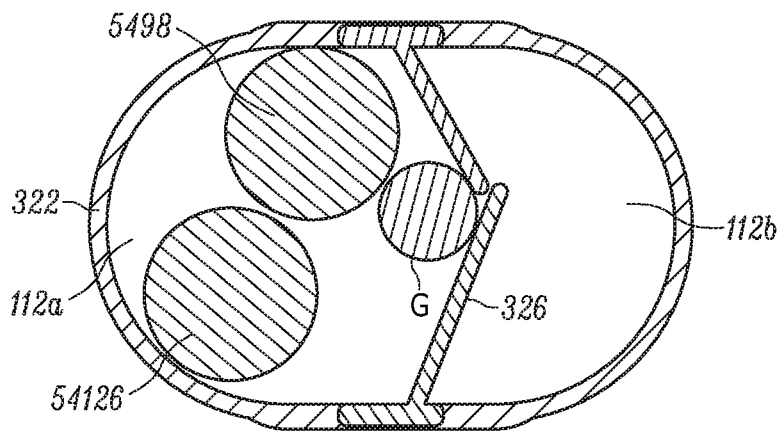
Figure 62F:
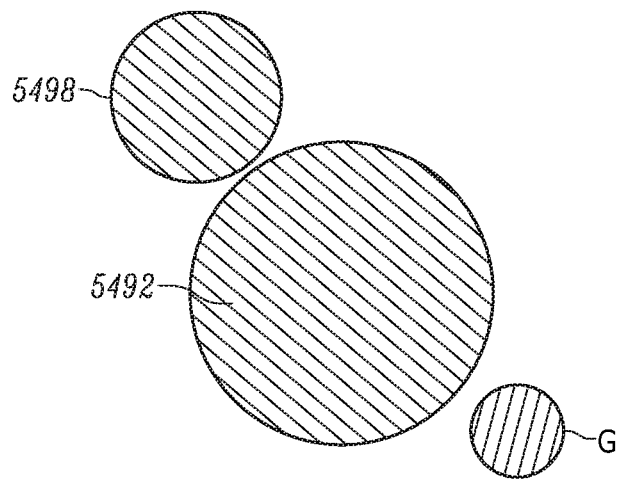
Figure 62G:
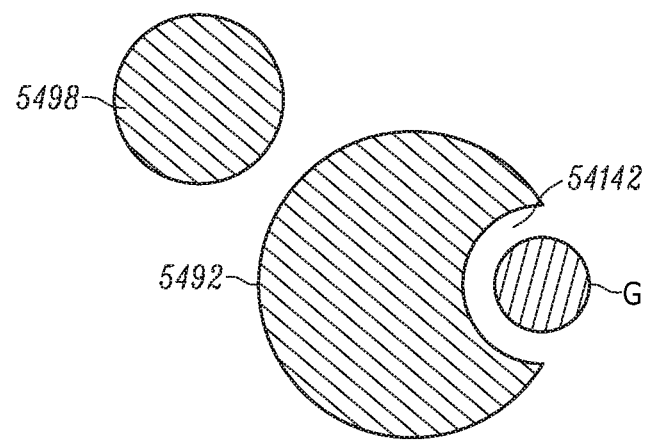
Figure 62H:
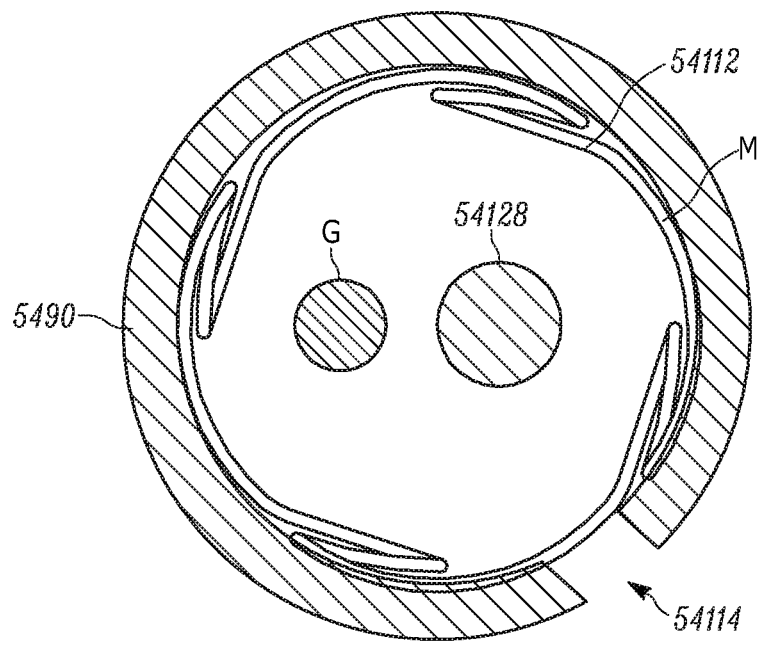

FIGS. 62*a-h* depict cross-sectional views of various points along the introducer sheath B 322, the implant delivery system 5486, the balloon dilation device 5588, and the guidewire G, to show the arrangement of the introducer sheath B 322, the implant delivery system 5486, the balloon dilation device 5588, and the guidewire G in FIG. 62. FIGS. 62*b-e* also show that at least a portion of the septum B 326 along a length of the septum B 326 is capable of being moved from the biased condition (FIGS. 62*b*, 62*c*, 62*e*) while at least one other portion of the septum B 326 along the length of the septum B 326 is maintained in the biased condition (FIG. 62*d*). Further, FIGS. 62*b-e* show that at least a portion of the septum B 326 along a length of the septum B 326 is capable of being moved from the biased condition in a first direction (FIGS. 62*b*, 62*c*) while at least one other portion of the septum B 326 along the length of the septum B 326 is at least one of in the biased condition (FIG. 62*d*) and moved in a second direction (FIG. 62*e*), different from the first direction. FIGS. 63*a-i* depict cross-sectional views of various points along the introducer sheath B 322, the implant delivery system 5486, the balloon dilation device 5588, and the guidewire G, to show the arrangement of the introducer sheath B 322, the implant delivery system 5486, the balloon dilation device 5588, and the guidewire G in FIG.

Figure 64:
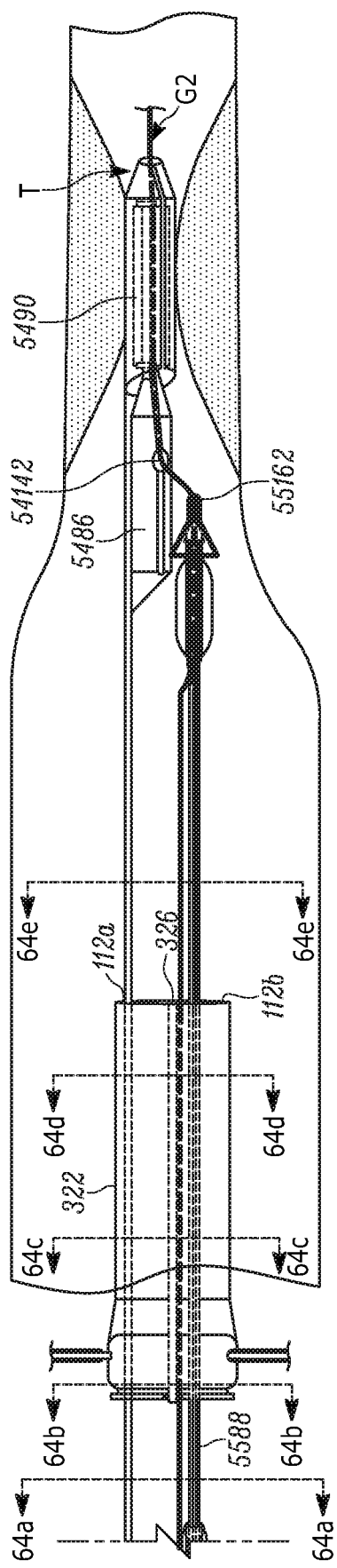
Figure 64A:
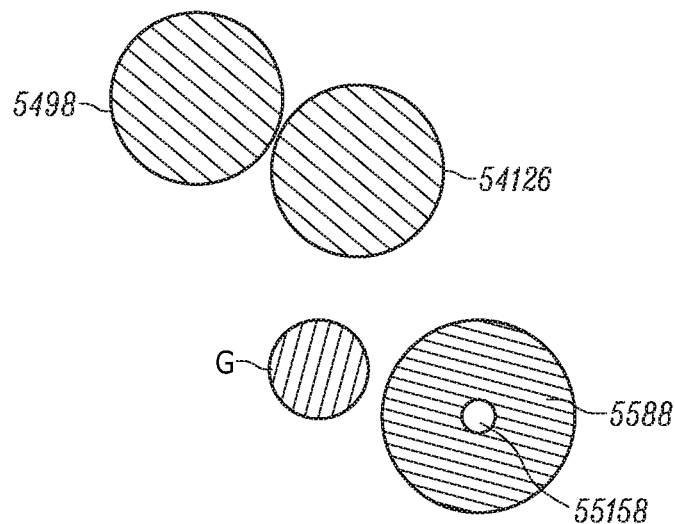
Figure 64B:
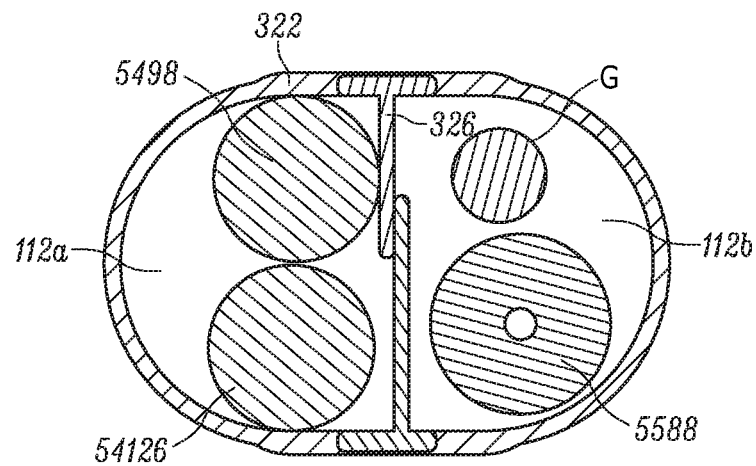
Figure 64C:
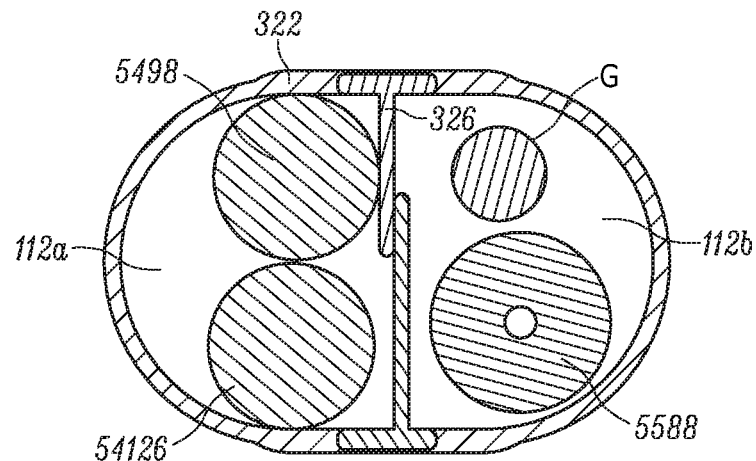
Figure 64D:
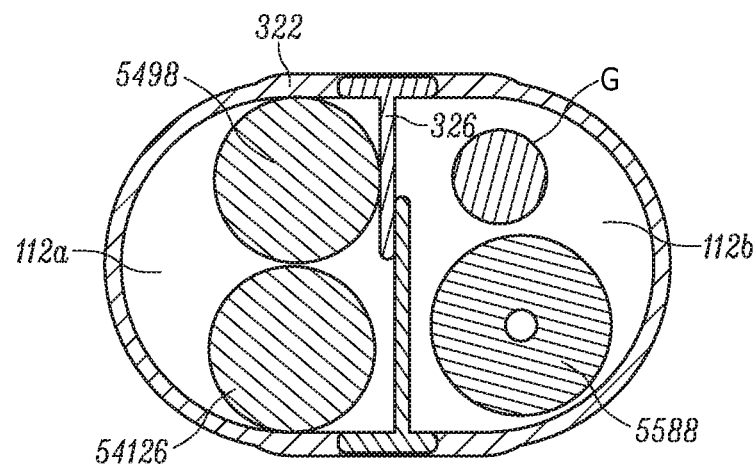
Figure 64E:
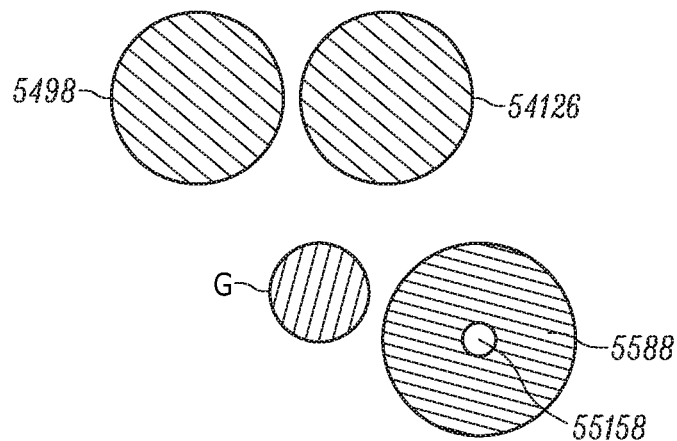
Figure 66B:
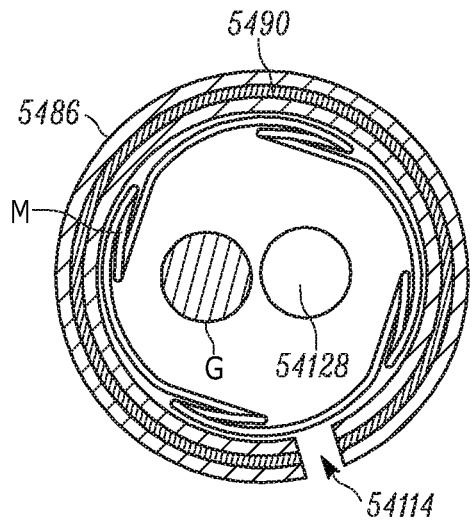
Figure 66C:
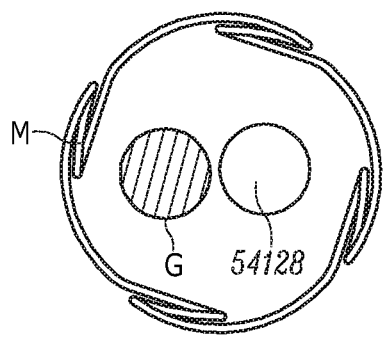
Figure 66D:
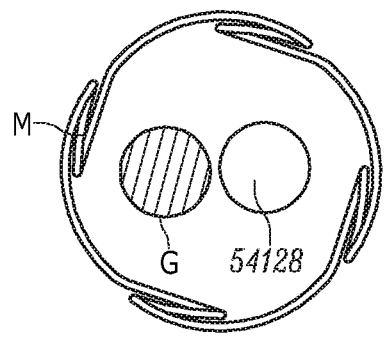
Figure 67:
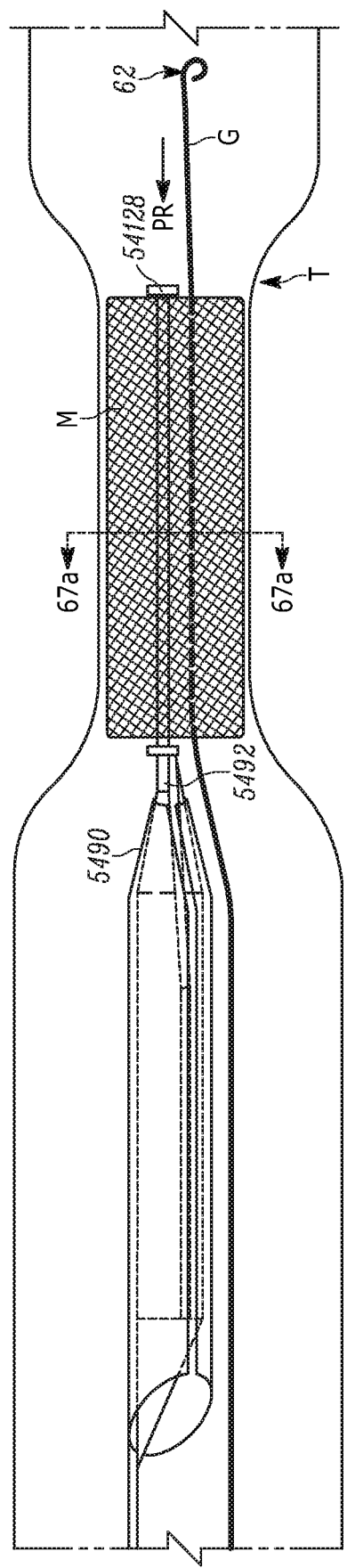

As shown in FIG. 64, with the balloon dilation rod open tip 55162 adjacent to the shaft side wall opening 54142, both of the implant delivery system 5486 and the balloon dilation device 5588 may be directed toward the target patient tissue site T until the outer sheath 5490 is laterally adjacent to the target patient tissue site T. FIGS. 64*a-h* depict cross-sectional views of various points along the introducer sheath B 322, the implant delivery system 5486, the balloon dilation device 5588, and the guidewire G, to show the arrangement of the introducer sheath B 322, the implant delivery system 5486, the balloon dilation device 5588, and the guidewire G in FIG. 64. As shown in FIGS. 65-67, with the implant delivery system 5486 at the target patient tissue site T, the expandable implant M may be exposed by moving the outer sheath delivery element 5498 in the longitudinally proximal direction (as shown as an arrow PR in FIGS. 65-67) to directly correspondingly cause the outer sheath 5490 to move in the longitudinally proximal direction. The guidewire G, the expandable implant M, and the shaft 5492 are maintained in place at the target patient tissue site T while the outer sheath 5490 is moved in the longitudinally proximal direction.

Figure 65B:
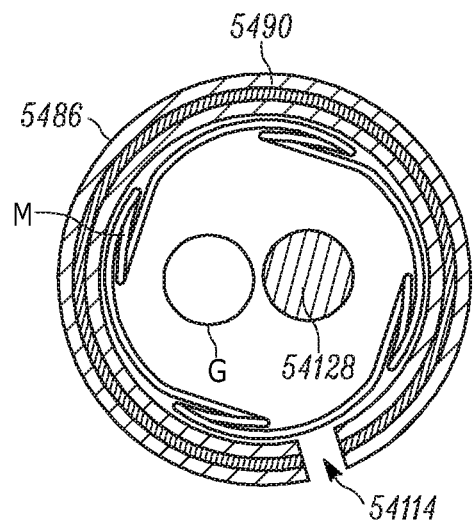
Figure 65C:
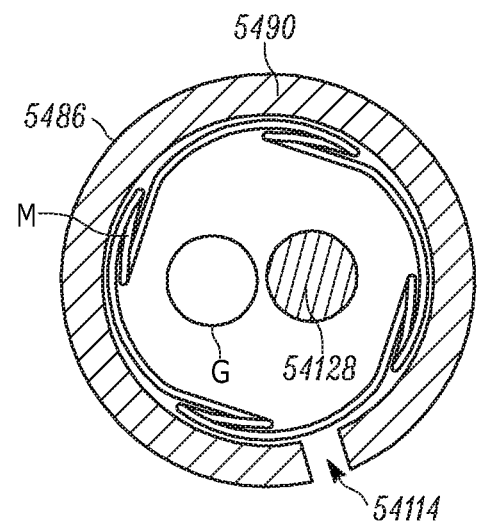
Figure 65D:
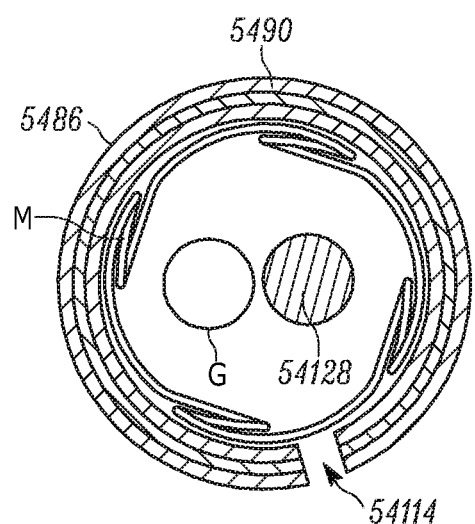
Figure 67A:
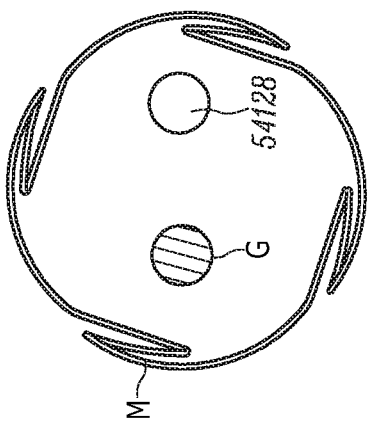
Figure 68B:
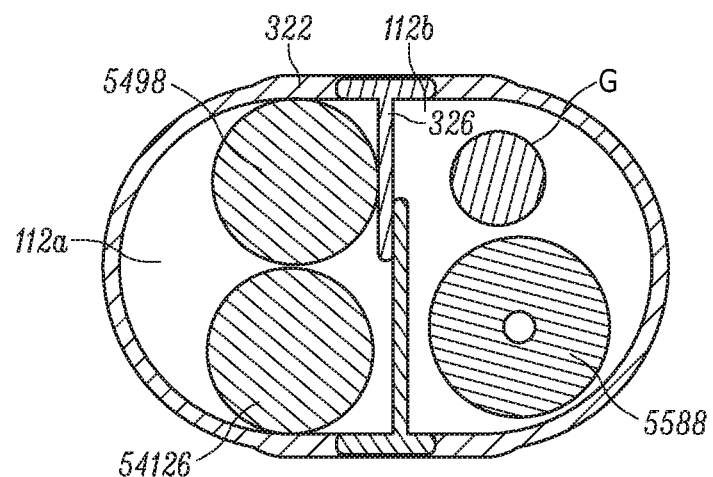
Figure 68C:
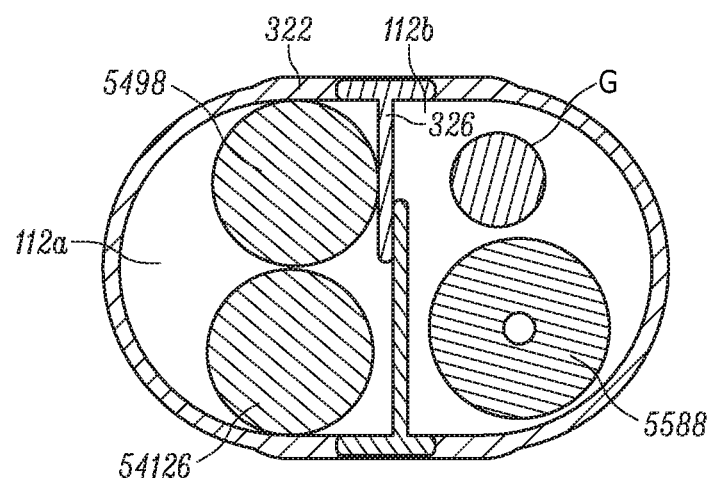
Figure 68D:
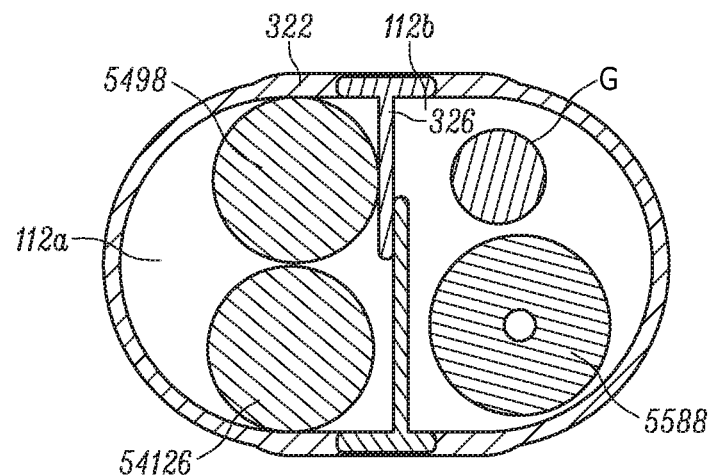
Figure 68E:
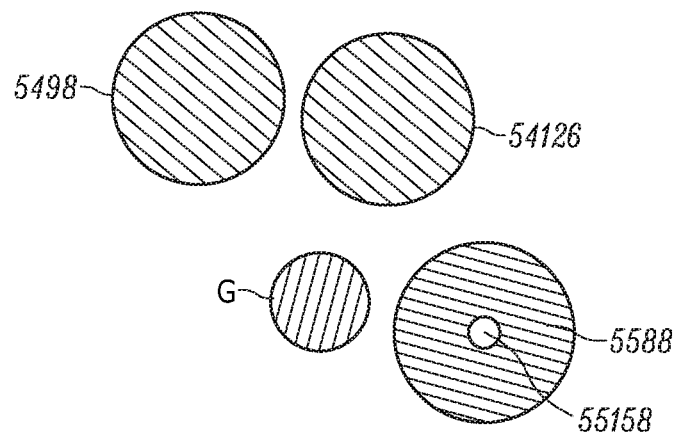

The outer sheath 5490 may be removed from the guidewire G while the outer sheath 5490 is moved in the longitudinally proximal direction. In particular, the movement of the outer sheath 5490 in the longitudinally proximal direction causes the outer sheath splitter 54146 to move along the implant holding pod open slit 54114 to selectively urge the implant holding pod open slit first surface 54116 elastically apart from the implant holding pod open slit second surface 54118 and accordingly push the guidewire G from the implant holding pod lumen 54112, while the guidewire G and the shaft 5492 are maintained at the target patient tissue site T. With the expandable implant M exposed, the properties of the expandable implant M are utilized to move the expandable implant M from the collapsed condition (as shown in FIGS. 65 and 66) toward the expanded condition (as shown in FIG. 67). FIGS. 65a-d depict cross-sectional views of various points along the implant delivery system 5486, to show the arrangement of the outer sheath 5490, the shaft 5492, the guidewire G, and the expandable implant M in FIG. 65. FIGS. 66a-d depict cross-sectional views of various points along the implant delivery system 5486, to show the arrangement of the outer sheath 5490, the shaft 5492, the guidewire G, and the expandable implant M in FIG. 66. FIG. 67a depicts a cross-sectional view of a point along the implant delivery system 5486, to show the arrangement of the shaft 5492, the guidewire G, and the expandable implant M in FIG. 67.

Figure 69:
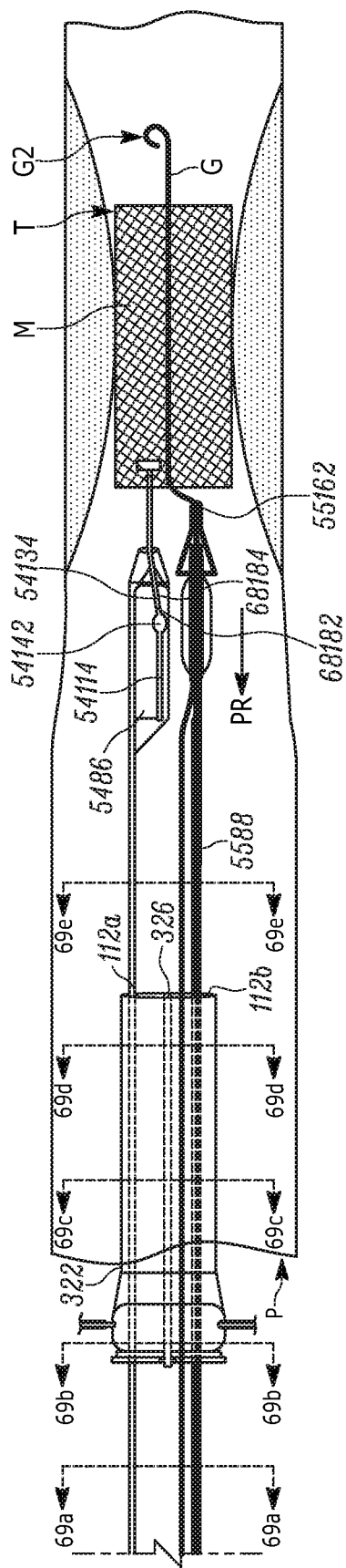
Figure 69A:
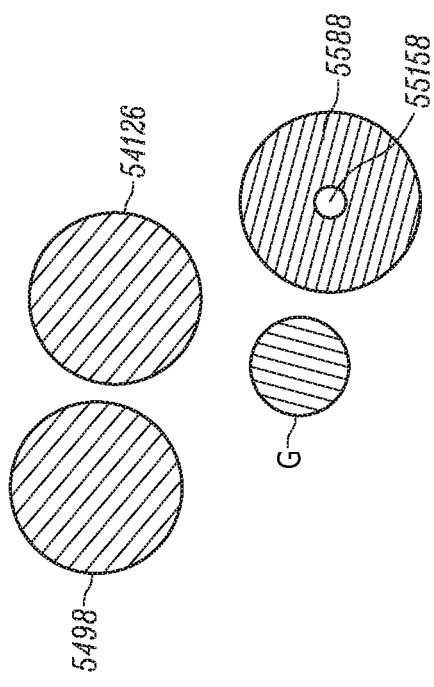
Figure 69B:
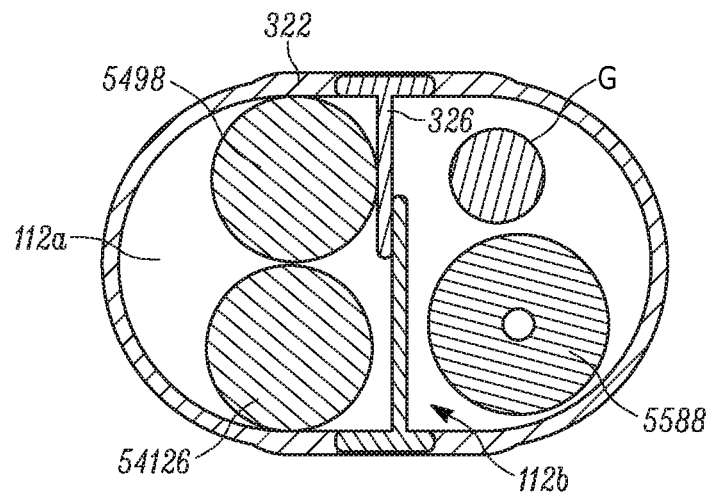
Figure 69C:
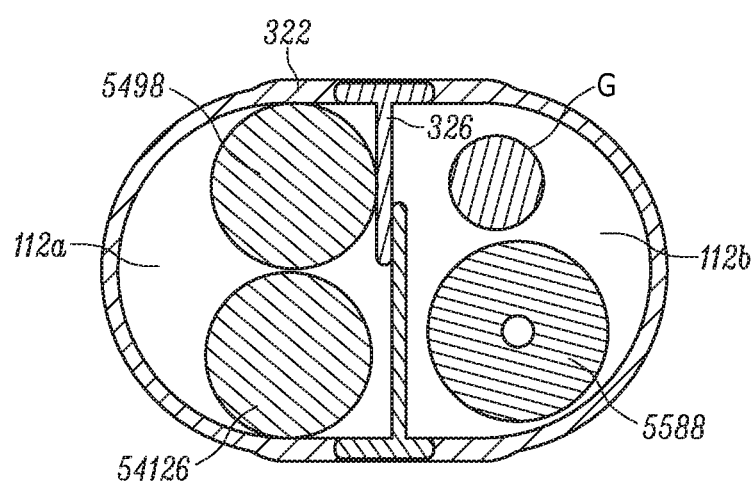
Figure 69D:
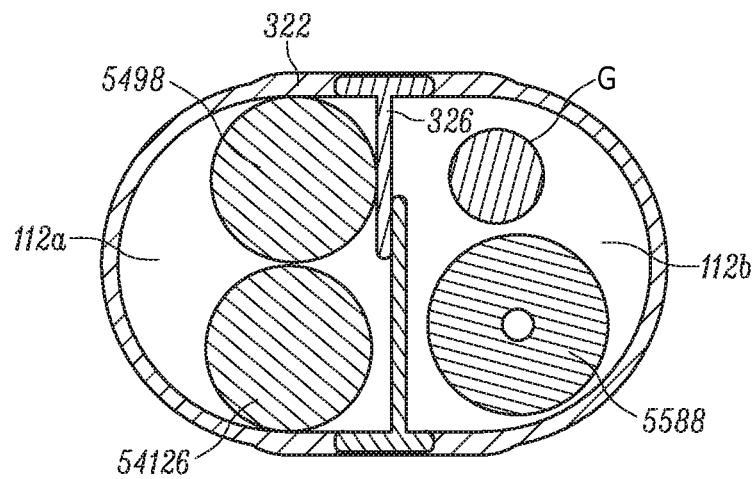
Figure 69E:
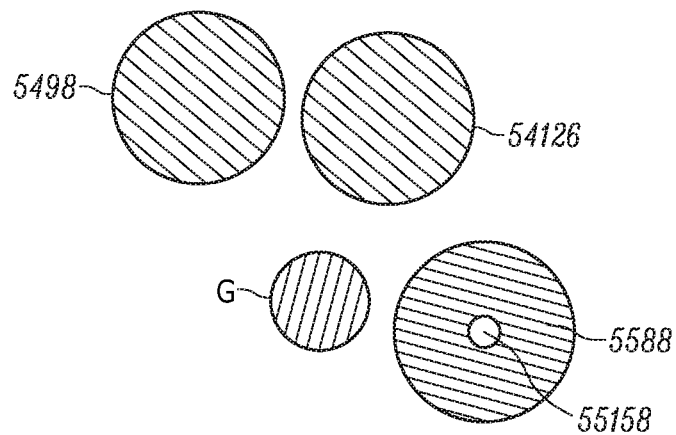
Figure 70B:
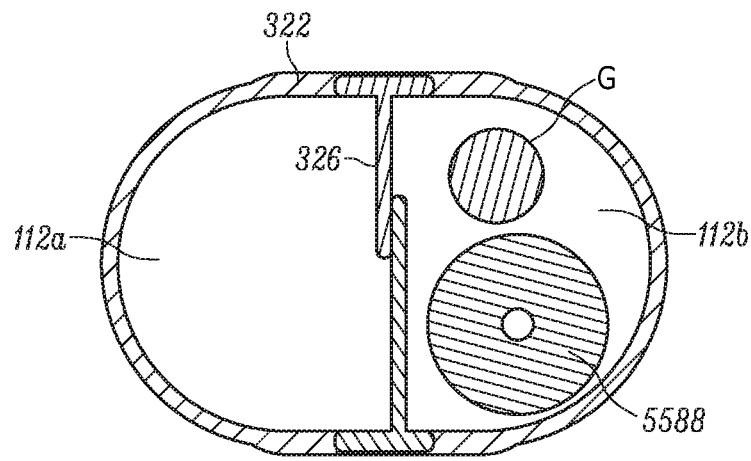
Figure 70C:
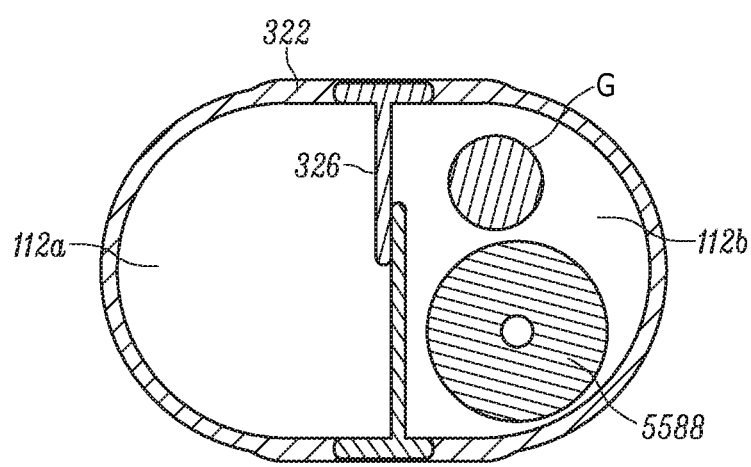
Figure 70D:
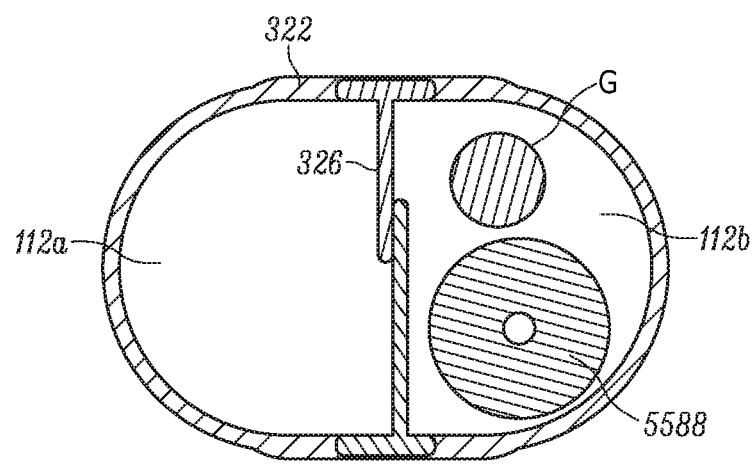
Figure 70E:
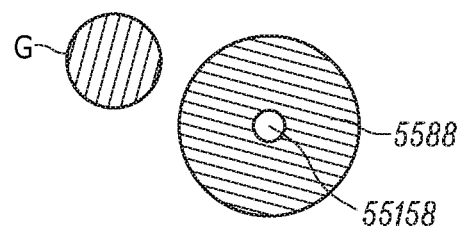
Figure 71B:
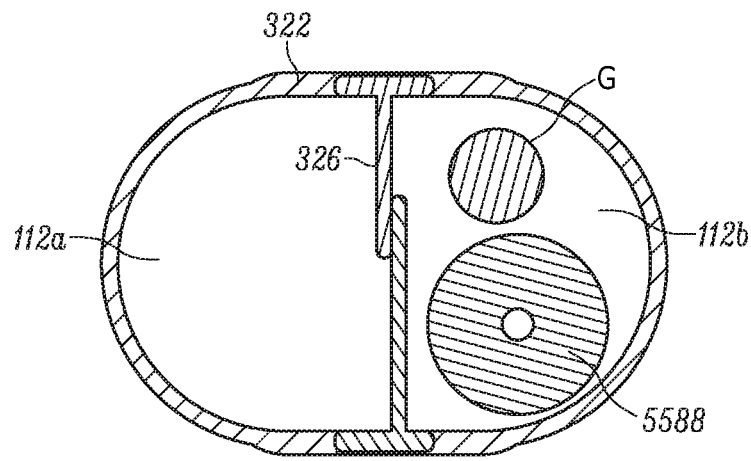
Figure 71C:
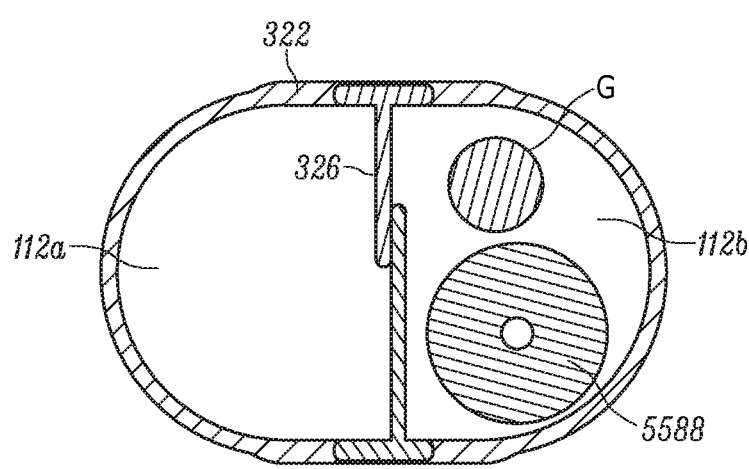
Figure 71D:
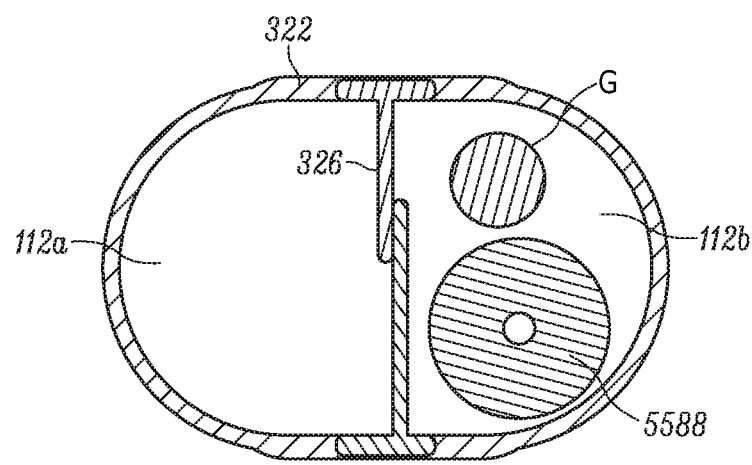
Figure 71E:
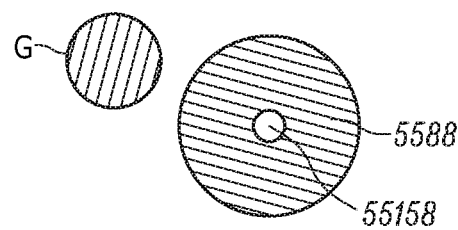

Alternatively to, or in addition to, the removal of the outer sheath 5490 as described above, the outer sheath 5490 may be removed from the guidewire G, for example, via the following sequence. As shown in FIGS. 68 and 69, the balloon dilation device 5588 may be directed over the guidewire G until the balloon dilation device 5588 is at least one abutting and at least partially within the implant holding open slit 54114. With the balloon dilation device 5588 pushing against and and/or at least partially in the implant holding pod open slit 54114, the outer sheath 5490 is longitudinally moved in the proximal direction to remove the outer sheath 5490 from the guidewire G. In particular, the movement of the outer sheath 5490 toward the proximal direction causes the balloon dilation device 5588 to selectively urge the implant holding pod open slit first surface 54116 at least partially elastically apart from the implant holding pod open slit second surface 54118 and remove the outer sheath 5490 from the guidewire G, while leaving the guidewire G and the shaft 5492 in place at the target patient tissue site T. Thus, the balloon dilation device 5588 can be thought of as acting as a pivot arrangement to urge the outer sheath 5490 from the guidewire G.

A user may then remove the shaft 5492 from the guidewire G, for example, via the following sequence. At least a portion of the balloon dilation device 5588 is directed over the guidewire G until the balloon dilation device 5588 is at least one of abutting and at least partially within the shaft side wall opening 54142. With the balloon dilation device 5588 pushing against and/or located at least partially in the shaft side wall opening 54142, the shaft 5492 is longitudinally moved toward the proximal direction to remove the shaft 5492 from the guidewire G. In particular, the movement of the shaft 5492 toward the proximal direction causes the balloon dilation device 5588 to selectively urge a shaft open slit first surface 68182 at least partially elastically apart from a shaft open slit second surface 68184 and remove the shaft 5492 from the guidewire G, while the guidewire G and the expanded implant M are maintained at the target patient tissue site T. Thus, the balloon dilation device 5588 can be thought of as acting as a pivot arrangement to urge the shaft 5492 from the guidewire G. The shaft open slit first surface 68182 oppositely faces and abuts shaft open slit second surface 68184 (see FIG. 54). The shaft open slit first surface 68182 and the shaft open slit second surface 68184 are selectively elastically separable, similar to that of the implant holding pod open slit first and second surfaces 54116, 54118.

FIGS. 68a-e depict cross-sectional views of various points along the introducer sheath B 322, the implant delivery system 5486, and the balloon dilation device 5588, to show the arrangement of the introducer sheath B 322, the implant delivery system 5486, the balloon dilation device 5588, and the guidewire G in FIG. 68. FIGS. 69a-e depict cross-sectional views of various points along the introducer sheath B 322, the implant delivery system 5486, and the balloon dilation device 5588, to show the arrangement of the introducer sheath B 322, the implant delivery system 5486, the balloon dilation device 5588, and the guidewire G in FIG. 69.

Figure 72:
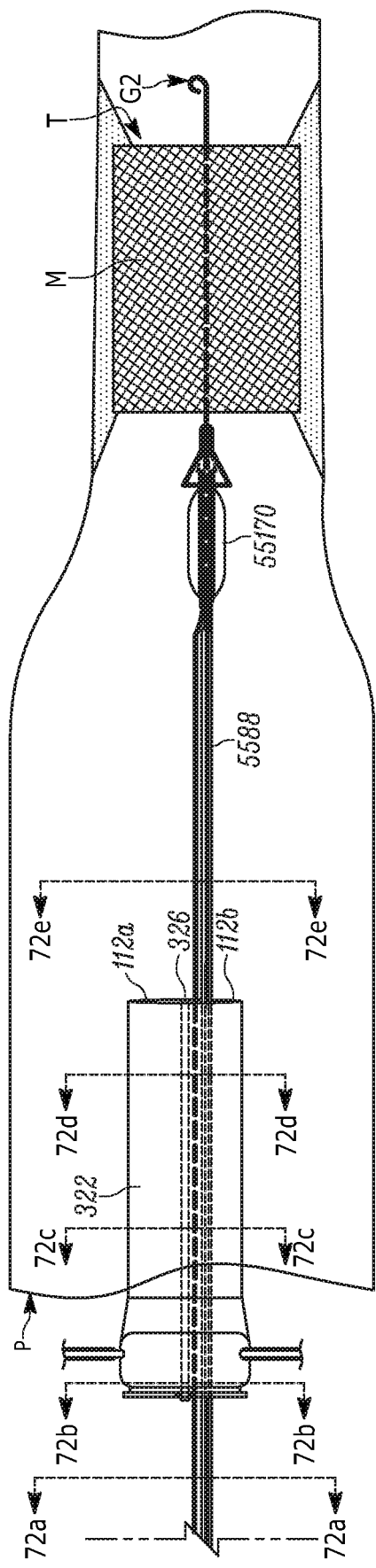
Figure 72A:
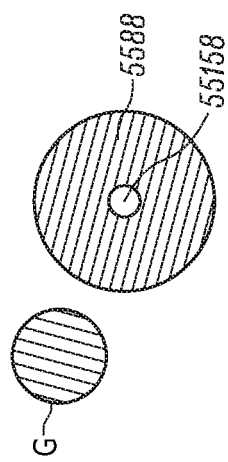
Figure 72B:
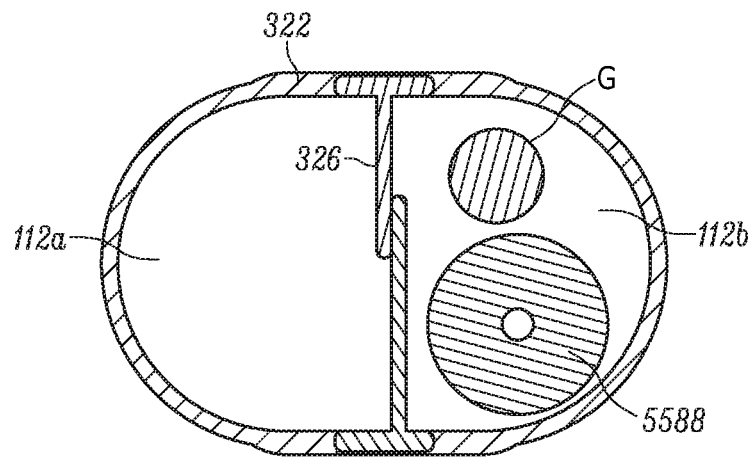
Figure 72C:
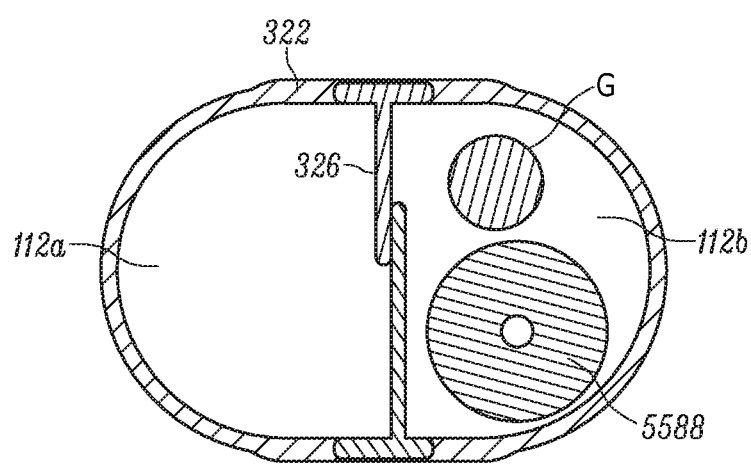
Figure 72D:
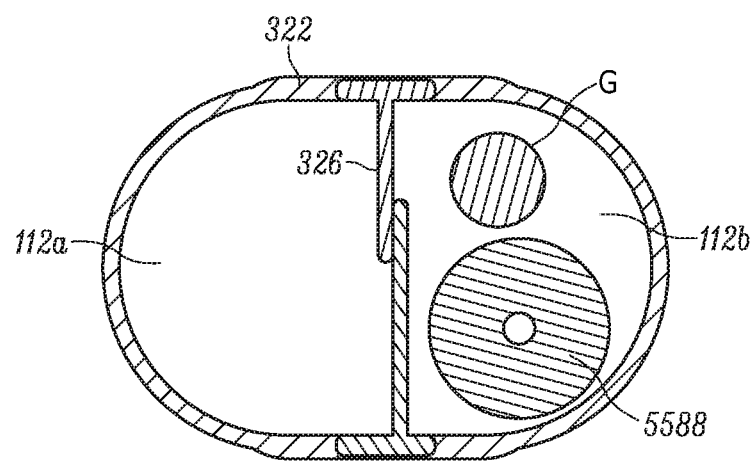
Figure 72E:
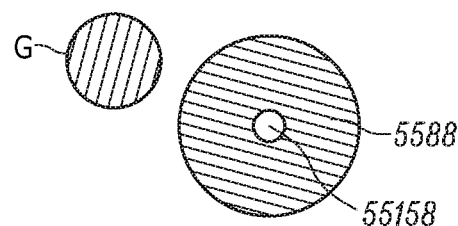

As shown in FIGS. 70 and 71, if desired by the user, the user may direct the balloon dilation device 5588 in the longitudinally distal direction (as shown as an arrow DI in FIGS. 70 and 71) to the target patient tissue site T to perform a medical procedure with the balloon dilation device 5588 at the target patient tissue site T. The balloon dilation device 5588 may be positioned with at least a portion of the expandable balloon 55170 within a diseased segment of the patient lumen and/or adjacent to an expandable implant inner surface MI. As shown in FIG. 71, the expandable balloon 55170 may be inflated to dilate the diseased segment of the patient lumen and/or cause the expandable implant M to further expand. FIGS. 70a-e depict cross-sectional views of various points along the introducer sheath B 322 and the balloon dilation device 5588, to show the arrangement of the introducer sheath B 322, the balloon dilation device 5588, and the guidewire G in FIG. 70. FIGS. 71a-e depict cross-sectional views of various points along the introducer sheath B 322 and the balloon dilation device 5588, to show the arrangement of the introducer sheath B 322, the balloon dilation device 5588, and the guidewire G in FIG. 71. As shown in FIG. 72, with the expandable implant M further expanded, the expandable balloon 55170 may be deflated. FIGS. 72a-e depict cross-sectional views of various points along the introducer sheath B 322 and the balloon dilation device 5588, to show the arrangement of the introducer sheath B 322, the balloon dilation device 5588, and the guidewire G in FIG. 72.

Although the introducer sheath B 322 has been described as being used for the insertion of various medical instruments 3360, it is to be understood that the various medical instruments 3360 may be inserted utilizing the other example configurations of the introducer sheath 100 in substantially the same sequence of operation. For example, the introducer sheath A 104 may be utilized in the same sequence of operation as described above. The introducer sheath C 1536 may be utilized in substantially the same sequence of operation as described. However, in the utilization of introducer C 1536, the septum C 1538 is removed from the introducer sheath C 1536 before the guidewire G is transitioned from the first sheath lumen 112a to the second sheath lumen 112b. With the removable septum removed from the introducer sheath C 1536, a medical instrument 3360, such as the second dilator 4384 or the balloon dilation device 5588, is directed toward the target patient tissue site T along the guidewire G and at least partially through the second sheath lumen 112b of the plurality of sheath lumens 112a, 112b. With the medical instrument 3360 at the target patient tissue site T, the removable septum C 1538 may be inserted into the introducer sheath C 1536. At least one of the medical instrument 3360 and the septum C 1538 urges the guidewire G from the first sheath lumen 112a to the second sheath lumen 112b as the medical instrument 3360 moves at least partially through the second sheath lumen 112b and/or as the septum C is inserted into the introducer sheath C 1536, while the guidewire G is maintained at the target patient tissue site T. The introducer sheath D 2148 may be utilized in the same sequence of operation as described above as the guidewire G is able to pass between the plurality of sheath lumens 112a, 112b through the opening 2252 in the septum D 2150. The introducer sheath E 2354 may be utilized to direct at least one medical instrument 3360 to the target patient tissue site T through at least one of the plurality of sheath lumens 112*a*, 112*b*. However, the introducer sheath E 2354 does not allow for the transition of the guidewire G between the plurality of sheath lumens 112*a*, 112*b*.

Any of the alternate introducer sheath 100 configurations and the medical instruments 3360, when provided may be at least partially formed from silicone, polyethylene, polypropylene, stainless steel, titanium, rubber, latex, polychloroprene, nylon, any other biocompatible material, or any combination thereof.

It is contemplated that the introducer sheath 100 may provide the user with the ability to insert multiple medical instruments 3360 toward a target patient tissue site T through a single patient tissue access point P. The ability to insert multiple medical instruments 3360 toward a target patient tissue site T through a single patient tissue access point P may assist in reducing potential trauma, complications, and/or risks to the patient that result from the creation of multiple patient tissue access points P.

Additionally, it is contemplated that the introducer sheath 100 may allow for a smaller patient tissue access point P than what may be otherwise necessary for the insertion of multiple medical instruments 3360. For example, instead of using one large lumen to introduce multiple medical instruments 3360 through a large patient tissue access point P, each of the medical instruments 3360 can be inserted through a separate lumen 112 of the plurality of sheath lumens 112 so that size of the lumens 112, and the introducer sheath 100 as a whole, is kept to a minimum. Further, delivering multiple medical instruments 3360 through a larger lumen can cause friction between the medical instruments 3360. By delivering the multiple medical instruments 3360 through separate sheath lumens 112, the friction between the medical instruments 3360 is either removed or substantially decreased.

It is contemplated that the introducer sheath may provide the user with the ability to deliver at least one of the medical instruments 3360, when provided, to a target patient tissue site T of a patient lumen along a single guidewire G and remove at least one of the medical instruments 3360 in the patient lumen. This allows the user to direct another medical instrument 3360 to the target patient tissue site T of the patient lumen, without having to remove at least one of the delivered medical instruments 3360 outside of the patient lumen.

The expandable implant M may be at least partially formed from materials having self-expanding properties, such as, but not limited to, stainless steel and shape memory materials. An example of a shape memory material is, for example, Nitinol. In such case, the expandable implant M at least partially formed from materials having self-expanding properties may be moved to the collapsed condition through a direct and/or indirect user interaction, and mounted on the implant delivery element outer surface 54130 and/or within the implant holding pod lumen 54112. For example, an expandable implant M at least partially formed from a shape memory material may be cooled to a temperature below the transition temperature range, moved to the collapsed condition, and mounted on the implant delivery element outer surface 54130 and/or within the implant holding pod lumen 54112. When the expandable implant M at least partially formed from a shape memory material is exposed at the target patient tissue site T, the self-expanding properties of the expandable implant M may at least partially cause the expandable implant M to move from the collapsed condition toward the expanded condition. Further, the temperature of the environment at the target patient tissue site T at least partially causes the expandable implant M at least partially formed from a shape memory material to move from the collapsed condition toward the expanded condition.

It is contemplated that an expandable implant M, when provided, at least partially formed from a shape memory material may be more easily conformable to the shape of the target patient tissue site T than what an expandable implant M not made at least partially from a shape memory material would be. An expandable implant M that has self-expanding properties, but is not at least partially made from a shape memory material, might not have to be cooled in order to be moved toward the collapsed condition, and/or might not require exposure to the temperature of the environment at the target patient tissue site T in order to move from the collapsed condition toward the expanded condition.

While aspects of this disclosure have been particularly shown and described with reference to the example aspects above, it will be understood by those of ordinary skill in the art that various additional aspects may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. In an effort to maintain clarity in the Figures, certain ones of duplicative components shown have not been specifically numbered, but one of ordinary skill in the art will realize, based upon the components that were numbered, the element numbers which should be associated with the unnumbered components; no differentiation between similar components is intended or implied solely by the presence or absence of an element number in the Figures. Any of the described structures and components could be integrally formed as a single unitary or monolithic piece or made up of separate sub-components, with either of these formations involving any suitable stock or bespoke components and/or any suitable material or combinations of materials; however, the chosen material(s) should be biocompatible for many applications. Any of the described structures and components could be disposable or reusable as desired for a particular use environment. Any component could be provided with a user-perceptible marking to indicate a material, configuration, at least one dimension, or the like pertaining to that component, the user-perceptible marking potentially aiding a user in selecting one component from an array of similar components for a particular use environment. The term "substantially" is used herein to indicate a quality that is largely, but not necessarily wholly, that which is specified—a "substantial" quality admits of the potential for some relatively minor inclusion of a non-quality item. Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one aspect or configuration could be provided, singly or in combination with other structures or features, to any other aspect or configuration, as it would be impractical to describe each of the aspects and configurations discussed herein as having all of the options discussed with respect to all of the other aspects and configurations. A device or method incorporating any of these features should be understood to fall under the scope of this disclosure as determined based upon the claims below and any equivalents thereof.

Other aspects, objects, and advantages may be obtained from a study of the drawings, the disclosure, and the appended claims.

I claim:

1. An introducer sheath, comprising:
   a plurality of sheath lumens extending longitudinally between sheath proximal and distal ends of the introducer sheath; and
   a septum extending between the sheath proximal and distal ends and selectively laterally separating each of the sheath lumens from one another, the septum being at least partially formed from a deformable and elastomeric material, the septum having a first portion fixed to a portion of an interior wall of the introducer sheath and a free second portion laterally spaced from the first portion, the septum having a biased condition in which the plurality of sheath lumens are at least partially isolated from one another, at least a portion of the septum and at least a portion of the interior wall of the introducer sheath collectively defining each of the sheath lumens when the septum is in the biased condition, the septum being selectively deflectable from the biased condition to at least partially place at least one of the plurality of sheath lumens in fluid communication with at least one other of the plurality of sheath lumens, the second portion of the septum being at least partially pivoted laterally with respect to the fixed first portion of the septum as the septum is deflected from the biased condition.

2. The introducer sheath of claim 1, wherein the septum has a septum first end and a laterally spaced free septum second end, the septum first end being fixed to a portion of the interior wall of the introducer sheath, the septum second end abutting a portion of the interior wall opposite from the septum first end when the septum is in the biased condition to at least partially isolate each of plurality of sheath lumens from one another.

3. The introducer sheath of claim 2, wherein when the septum is selectively deflected from the biased condition, at least a portion of the septum second end is pivoted laterally away and spaced apart from the portion of the interior wall opposite from the septum first end to at least partially place at least one of the plurality of sheath lumens in fluid communication with at least one other of the plurality of sheath lumens.

4. The introducer sheath of claim 1, wherein the septum comprises a plurality of segments, each of the segments having a segment first end and a laterally spaced free segment second end, each of the segment first ends being fixed to a portion of the interior wall of the introducer sheath and spaced apart from other segment first ends, each of the segment second ends abutting a portion of another of the segment second ends when the septum is in the biased condition to at least partially isolate each of plurality of sheath lumens from one another.

5. The introducer sheath of claim 4, wherein when the septum is selectively deflected from the biased condition, at least a portion of the segment second end of at least one of the segments is pivoted laterally away and spaced apart from the segment second end of at least one other of the segments to at least partially place at least one of the plurality of sheath lumens in fluid communication with at least one other of the plurality of sheath lumens.

6. The introducer sheath of claim 1, wherein at least a portion of the septum along a length of the septum is capable of being moved from the biased condition while at least one other portion of the septum along the length of the septum is maintained in the biased condition.

7. The introducer sheath of claim 1, wherein at least a portion of the septum along a length of the septum is capable of being moved from the biased condition in a first direction while at least one other portion of the septum along the length of the septum is at least one of in the biased condition and moved in a second direction, different from the first direction.

8. A method for inserting at least one medical instrument directly toward a target patient tissue site, the method comprising:
   providing an introducer sheath having a plurality of sheath lumens extending between sheath proximal and distal ends of the introducer sheath;
   inserting a guidewire distal end into a target patient tissue site;
   directing the guidewire proximal end through a first sheath lumen of the plurality of sheath lumens;
   directing the introducer sheath toward the target patient tissue site along the guidewire;
   directing the guidewire proximal end at least partially through a first medical instrument; and
   directing the first medical instrument to the target patient tissue site along the guidewire and at least partially through a second sheath lumen of the plurality of sheath lumens, the first medical instrument urging the guidewire from the first sheath lumen to the second sheath lumen as the first medical instrument moves at least partially through the second sheath lumen, while the guidewire is maintained at the target patient tissue site.

9. The method of claim 8, wherein the introducer sheath includes a septum extending between the sheath proximal and distal ends and selectively separating each of the sheath lumens from one another, the septum being at least partially formed from a deformable and elastomeric material, the septum having a biased condition in which the plurality of sheath lumens are at least partially isolated from one another, the septum being selectively deflectable from the biased condition to at least partially place at least one of the plurality of sheath lumens in fluid communication with at least one other of the plurality of sheath lumens, and
   as the first medical instrument moves at least partially through the second sheath lumen, the first medical instrument urges the guidewire from the first sheath lumen to the second sheath lumen by causing at least a portion of the guidewire to be urged into at least a portion of the septum to selectively deflect at least a portion of the septum from the biased condition,
   the deflection of the septum at least partially providing fluid communication between the first and second sheath lumens so that the portion of the guidewire being urged into the septum passes into the second sheath lumen from the first sheath lumen.

10. The method of claim 9, wherein the septum has a septum first end and a laterally spaced septum second end, the septum first end being attached to a portion of an interior wall of the introducer sheath, the septum second end abutting a portion of the interior wall opposite from the septum first end when the septum is in the biased condition to at least partially isolate each of plurality of sheath lumens from one another, and when the septum is selectively deflected from the biased condition, at least a portion of the septum second end is spaced apart from the portion of the interior wall opposite from the septum first end to at least partially place at least one of the plurality of sheath lumens in fluid communication with at least one other of the plurality of sheath lumens.

11. The method of claim 9, wherein the septum comprises a plurality of segments, each of the segments having a segment first end and a laterally spaced segment second end, each of the segment first ends being attached to a portion of an interior wall of the introducer sheath and spaced apart from other first segment ends, each of the segment second ends abutting a portion of another of the segment second ends when the septum is in the biased condition to at least partially isolate each of plurality of sheath lumens from one another, and when the septum is selectively deflected from the biased condition, at least a portion of the segment second end of at least one of the segments is spaced apart from the segment second end of at least one other of the segments to at least partially place at least one of the plurality of sheath lumens in fluid communication with at least one other of the plurality of sheath lumens.

12. The method of claim 8, wherein the introducer sheath includes a selectively removable septum, when the removable septum is inserted into the introducer sheath, the removable septum extends between the sheath proximal and distal ends and selectively separates each of the plurality of sheath lumens from one another to at least partially isolate each of plurality of sheath lumens from one another, and when the removable septum is removed from the introducer sheath, at least one of the plurality of sheath lumens is in fluid communication with at least one other of the plurality of sheath lumens, the method further including:
 removing the removable septum from the introducer sheath;
 with the removable septum removed from the introducer sheath, directing the first medical instrument to the target patient tissue site along the guidewire and at least partially through the second sheath lumen of the plurality of sheath lumens, the first medical instrument urging the guidewire from the first sheath lumen to the second sheath lumen as the second medical instrument moves at least partially through the second sheath lumen, while maintaining the guidewire at the target patient tissue site; and
 with the first medical instrument at the target patient tissue site, inserting the removable septum into the introducer sheath.

13. The method of claim 8, including:
 directing the guidewire proximal end at least partially through a second medical instrument; and
 directing the second medical instrument to the target patient tissue site along the guidewire and at least partially through the first sheath lumen.

14. The method of claim 13, wherein the first medical instrument is a second dilator and the second medical instrument is a first dilator, the first dilator having a first dilator distal end, a first dilator outer surface, and a first dilator lumen, the first dilator distal end having a first dilator open tip, the first dilator having a first dilator side wall opening, the first dilator side wall opening selectively placing the first dilator outer surface in fluid communication with the first dilator lumen, the second dilator having a second dilator distal end and a second dilator lumen, the second dilator distal end having a second dilator open tip, the method further including:
 directing the guidewire proximal end into the first dilator open tip, through at least a portion of the first dilator lumen, and out of the first dilator through the first dilator side wall opening;
 directing the guidewire proximal end into the second dilator open tip, through at least a portion of the second dilator lumen, and out from the second dilator; and
 directing the second dilator to the target patient tissue site along the guidewire and at least partially through the second lumen until the second dilator open tip is adjacent to the first dilator side wall opening.

15. The method of claim 14, wherein the first dilator has a first dilator open slit, the first dilator open slit extending between the first dilator side wall opening and the first dilator open tip, first dilator open slit includes a first dilator open slit first surface and a first dilator open slit second surface, the first dilator open slit first surface being oppositely facing and abutting the first dilator open slit second surface, the first dilator open slit first surface and the first dilator open slit second surface being selectively elastically separable, the method further including:
 directing each of the second dilator open tip and at least a portion of the second dilator distal end at least one of adjacent to and at least partially into the first dilator side wall opening; and
 with the second dilator distal end at least one of adjacent to and at least partially in the first dilator side wall opening, moving the first dilator in a longitudinally proximal direction to remove the first dilator from the guidewire, movement of the first dilator in the longitudinally proximal direction causing the second dilator distal end to selectively urge the first dilator open slit first surface elastically apart from the first dilator open slit second surface and the first dilator to be removed from the guidewire, while the guidewire is maintained at the target patient tissue site.

16. A method for inserting an introducer sheath through a patient tissue access point, the method comprising:
 providing the introducer sheath having a plurality of sheath lumens extending between sheath proximal and distal ends of the introducer sheath;
 inserting a guidewire distal end through the patient tissue access point;
 directing a guidewire proximal end through a first sheath lumen of the plurality of sheath lumens;
 directing the guidewire proximal end at least partially through a first medical instrument;
 directing the first medical instrument over the guidewire and at least partially through the first sheath lumen;
 directing the guidewire proximal end at least partially through a second medical instrument;
 directing the second medical instrument over the guidewire and at least partially through a second sheath lumen of the plurality of sheath lumens, the second medical instrument urging the guidewire from the first sheath lumen to the second sheath lumen as the second medical instrument moves at least partially through the second sheath lumen, while the guidewire is maintained through the patient tissue access point;
 aligning the first and second medical instruments with the introducer sheath so that at least a portion of both of the first and second medical instruments extend out from the introducer sheath and form a smooth outer contour with the sheath distal end; and
 with the first and second medical instruments aligned with the introducer sheath, collectively directing the introducer sheath, the first medical instrument, and the second medical instrument through the patient tissue access point along the guidewire.

17. The method of claim 16, wherein the first medical instrument is a first dilator and the second medical instrument is a second dilator, the first dilator having a first dilator distal end, a first dilator outer surface, and a first dilator lumen, the first dilator distal end having a first dilator open tip, the first dilator having a first dilator side wall opening, the first dilator side wall opening selectively placing the first dilator outer surface in fluid communication with the first dilator lumen, the first dilator having a first dilator open slit, the first dilator open slit extending between the first dilator side wall opening and the first dilator open tip, first dilator open slit includes a first dilator open slit first surface and a first dilator open slit second surface, the first dilator open slit first surface being oppositely facing and abutting the first dilator open slit second surface, the first dilator open slit first surface and the first dilator open slit second surface being selectively elastically separable, and the second dilator having a second dilator distal end and a second dilator lumen, the second dilator distal end having a second dilator open tip, the method further including:

directing each of the second dilator open tip and at least a portion of the second dilator distal end at least one of adjacent to and at least partially into the first dilator side wall opening; and with the second dilator distal end at least one of adjacent to and at least partially in the first dilator side wall opening, moving the first dilator in a longitudinally proximal direction to remove the first dilator from the guidewire, movement of the first dilator in the longitudinally proximal direction causing the second dilator distal end to selectively urge the first dilator open slit first surface elastically apart from the first dilator open slit second surface and the first dilator to be removed from the guidewire, while the guidewire is maintained through the patient tissue access point.

18. A method for transitioning a guidewire between a plurality of lumens within a patient, the method comprising:
providing an introducer sheath including
a plurality of sheath lumens extending between sheath proximal and distal ends of the introducer sheath, and
a selectively removable septum extending between the sheath proximal and distal ends and selectively separating each of the plurality of sheath lumens from one another to at least partially isolate each of plurality of sheath lumens from one another when the removable septum is inserted into the introducer sheath, at least one of the plurality of sheath lumens being in fluid communication with at least one other of the plurality of sheath lumens when the removable septum is removed from the introducer sheath;
inserting a guidewire distal end into a target patient tissue site;
directing a guidewire proximal end through a first sheath lumen of the plurality of sheath lumens;
directing the introducer sheath toward the target patient tissue site along the guidewire;
removing the removable septum from the introducer sheath;
with the removable septum removed from the introducer sheath, urging the guidewire proximal end from the first sheath lumen to a second sheath lumen of the plurality of sheath lumens; and
with the guidewire proximal end in the second sheath lumen, inserting the removable septum into the introducer sheath, the removable septum urging the guidewire from the first sheath lumen to the second sheath lumen as the removable septum is inserted into the introducer sheath, while the guidewire is maintained at the target patient tissue site.

19. The introducer sheath of claim 1, wherein a bend forms in the septum as the free second portion of the septum is at least partially pivoted laterally with respect to the fixed first portion of the septum.

20. An introducer sheath, comprising:
a sheath body having oppositely facing interior and exterior surfaces;
a plurality of sheath lumens extending longitudinally through the sheath body between sheath proximal and distal ends of the introducer sheath; and
a septum extending between the sheath proximal and distal ends and selectively laterally separating each of the sheath lumens from one another, the septum being at least partially formed from a deformable and elastomeric material, the septum having a biased condition in which the plurality of sheath lumens are at least partially isolated from one another, at least a portion of the septum and at least a portion of the interior surface of the introducer sheath collectively defining each of the sheath lumens when the septum is in the biased condition, the septum being selectively deflectable from the biased condition to at least partially place at least one of the plurality of sheath lumens in fluid communication with at least one other of the plurality of sheath lumens, a cross-sectional shape of the exterior surface of the sheath body remaining substantially unchanged as the septum is deflected from the biased condition.

* * * * *